United States Patent
Kozlov et al.

(10) Patent No.: US 10,288,608 B2
(45) Date of Patent: May 14, 2019

(54) POLYNUCLEOTIDE CONJUGATES AND METHODS FOR ANALYTE DETECTION

(71) Applicant: Prognosys Biosciences, Inc., San Diego, CA (US)

(72) Inventors: Igor A. Kozlov, San Diego, CA (US); John Andrew Altin, San Diego, CA (US); Petr Capek, San Diego, CA (US); Mark S. Chee, San Diego, CA (US)

(73) Assignee: Prognosys Biosciences, Inc., San Diego, CA (US)

( * ) Notice: Subject to any disclaimer, the term of this patent is extended or adjusted under 35 U.S.C. 154(b) by 0 days.

(21) Appl. No.: 15/035,206

(22) PCT Filed: Nov. 7, 2014

(86) PCT No.: PCT/US2014/064588
§ 371 (c)(1),
(2) Date: May 6, 2016

(87) PCT Pub. No.: WO2015/070037
PCT Pub. Date: May 14, 2015

(65) Prior Publication Data
US 2016/0291007 A1    Oct. 6, 2016

Related U.S. Application Data

(60) Provisional application No. 61/902,105, filed on Nov. 8, 2013.

(51) Int. Cl.
| | |
|---|---|
| *C12Q 1/6804* | (2018.01) |
| *G01N 33/543* | (2006.01) |
| *G01N 33/58* | (2006.01) |
| *G01N 33/68* | (2006.01) |
| *C12Q 1/6816* | (2018.01) |
| *C12Q 1/689* | (2018.01) |

(52) U.S. Cl.
CPC ..... *G01N 33/54393* (2013.01); *C12Q 1/6804* (2013.01); *C12Q 1/689* (2013.01); *C12Q 1/6816* (2013.01); *G01N 33/54306* (2013.01); *G01N 33/58* (2013.01); *G01N 33/6845* (2013.01); *G01N 33/6854* (2013.01); *G01N 2458/10* (2013.01)

(58) Field of Classification Search
None
See application file for complete search history.

(56) References Cited

U.S. PATENT DOCUMENTS

| | | |
|---|---|---|
| 5,002,882 A | 3/1991 | Lunnen et al. |
| 5,512,439 A | 4/1996 | Hornes et al. |
| 6,210,894 B1 | 4/2001 | Brennan |
| 6,258,558 B1 | 7/2001 | Szostak et al. |
| 6,261,804 B1 | 7/2001 | Szostak et al. |
| 6,281,804 B1 | 8/2001 | Haller et al. |
| 6,344,316 B1 | 2/2002 | Lockhart et al. |
| 6,416,950 B1 | 7/2002 | Lohse et al. |
| 6,485,982 B1 | 11/2002 | Charlton |
| 6,518,018 B1 | 2/2003 | Szostak et al. |
| 6,579,695 B1 | 6/2003 | Lambalot et al. |
| 6,632,641 B1 | 10/2003 | Brennan et al. |
| 6,800,453 B2 | 10/2004 | LaBaer et al. |
| 6,878,515 B1 | 4/2005 | Landegren et al. |
| 7,118,883 B2 | 10/2006 | Inoue et al. |
| 7,192,735 B2 | 3/2007 | Lambalot et al. |
| 7,229,769 B2 | 6/2007 | Kozlov et al. |
| 7,270,950 B2 | 9/2007 | Szostak et al. |
| 7,378,242 B2 | 5/2008 | Hurt et al. |
| 7,393,665 B2 | 7/2008 | Brenner |
| 7,407,757 B2 | 8/2008 | Brenner |
| 7,537,897 B2 | 5/2009 | Brenner |
| 7,544,473 B2 | 6/2009 | Brenner |
| 7,579,153 B2 | 8/2009 | Brenner |
| 7,635,566 B2 | 12/2009 | Brenner |
| 7,666,612 B2 | 2/2010 | Johnsson et al. |
| 7,674,752 B2 | 3/2010 | He et al. |

(Continued)

FOREIGN PATENT DOCUMENTS

| | | |
|---|---|---|
| EP | 1712623 | 10/2006 |
| JP | 2011-182702 | 6/2011 |

(Continued)

OTHER PUBLICATIONS

Tian et al (2009 Anal Chem 81:5218-25).*
Cerutti et al (2001 JBC 276:12769-73).*
Office Action for U.S. Appl. No. 13/266,568, dated Mar. 29, 2013.
Response to Office Action for U.S. Appl. No. 13/266,568, filed Aug. 29, 2013.
Final Office Action for U.S. Appl. No. 13/266,568, dated Dec. 5, 2013.
Response After Final Office Action for U.S. Appl. No. 13/266,568, filed Mar. 4, 2014.
Office Action for U.S. Appl. No. 13/266,568, dated Mar. 26, 2013.
Response to Office Action for U.S. Appl. No. 13/266,568, filed Jun. 26, 2014.

(Continued)

*Primary Examiner* — Christopher M Gross
(74) *Attorney, Agent, or Firm* — Morrison & Foerster LLP

(57) ABSTRACT

The present disclosure provides polynucleotide conjugates, methods, and assay systems for use in detecting the presence, absence, and/or amount of an analyte in a sample. Various polynucleotide conjugates, conjugate pairs, sets, libraries, and assay systems comprising the same are disclosed. In particular, methods and assay systems for antibody detection and analysis are provided. For example, assays capable of high levels of multiplexing are used for antibody detection and analysis in a biological sample, e.g., Lyme disease patient samples. The presently disclosed polynucleotide conjugates, methods, and assay systems can be used to provide sensitive and reliable diagnosis, even at early stages of a disease or condition. Use for monitoring disease progression and prognosis is also disclosed.

20 Claims, 16 Drawing Sheets

Specification includes a Sequence Listing.

(56) References Cited

U.S. PATENT DOCUMENTS

| | | |
|---|---|---|
| 7,776,547 B2 | 8/2010 | Roth |
| 7,858,321 B2 | 12/2010 | Glezer et al. |
| 8,207,093 B2 | 6/2012 | Szostak et al. |
| 8,337,851 B2 | 12/2012 | Aukerman |
| 8,343,500 B2 | 1/2013 | Wraith |
| 9,085,798 B2 | 7/2015 | Chee |
| 2003/0087232 A1 | 5/2003 | Christians et al. |
| 2003/0096323 A1 | 5/2003 | James |
| 2003/0113713 A1 | 6/2003 | Glezer et al. |
| 2003/0232382 A1 | 6/2003 | Brennan et al. |
| 2003/0138879 A1 | 7/2003 | Lambalot et al. |
| 2003/0162216 A1 | 8/2003 | Gold et al. |
| 2003/0224419 A1 | 12/2003 | Corcoran et al. |
| 2003/0235852 A1 | 12/2003 | Roberts et al. |
| 2004/0112442 A1 | 6/2004 | Maerkl |
| 2005/0003431 A1 | 1/2005 | Wucherpfennig |
| 2005/0026188 A1 | 2/2005 | Van Kessel et al. |
| 2005/0048580 A1 | 3/2005 | LaBaer et al. |
| 2005/0164292 A1 | 7/2005 | Faroqui et al. |
| 2005/0255548 A1 | 11/2005 | Lipovsek et al. |
| 2005/0260653 A1 | 11/2005 | LaBaer et al. |
| 2006/0003394 A1 | 1/2006 | Song et al. |
| 2006/0046313 A1 | 3/2006 | Roth et al. |
| 2006/0134669 A1 | 6/2006 | Casasanta, III |
| 2006/0199207 A1 | 9/2006 | Matysiak |
| 2006/0216721 A1 | 9/2006 | Kozlov et al. |
| 2006/0216775 A1 | 9/2006 | Burkhart et al. |
| 2006/0228758 A1 | 10/2006 | Muchhal |
| 2006/0275799 A1 | 12/2006 | Banerjee et al. |
| 2007/0014810 A1 | 1/2007 | Baker et al. |
| 2007/0020625 A1 | 1/2007 | Duchaud et al. |
| 2007/0020669 A1 | 1/2007 | Olof |
| 2007/0026430 A1 | 2/2007 | Andersen et al. |
| 2007/0172873 A1 | 7/2007 | Brenner et al. |
| 2008/0071071 A1 | 3/2008 | LaBaer et al. |
| 2008/0108804 A1 | 5/2008 | Hayashizaki et al. |
| 2008/0220981 A1 | 9/2008 | McGregor |
| 2008/0293591 A1 | 11/2008 | Taussig et al. |
| 2008/0312103 A1 | 12/2008 | Nemoto et al. |
| 2009/0280487 A1 | 11/2009 | Hung et al. |
| 2009/0291854 A1 | 11/2009 | Weisinger-Mayr et al. |
| 2010/0069263 A1 | 3/2010 | Shendure et al. |
| 2010/0099103 A1 | 4/2010 | Hsieh et al. |
| 2010/0113302 A1 | 6/2010 | Williams |
| 2010/0159446 A1* | 6/2010 | Haff .................. C12Q 1/485 435/6.11 |
| 2010/0173384 A1 | 7/2010 | Johnsson et al. |
| 2010/0184614 A1 | 7/2010 | Ye et al. |
| 2011/0245101 A1 | 10/2011 | Chee et al. |
| 2011/0245111 A1 | 10/2011 | Chee |
| 2012/0065081 A1 | 3/2012 | Chee |
| 2012/0129248 A1 | 5/2012 | Chee et al. |
| 2012/0195810 A1 | 8/2012 | Cohen |
| 2012/0258871 A1 | 10/2012 | Kozlov et al. |
| 2012/0270748 A1 | 10/2012 | Chee et al. |
| 2013/0096033 A1 | 4/2013 | Routenberg |
| 2013/0109595 A1 | 5/2013 | Routenberg |
| 2013/0296174 A1 | 11/2013 | Peumans |
| 2015/0087027 A1 | 3/2015 | Makarov |
| 2016/0024576 A1 | 1/2016 | Chee |
| 2016/0333403 A1 | 11/2016 | Chee |
| 2017/0058339 A1 | 3/2017 | Chee |
| 2017/0058340 A1 | 3/2017 | Chee |
| 2017/0058345 A1 | 3/2017 | Chee |
| 2017/0088881 A1 | 3/2017 | Chee |

FOREIGN PATENT DOCUMENTS

| | | |
|---|---|---|
| WO | WO 2003/010176 | 2/2003 |
| WO | WO 2004/028955 | 4/2004 |
| WO | WO 2005/026387 | 3/2005 |
| WO | WO 2006/117541 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/145612 | 12/2007 |
| WO | WO 2009/032167 | 3/2009 |
| WO | WO 2010/019826 | 2/2010 |
| WO | WO 2010/027870 | 3/2010 |
| WO | WO 2010/127186 | 11/2010 |
| WO | WO 2011/014879 | 2/2011 |
| WO | WO 2011/071943 | 6/2011 |
| WO | WO 2011/127006 | 10/2011 |
| WO | WO 2011/127099 | 10/2011 |
| WO | WO 2012/022975 | 2/2012 |
| WO | WO-2012/071428 | 5/2012 |
| WO | WO 2012/139110 | 10/2012 |
| WO | WO/2014/210223 | 12/2014 |
| WO | WO/2014/210225 | 12/2014 |

OTHER PUBLICATIONS

Non-final Office Action in U.S. Appl. No. 14/723,332, dated Feb. 23, 2016.
Final Office Action in U.S. Appl. No. 14/723,332, dated Nov. 29, 2016.
Non-final Office Action in U.S. Appl. No. 14/723,332, dated Mar. 28, 2017.
Non-final Office Action in U.S. Appl. No. 15/224,253, dated Dec. 9, 2016.
Non-final Office Action in U.S. Appl. No. 15/224,253, dated May 18, 2017.
Final Office Action in U.S. Appl. No. 15/224,253, dated Jul. 3, 2017.
Office Action for U.S. Appl. No. 13/388,229, dated Dec. 24, 2012.
International Search Report and Written Opinion for PCT/US2010/033064, dated Jul. 30, 2010.
International Preliminary Report on Patentability Chapter I for PCT/US2010/033064, dated Nov. 1, 2011.
International Search Report and Written Opinion for PCT/US2010/044134, dated Mar. 18, 2011.
International Preliminary Report on Patentability Chapter I for PCT/US2010/044134, dated Jan. 31, 2012.
Patent Examination Report No. 1 for AU 2010278710, dated Feb. 11, 2014.
Communication Pursuant to Art. 94(3) EPC for EP 10747097.3-1405, dated Jul. 26, 2013.
Restriction Requirement for U.S. Appl. No. 13/514,045, dated Nov. 23, 2012.
Response to Restriction Requirement for U.S. Appl. No. 13/514,045, filed Dec. 19, 2012.
Office Action for U.S. Appl. No. 13/514,045, dated Feb. 21, 2013.
Response to Office Action for U.S. Appl. No. 13/514,045, filed Jun. 17, 2013.
Response to Office Action for U.S. Appl. No. 13/514,045, filed Jun. 27, 2013.
Final Office Action for U.S. Appl. No. 13/514,045, dated Oct. 18, 2013.
International Search Report and Written Opinion for PCT/US2010/059327, dated Mar. 29, 2011.
International Preliminary Report on Patentability Chapter I for PCT/US2010/059327, dated Jun. 12, 2012.
Patent Examination Report No. 1 for AU 2010328226, dated May 9, 2013.
First Office Action for CN 201080055351.2, dated Jul. 23, 2013.
Supplemental European Search Report for EP 10836568.5-1403, dated Feb. 13, 2013.
Response to Supplemental European Search Report for EP 10836568.5-1403, filed Sep. 10, 2013.
Communication Pursuant to Art. 94(3) EPC for EP 10836568.5-1403, dated Mar. 12, 2014.
First Examination Report for EP 10836568.5-1403, dated Oct. 1, 2013.
Response to First Examination Report for EP 10836568.5-1403, filed Feb. 17, 2014.

(56) References Cited

OTHER PUBLICATIONS

Response to Examination Report for EP 10836568.5-1403, dated Jul. 10, 2014.
Restriction Requirement for U.S. Appl. No. 13/080,616, dated Dec. 17, 2013.
Response to Restriction Requirement for U.S. Appl. No. 13/080,616, filed Jan. 16, 2014.
Office Action for U.S. Appl. No. 13/080,616, dated Apr. 9, 2014.
Response to Office Action for U.S. Appl. No. 13/080,616, filed Aug. 11, 2014.
Final Office Action for U.S. Appl. No. 13/080,616, dated Oct. 21, 2014.
Response to final Office Action for U.S. Appl. No. 13/080,616, filed Feb. 23, 2015.
Advisory Action for U.S. Appl. No. 13/080,616, dated Mar. 17, 2015.
International Search Report and Written Opinion for PCT/US2011/031308, dated Jun. 7, 2011.
International Preliminary Report on Patentability Chapter I for PCT/US2011/031308, dated Oct. 9, 2012.
Patent Examination Report No. 1 for AU 2011237729, dated Jul. 9, 2013.
Response to Patent Examination Report No. 1 for AU 2011237729, filed Mar. 3, 2014.
Patent Examination Report No. 1 for AU 2014203638, dated Oct. 1, 2015.
Office Action for CA 2794522, dated May 22, 2014.
Response to Office Action for CA 2794522, dated Sep. 17, 2014.
Voluntary Amendment and Observation for CN 201180017696.3, filed Jul. 25, 2013.
First Examination Report for CN 201180017696.3, dated Oct. 18, 2013.
Second Examination Report for CN 201180017696.3, dated Jul. 3, 2014.
Response to First Examination Report for CN 201180017696.3, filed Mar. 3, 2014.
Response to Second Examination Report for CN 201180017696.3, filed Sep. 17, 2014.
Third Examination Report for CN 201180017696.3, dated Jan. 27, 2015.
Response to Third Examination Report for CN 201180017696.3, filed Apr. 13, 2015.
Rule 161/162 Communication for EP 11766613.1, dated Nov. 14, 2012.
Response to Rule 161/162 Communication for EP 11766613.1, filed May 17, 2013.
European Search Report for EP 11766613.1, dated Jan. 15, 2014.
Response to European Search Report for EP 11766613.1, filed Jul. 11, 2014.
European Examination Report for EP 11766613.1, dated Aug. 22, 2014.
Response to European Examination Report for EP 11766613.1, filed Jan. 8, 2015.
Office Action for U.S. Appl. No. 13/079,878, dated Aug. 13, 2012.
International Search Report and Written Opinion for PCT/US2011/031163, dated May 23, 2011.
International Preliminary Report on Patentability Chapter I for PCT/US2011/031163, dated Oct. 9, 2012.
Restriction Requirement for U.S. Appl. No. 13/442,637, dated May 17, 2012.
Response to Restriction Requirement for U.S. Appl. No. 13/442,637, filed Jun. 5, 2012.
Supplemental Response and Amendment for U.S. Appl. No. 13/442,637, filed Jun. 6, 2012.
Office Action for U.S. Appl. No. 13/442,637, dated Aug. 9, 2012.
Response to Office Action for U.S. Appl. No. 13/442,637, filed Oct. 9, 2012.
Final Office Action for U.S. Appl. No. 13/442,637, dated Dec. 20, 2012.
Response to Final Office Action for U.S. Appl. No. 13/442,637, filed Mar. 20, 2013.
Advisory Action for U.S. Appl. No. 13/442,637, dated Apr. 1, 2013.
Preliminary Amendment and remarks with filing of RCE for U.S. Appl. No. 13/442,637, filed Apr. 17, 2013.
Office Action for U.S. Appl. No. 13/442,637, dated Jan. 22, 2015.
Office Action for U.S. Appl. No. 13/442,637, dated Oct. 8, 2015.
Preliminary Amendment for U.S. Appl. No. 14/068,921, filed Nov. 22, 2013.
Non-final Office Action in U.S. Appl. No. 14/068,921, dated Jun. 29, 2015.
Final Office Action in U.S. Appl. No. 14/068,921, dated Mar. 1, 2016.
Non-final Office Action in U.S. Appl. No. 14/068,921, dated May 8, 2017.
International Search Report and Written Opinion for PCT/US20120/032759, dated Sep. 28, 2012.
International Preliminary Report on Patentability Chapter I for PCT/US2012/032759, dated Oct. 8, 2013.
Invitation to Pay Additional Fees and, Where Applicable, Protest Fee for PCT/US2012/032759, dated Jul. 16, 2012.
Extended European Search Report for EP 12767937.1-1403, dated Nov. 18, 2014.
Extended European Search Report for EP 16183356.1, dated Apr. 24, 2017.
International Search Report and Written Opinion of PCT/US14/29691, dated Aug. 19, 2014.
Restriction Requirement in U.S. Appl. No. 14/776,537, dated Jan. 6, 2017.
Non-final Office Action in U.S. Appl. No. 14/776,537, dated May 2, 2017.
First Examination Report in CN 201480028069.3, dated Aug. 26, 2016 (Including English translation).
Second Examination Report in CN 201480028069.3, dated Jul. 10, 2017 (Including English translation).
Extended European Search Report for EP 14765026.1, dated Sep. 26, 2016.
International Search Report and Written Opinion of PCT/US14/44191, dated Nov. 7, 2014.
Non-final Office Action in U.S. Appl. No. 14/900,602, dated Jan. 9, 2017.
Extended European Search Report for EP 14816674.7, dated Feb. 3, 2017.
International Search Report and Written Opinion of PCT/US14/44196, dated Nov. 7, 2014.
Non-final Office Action in U.S. Appl. No. 14/900,604, dated Feb. 7, 2017.
Extended European Search Report for EP 14818012.8, dated Feb. 3, 2017.
International Search Report and Written Opinion of PCT/US14/64588, dated Mar. 11, 2015.
Valencia et al., "mRNA-display-based selections for proteins with desired functions: A protease-substrate case study," Biotechnology Progress, 2008, 24(3): 561-569.
Anderson et al., "Microarrayed Compound Screening to Identify Activators and Inhibitors of AMP-Activated Protein Kinase," J. of Biomolecular Screening (2004) 9:112 POI: 0.1177/1087057103260592.
Angenendt et al., "Cell-free expression and functional assay in a nanowell chip format," Analytical Chemistry (2004) 76(7):1844-49.
Angenendt et al.,"Generation of High Density Protein Microarrays by Cell-free in Situ Expression of Unpurified PCR Products," Molecular and Cellular Proteomics (2006) Ch. 5.9, pp. 1658-66.
Atkinson, Overview of Translation: Lecture Manuscript, U of Texas (2000) pp. 6.1-6.8.
Blokzijl et al., "Profiling protein expression and interactions: proximity ligation as a tool for personalized medicine," J Intern Med (2010) 268:232-245.
Burns et al., "Well-less, gel-permeation formats for ultra-HTS," DDT (2001) 6(12):S40-S47.
Carlson et al., "Formylglycine-generating Enzyme," J. of Biological Chemistry (2008) 283(29):20117-125.
Cha et al., "Specificity, Efficiency and Fidelity of PCR," Genome Res. (1993) 3:518-29.

(56) References Cited

OTHER PUBLICATIONS

Chandra et al., "Cell-free synthesis-based protein microarrays and their applications," Proteomics ePub (2009) 5(6):717-30.
Chatterjee et al., "Protein Microarray On-Demand: A Novel Protein Microarray System," PLos One (2008) 3(9):e3265.
Chen et al., "DNA hybridization detection in a microfluidic Channel using two fluorescently labelled nucleic acid probes", Biosensors and Bioelectronics (2008) 23:1878-1882.
Cheng et al., "Sensitive Detection of Small Molecules by Competitive Immunomagnetic-Proximity Ligation Assay," Anal Chem (2012) 84:2129-2132.
Condina et al., "A sensitive magnetic bead method for the detection and identification of tyrosine phosphorylation in proteins by MALDI-TOF/TOF MS," Proteomics (2009) 9:3047-3057.
Cujec et al. "Selection of v-abl tyrosine kinase substate sequences from randomnized peptide and cellular proteomic libraries using mRNA display," Chemistry and Biology (2002) 9:253-264.
Darmanis, et al.,"ProteinSeq: High-Performance Proteomic Analyses by Proximity, Ligation and Next Generation Sequencing", PLos One (2011) 6(9):e25583 doi1 0.1371/journal .pone.0025583 20 1.
Eldridge et al. "An in vitro selection strategy for conferring protease resistance to ligand binding peptides," Protein Eng Des Sel (2009) 22(11):691-698.
Ellington et al., "Antibody-based protein multiplex platforms: technical and operational challenges," Clin Chem (2010) 56(2):186-193.
Flanigon et al., "Multiplex protein detection with DNA readout via mass spectrometry," N Biotechnol (2013) 30(2):153-158.
Fredriksson et al., "Protein detection using proximity-dependent DNA ligation assays," Nature Biotech. (2002) 20:473-77.
Fredriksson et al., "Multiplexed protein detection by proximity ligation for cancer detection," Nature Methods (2007) 4(4):327-29.
Fredriksson et al., "Multiplexed proximity ligation assays to profile putative plasma biomarkers relevant to pancreatic and ovarian cancer," Clin. Chem. (2008) 5(3): 582-89.
Frese et al., "Formylglycine Aldehyde Tag-Protein Engineering through a Novel Post-translational Modification," ChemBioChem (2009) 10:425-27.
Fu et al., "Counting individual DNA molecules by the stochastic attachment of diverse labels," PNAS (2011) 108:9026-9031.
Gu et al., "Protein tag-mediated conjugation of oligonucleotides to recombinant affinity binders for proximity ligation," N Biotechnol (2013) 30(2):144-152.
Hammond et al., "Profiling cellular protein complexes by proximity ligation with dual tag microarray readout," (2012) 7(7):e40405.
He et al., "In situ synthesis of protein arrays," Current Opinion in Biotechnology (2008) 19:4-9.
He et al., "In situ synthesis of protein arrays," Current Opinion in Biotechnology (2008)19:4-9 Supplementary figures.
He, "Cell-free protein synthesis: applications in proteomics and biotechnology," (2008) New Biotechnology 25:126-132.
He et al., "Printing protein arrays from DNA arrays," Nature Methods (2008) 5:175-77.
Hedskog et al., "Dynamics of HIV-1 Quasispecies during Antiviral Treatment Dissected using Ultra-Deep Pyrosequencing," PLoS One (2010) 5(7)e11345.
Hendrickson et al., "High sensitivity multianalyte immunoassay using covalent DNA-labeled antibodies and polymerase chain reaction," Nucl. Acid Res. (1995) 23(9):522-29.
Hiatt et al., "Parallel, tag-directed assembly of locally-derived short sequence reads," Nature Methods (2010) 7(2):119-25.
Mir et al., "Sequencing by cyclic ligation and cleavage (CycLiC) directly on a microarray captured template," Nucleic Acids Research (2009) 37(1):e5-1.
Kozlov et al., "A Method for Rapid Protease Substrate Evaluation and Optimization," Comb. Chem. and High Throughput (2006) 9:481-87.
Kozlov et al., "A High-Complexity Multiplexed Solution-Phase Assay for Profiling Protease Activity on Microarrays," Comb. Chem. and High Throughput (2008) 11:24-35.

Kozlov et al., "A Highly Scalable Peptide-Based Assay System for Proteomics," PLoS ONE (2012) 7(6):e37441.
Kurz et al., "cDNA-Protein Fusions: Covalent Protein-Gene Conjugates for the In Vitro Selection of Peptides and Proteins," ChemBioChem (2001) 2:666-72.
Larman et al., "Autoantigen discovery with a synthetic human peptidome", Nature Biotechnology (2011) doi:1 0.1038/nbt.1856.
Lundberg et al., "Multiplexed homogeneous proximity ligation assays for high-throughput protein biomarker research in serological material," Mol Cell Proteomics (2011) 10(4):M110.004978.
Lundberg et al.,"Homogeneous antibody-based proximity extension assays provide sensitive and specific detection of low-abundant proteins in human blood", Nucleic Acids Res.(2011) 39(15):e1 02 (Abstract).
Mizusawa et al., "A bacteriophage lambda vector for cloning with BamHI and Sau3A," Gene (1982) 20:317-322.
NG et al., "Massively parallel sequencing and rare disease," Human Molec. Genetics (2010) 19(2):R119-R124.
Niemeyer, "The developments of semisynthetic DNA/protein conjugates," Trends Biotechnol (2002) 20(9):395-401.
Oleinikov et al. "Self-assembling protein arrays using electronic semiconductor microchips and in vitro translation," Journal of Proteome Research (2003) 2:313-319.
Osada et al., "Epitope mapping using ribosome display in a resconstituted cell-free protein synthesis system," Journal of Biochemistry, 2009, 145(5):693-700.
O'Shannessy et al., "Detection and Quantitation of Hexa-Histidine-Tagged recombinant proteins on western blots and by a surface plasmon resonance biosensor technique," Analytical Biochemistry (1995) 229:119-124.
Proseek® Multiplex 96x96 User Manual (2013) Olink Bioscience, Uppsala, Sweden, 20 pages.
Ramachandran et al., "Next-generation high-density self-assembling functional protein arrays," Nature Methods (2008) 5(6):535-38.
Roberts et al., "RNA-peptide fusions for the in vitro selection of peptides and proteins," PNAS USA(1997) 94:12297-302.
Rouillard et al., "OligoArray 2.0: design of oligonucleotide probes for DNA microarrays using a thermodynamic approach," Nuc. Acid Research (2003) 31 (12):3057-62.
Rountenberg et al., "Microfluidic probe: a new tool for integrating microfluidic environments and electronic wafer-probing," Lab Chip, Oct. 29, 2009, 10: 123-127.
Rush et al., "New Aldehyde Tag Sequences Identified by Screening Formylglycine Generating Enzymes in Vitro and in Vivo," J. of American Chemical Society (2008) 130: 12240-41.
Rush et al., "New Aldehyde Tag Sequences Identified by Screening Formylglycine Generating Enzymes in Vitro and in Vivo," J. of American Chemical Society (2008) 130: 12240-41 (2008) Supplement.
Schmitt et al. , "Detection of ultra-rare mutations by next-generation sequencing," PNAS (2012) 109:14508-14523.
Sergeeva et al., "Display technologies: Application for the discovery of drug and gene delivery agents," Advanced Drug Delivery Reviews (2006) 58(15):1622-1654.
Shoemaker et al., "Quantitative phenotypic analysis of yeast deletion mutants using a highly parallel molecular bar-coding strategy," Nature genetics (1996) 14:450-456.
Shults et al., "A multiplexed protein kinase assay," Chem Bio Chem (2007) 8:933-942.
Tolbert et al., "New Methods for Proteomic Research: Preparation of Proteins with N-Terminal Cysteines for Labeling and Conjugation," Angew. Chem. Int. Ed. (2002) 41 (12):2171-74.
Takahashi et al., "In Vitro Selection of Protein and Peptide Libraries Using mRNA Display," Nucleic Acid and Peptide Aptamers: Methods and Protocols (2009) 535:293-314 (Ch.17).
Vogelstein et al., "Digital PCR," PNAS USA (1999) 96:9236-41.
Waichman et al., "Functional Immobilization and Patterning of Proteins by an Enzymatic Transfer Reaction", Anal. Chem. (2010) 82:1478-85.
Weichhart et al., "Functional selection of vaccine candidate peptides from *Staphylococcus aureus* whole-genome expression libraries in vitro," Infection and Immunity, 2003, 71(8):4333-4641.

(56) References Cited

OTHER PUBLICATIONS

Wong et al. "Direct Site-Selective Covalent Protein Immobilization Catalyzed by a Phosphopantetheinyl Transferase," J. Am. Chem Soc. (2008) 130:12456-64.

Worthington et al., "Cloning of random oligonucleotides to create single-insert plasmid libraries," Analyt. Biochem (2001) 294:169-175.

Xiao et al., "Direct determination of haplotypes from single DNA molecules," Nature Methods(2009) 6(3):199-01.

Yin et al., "Genetically encoded short peptide tag for versatile protein labeling by Sfp phosphopantetheinyl transferase," PNAS (2005) 102(44):15815-20.

Yonezawa et al., "DNA display for in vitro selection of diverse peptide libraries", Nucleic Acids Research (2003) 31(19):e118.

Zhang et al., "Assembling DNA through Affinity Binding to Achieve Ultrasensitive Protein Detection," Angew Chem Int Ed (2013) 52:2-10.

Zhang et al., "Binding-induced DNA assembly and its application to yoctomole detection of proteins," Anal Chem (2012) 84(2):877-884.

Zhou et al., "Genetically Encoded Short Peptide Tags for Orthogonal Protein Labeling by Sfp and AcpS Phosphopentetheinyl Transferases," ACS Chemical Biology (2007) 2(5): 337-346.

Zlobec et al., "Next-generation tissue microarray (ngTMA) increases the quality of biomarker studies: an example using CD3, CD8, and CD45RO in the tumor microenvironment of six different solid tumor types," Journal of Translational Medicine (2013) 11:104.

Notice of Preliminary Rejection for KR 10-2012-7029015, dated Sep. 28, 2017, 10 pages (Including English translation).

Communication Pursuant to Article 94(3) EPC, dated Aug. 18, 2017, 8 pages.

Examiner's report for CA 2,794,522, dated Nov. 2, 2017, 4 pages.

Notice of Allowance for U.S. Appl. No. 14/900,602, dated Sep. 7, 2017, 9 pages.

Notice of Allowance for U.S. Appl. No. 14/900,604, dated Sep. 8, 2017, 9 pages.

Notice of Allowance for U.S. Appl. No. 14/900,604, dated Dec. 14, 2017, 2 pages.

Response to Non-final Rejection for U.S. Appl. No. 14/068,921, dated Oct. 9, 2017, 12 pages.

Notice of Allowance for U.S. Appl. No. 14/068,921, dated Dec. 21, 2017, 7 pages.

Communication for EP 16183356.1, dated Jan. 20, 2017, 9 pages.

Communication pursuant to Article 94(3) EPC for EP 16 183 356.1, dated Dec. 13, 2017, 5 pages.

Pouchain et al., "A 10,000 member PNA-encoded peptide library for profiling tyrosine kinases," ACS Chemical Biology 2(12):810-818.

* cited by examiner

OR

OR

A.

B.

C.

D.

A.

B.

C.

SEQUENCE LISTING

<160> NUMBER OF SEQ ID NOS: 9

<210> SEQ ID NO 1
<211> LENGTH: 9
<212> TYPE: PRT

-continued

<213> ORGANISM: Artificial Sequence
<220> FEATURE:
<223> OTHER INFORMATION: Synthetic construct

<400> SEQUENCE: 1

```
Tyr Pro Tyr Asp Val Pro Asp Tyr Ala
 1               5
```

<210> SEQ ID NO 2
<211> LENGTH: 25
<212> TYPE: PRT
<213> ORGANISM: Borrelia burgdorferi

<400> SEQUENCE: 2

```
Met Lys Lys Asp Asp Gln Ile Ala Ala Ala Ile Ala Leu Arg Gly Met
 1               5                  10                  15

Ala Lys Asp Gly Lys Phe Ala Val Lys
            20                  25
```

<210> SEQ ID NO 3
<211> LENGTH: 6
<212> TYPE: PRT
<213> ORGANISM: Artificial Sequence
<220> FEATURE:
<223> OTHER INFORMATION: Synthetic construct

<400> SEQUENCE: 3

```
Asp Thr Tyr Arg Tyr Ile
 1               5
```

<210> SEQ ID NO 4
<211> LENGTH: 6
<212> TYPE: PRT
<213> ORGANISM: Artificial Sequence
<220> FEATURE:
<223> OTHER INFORMATION: Synthetic construct

<400> SEQUENCE: 4

```
Thr Asp Phe Tyr Leu Lys
 1               5
```

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

```
Glu Lys Gln Leu Ile Ser Glu Glu Asp Leu
 1               5                  10
```

<210> SEQ ID NO 6
<211> LENGTH: 8
<212> TYPE: PRT
<213> ORGANISM: Artificial Sequence
<220> FEATURE:
<223> OTHER INFORMATION: Synthetic construct

<400> SEQUENCE: 6

```
His His His His His His His His
 1               5
```

<210> SEQ ID NO 7
<211> LENGTH: 6
<212> TYPE: PRT

```
<213> ORGANISM: Artificial Sequence
<220> FEATURE:
<223> OTHER INFORMATION: Synthetic construct

<400> SEQUENCE: 7

Glu Tyr Met Pro Met Glu
  1               5

<210> SEQ ID NO 8
<211> LENGTH: 15
<212> TYPE: PRT
<213> ORGANISM: Artificial Sequence
<220> FEATURE:
<223> OTHER INFORMATION: Synthetic construct

<400> SEQUENCE: 8

Gly Leu Asn Asp Ile Phe Glu Ala Gln Lys Ile Glu Gln His Glu
  1               5                  10                  15

<210> SEQ ID NO 9
<211> LENGTH: 5
<212> TYPE: PRT
<213> ORGANISM: Artificial Sequence
<220> FEATURE:
<223> OTHER INFORMATION: Synthetic construct

<400> SEQUENCE: 9

Asp Asp Asp Asp Lys
  1               5
```

POLYNUCLEOTIDE CONJUGATES AND METHODS FOR ANALYTE DETECTION

CROSS-REFERENCE TO RELATED APPLICATION

This application is a national phase of International Application No. PCT/US2014/064588, filed Nov. 7, 2014, which claims benefit of priority to U.S. Provisional Patent Application Ser. No. 61/902,105, filed Nov. 8, 2013, entitled "Polynucleotide Conjugates and Methods for Analyte Detection," the disclosures of which are incorporated by reference herein in their entireties for all purposes.

STATEMENT REGARDING FEDERALLY SPONSORED RESEARCH OR DEVELOPMENT

This invention was made with the support by the National Institutes of Health Grant No. GM104031. The U.S. government may have certain rights.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 699932000600SeqList.txt, date recorded: May 6, 2016, size: 2,021 bytes).

TECHNICAL FIELD

The present disclosure generally relates to polynucleotide conjugates and methods of using the same for analyte detection and analysis. In particular, the present disclosure relates to antibody detection and analysis, for example, in a biological sample.

BACKGROUND

In the following discussion, certain articles and methods are described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Comprehensive gene expression analysis and protein analysis have been useful tools in understanding mechanisms of biology. The advent of DNA microarrays allowed the study of a larger number of labeled molecules than ever before, enabled by the specificity of nucleic acid hybridization. Due to non-specific hybridization of similar nucleic acids, DNA microarray-based methods can have small dynamic ranges and high background.

Peptide or protein arrays enable high-throughput screening of compounds that may interact with one or more of the peptides or proteins, and are useful in various applications including basic scientific research and drug discovery. For example, an array of peptide or protein molecules potentially suitable as modulators for a particular biological receptor may be screened with respect to that receptor. However, peptide or protein arrays can be difficult to manufacture, and the screening of arrayed peptides or proteins generally may be carried out against only relatively few labeled molecules at a time.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, provided herein is a pair of polypeptide-polynucleotide conjugates. The pair comprises a first polypeptide-polynucleotide conjugate comprising: (a) a first polypeptide comprising a first epitope for specific binding of an antibody or antigen binding fragment thereof; and (b) a first polynucleotide comprising a first identifying sequence that identifies the first polypeptide, a first engaging sequence, and optionally a first primer sequence. The pair further comprises a second polypeptide-polynucleotide conjugate comprising: (a) a second polypeptide comprising a second epitope for specific binding of the antibody or antigen binding fragment thereof; and (b) a second polynucleotide comprising a second identifying sequence that identifies the second polypeptide, a second engaging sequence, and optionally a second primer sequence. In one embodiment, the first and second engaging sequences are capable of engaging the first and second polynucleotides, and thereby engaging the first and second polypeptide-polynucleotide conjugates.

In any of the present embodiments or combinations thereof, the first engaging sequence can comprise a sequence hybridizable to the second engaging sequence, and/or the second engaging sequence comprises a sequence hybridizable to the first engaging sequence. In some aspects, the first engaging sequence comprises a sequence complementary to all or a portion of the second engaging sequence, and/or the second engaging sequence comprises a sequence complementary to all or a portion of the first engaging sequence.

In any of the present embodiments or combinations thereof, each of the first and second polypeptides can further comprise a tag. In one aspect, the tag is common between the first and second polypeptides. In another aspect, the tag is at the C-terminus or the N-terminus of the first or second polypeptide. In some embodiments, the tag comprises an affinity tag capable of specific binding by a capture agent. In other embodiments, the tag further comprises a purification tag for purification of the pair. In one aspect, the purification tag comprises a polynucleotide sequence.

In any of the preceding embodiments, the first or second polypeptide-polynucleotide conjugate can further comprise an affinity tag capable of specific binding by a capture agent. The affinity tag can be linked to or comprised in any portion of the polypeptide-polynucleotide conjugate, for example, the polypeptide portion, or the polynucleotide portion including the primer sequence. In one aspect, the capture agent is immobilized on a substrate, for example, a substrate comprising a microarray and/or a bead. In any of the preceding embodiments, the first or second polypeptide-polynucleotide conjugate can be immobilized on a substrate, e.g., a substrate comprising a microarray and/or a bead.

In any of the preceding embodiments, the first or second polypeptide-polynucleotide conjugate can further comprise a purification tag for purification of the first or second polypeptide-polynucleotide conjugate or the pair. In one aspect, the purification tag comprises a polynucleotide sequence.

In some aspects, the first polypeptide is conjugated to a portion substantially at the 5' of the first polynucleotide, and the second polypeptide is conjugated to a portion substantially at the 5' of the second polynucleotide. In other aspects, the first polypeptide is conjugated to the 5' end of the first polynucleotide, and the second polypeptide is conjugated to the 5' end of the second polynucleotide. In yet other aspects, the first primer sequence, the first identifying sequence that identifies the first polypeptide, and the first engaging sequence are arranged in the 5' to 3' direction in the first polynucleotide. In some aspects, the second primer sequence, the second identifying sequence that identifies the second polypeptide, and the second engaging sequence are arranged in the 5' to 3' direction in the second polynucleotide.

In any of the preceding embodiments, the first and second epitopes for specific binding of the antibody or antigen binding fragment thereof can be the same. In one aspect, the first and second epitopes specifically bind to an IgA, IgD, IgE, IgG, IgM, or IgY antibody or antigen binding fragment thereof. In other aspects, the first and second epitopes specifically bind to a bivalent antibody or a multivalent antibody or antigen binding fragment thereof. In still other aspects, the first and second epitopes specifically bind to a bispecific antibody or a diabody or antigen binding fragment thereof, and the first and second epitopes are different.

In any of the preceding embodiments, the first and/or second epitopes of the polypeptide-polynucleotide conjugate pair can be associated with a condition or a disease, for example, an infection, an infectious disease, a cancer, an autoimmune disease, an immunodeficiency, an allergy, or an inflammation. In one aspect, the condition or disease is a *Borrelia* infection or Lyme disease. In one embodiment, the *Borrelia* infection or Lyme disease comprises infection by *Borrelia burgdorferi, Borrelia afzelli,* or *Borrelia garinii.*

In certain aspects, provided herein is a set of polypeptide-polynucleotide conjugates, the set comprising a plurality of the pair of first and second polypeptide-polynucleotide conjugates according to any of the preceding embodiments. In one aspect, the first polypeptide-polynucleotide conjugate of each of the polypeptide-polynucleotide conjugate pairs is immobilized on a substrate. In another aspect, the second polypeptide-polynucleotide conjugate of each of the polypeptide-polynucleotide conjugate pairs is not immobilized on the substrate, and is instead, e.g., provided in solution.

In one embodiment, a method for analyzing an antibody or antigen binding fragment thereof in a sample is disclosed. The method comprises immobilizing a first polypeptide-polynucleotide conjugate on a substrate. In one aspect, the first polypeptide-polynucleotide conjugate comprises: (a) a first polypeptide comprising a first epitope for specific binding of an antibody or antigen binding fragment thereof; and (b) a first polynucleotide comprising a first identifying sequence that identifies the first polypeptide, a first engaging sequence, and optionally a first primer sequence. The method further comprises contacting the substrate having the immobilized first polypeptide-polynucleotide conjugate with a sample containing or suspected of containing the antibody or antigen binding fragment thereof, whereby the first epitope specifically binds to the antibody or antigen binding fragment thereof in the sample. The method further comprises contacting the substrate having the immobilized first polypeptide-polynucleotide conjugate with a second polypeptide-polynucleotide conjugate, which comprises: (a) a second polypeptide comprising a second epitope for specific binding of the antibody or antigen binding fragment thereof; and (b) a second polynucleotide comprising a second identifying sequence that identifies the second polypeptide, a second engaging sequence, and optionally a second primer sequence. In some aspects, the second epitope specifically binds to the antibody or antigen binding fragment thereof specifically bound to the first epitope, and the first and second polynucleotides are therefore engaged via the first and second engaging sequences. The method further comprises analyzing the first and/or second polynucleotides engaged via the first and second engaging sequences, wherein the analyzing step indicates the presence, absence, and/or amount of the antibody or antigen binding fragment thereof in the sample.

In any of the preceding embodiments, the substrate can comprise a microarray and/or a bead. In one aspect, the first engaging sequence comprises a sequence hybridizable to the second engaging sequence, and/or the second engaging sequence comprises a sequence hybridizable to the first engaging sequence. In another aspect, the first engaging sequence comprises a sequence complementary to all or a portion of the second engaging sequence, and/or the second engaging sequence comprises a sequence complementary to all or a portion of the first engaging sequence.

In any of the preceding embodiments, the analyzing step can comprise extending both of the first and second polynucleotides, or extending only one of the first and second polynucleotides while the other is blocked from being extended by a polymerase. In one aspect, extending the first and second polynucleotides generates a double-stranded polynucleotide comprising the sequences of the first primer, the first identifying sequence, the first and second engaging sequences, the second identifying sequence, and the second primer.

In any of the preceding embodiments, the analyzing step can comprise determining the sequence of all or a portion of the first and/or second polynucleotide. In one aspect, the analyzing step comprises sequencing all or a portion of the first and/or second polynucleotide. In one aspect, a polynucleotide comprising the sequences of the first primer, the first identifying sequence, the first and second engaging sequences, the second identifying sequence, and the second primer, is sequenced. In some embodiments, the sequencing is performed using the first primer and/or the second primer as the sequencing primer(s). In some aspects, the sequencing is performed by digital sequencing, high-throughput sequencing, parallel sequencing, qPCR with pair-specific primers, and/or high-throughput qPCR (e.g., Biomark™ from Fluidigm Corp., or RainDance ThunderStorm™ from RainDance Technologies). In other embodiments, sequence determination is carried out without amplification of the sequence of all or a portion of the first and/or second polynucleotide, for example, by mass spectrometry. In one aspect, sequence determination is performed by using labeled oligonucleotide probes complementary to the first or second polynucleotide or to the primer extension product. In another aspect, the first or second polynucleotide or the primer extension product is labeled, and the label results in detectable signals indicative of the presence, amount, and/or sequence of the labeled polynucleotide. For example, enzymatic amplification or quantum dots (e.g., qDots®, Life Technologies) can be used.

In any of the preceding embodiments, the analyzing step can comprise amplifying all or a portion of the first and/or second polynucleotide. For example, a polynucleotide comprising the sequences of the first primer, the first identifying sequence, the first and second engaging sequences, the second identifying sequence, and the second primer, is amplified. In some aspects, the amplifying step is carried out by PCR or in vitro transcription.

In any of the preceding embodiments, each of the first and second polypeptides can further comprise a tag. In one aspect, the tag is common between the first and second polypeptides. In another aspect, the tag is at the C-terminus or N-terminus of the first or second polypeptide. In another aspect, the tag comprises an affinity tag capable of specific binding by a capture agent. In yet another aspect, the first or second polypeptide-polynucleotide conjugate further comprises an affinity tag capable of specific binding by a capture agent. In one embodiment, the capture agent is immobilized on a substrate, for example, a substrate comprising a microarray and/or a bead.

In any of the preceding embodiments, the first and/or second polypeptide-polynucleotide conjugates can each comprise a purification tag for purification of the polypeptide-polynucleotide conjugate. In one aspect, the purification tag comprises a polynucleotide sequence.

In any of the preceding embodiments, the first polypeptide can be conjugated to a portion substantially at the 5' of the first polynucleotide, and the second polypeptide is conjugated to a portion substantially at the 5' of the second polynucleotide. In one aspect, the first polypeptide is conjugated to the 5' end of the first polynucleotide, and the second polypeptide is conjugated to the 5' end of the second polynucleotide. In another aspect, the first primer sequence, the first identifying sequence that identifies the first polypeptide, and the first engaging sequence are arranged in the 5' to 3' direction in the first polynucleotide. In still another aspect, the second primer sequence, the second identifying sequence that identifies the second polypeptide, and the second engaging sequence are arranged in the 5' to 3' direction in the second polynucleotide.

In any of the preceding embodiments, the first and second epitopes for specific binding of the antibody can be the same. In one aspect, the antibody is an IgA, IgD, IgE, IgG, IgM, or IgY. In another aspect, the antibody is a bivalent antibody or a multivalent antibody. In one aspect, the antibody is a bispecific antibody or a diabody, and the first and second epitopes for specific binding of the antibody are different. In any of the presently disclosed methods, the first and second epitopes can be associated with a condition or a disease, for example, a *Borrelia* infection or Lyme disease (Lyme borreliosis). In one aspect, the *Borrelia* infection or Lyme disease comprises infection by *Borrelia burgdorferi*, *Borrelia afzelii*, or *Borrelia garinii*.

In one embodiment, provided herein is a method for analyzing an antibody or antigen binding fragment thereof in a sample, comprising immobilizing a first polypeptide-polynucleotide conjugate on a substrate. In one aspect, the first polypeptide-polynucleotide conjugate comprises: (a) a first polypeptide comprising a first epitope for specific binding of an antibody or antigen binding fragment thereof; and (b) a first polynucleotide comprising a first identifying sequence that identifies the first polypeptide, a first engaging sequence, and optionally a first primer sequence. The method further comprises providing a second polypeptide-polynucleotide conjugate, which comprises: (a) a second polypeptide comprising a second epitope for specific binding of the antibody or antigen binding fragment thereof; and (b) a second polynucleotide comprising a second identifying sequence that identifies the second polypeptide, a second engaging sequence, and optionally a second primer sequence. In one aspect, the second polypeptide-polynucleotide conjugate forms a complex (a conjugate complex) with the immobilized first polypeptide-polynucleotide conjugate. The method further comprises contacting the substrate having the complex between the first and second polypeptide-polynucleotide conjugates with a sample containing or suspected of containing the antibody or antigen binding fragment thereof, wherein at least one molecule of the second polypeptide-polynucleotide conjugate specifically binds to the antibody or antigen binding fragment thereof specifically bound to the first polypeptide-polynucleotide conjugate, thereby forming a ternary complex. Next, the method further comprises washing the substrate under conditions that allow the release of molecules of the second polypeptide-polynucleotide conjugate that are not specifically bound to the antibody or antigen binding fragment thereof, while maintaining the ternary complex formed by specific binding. The method further comprises providing conditions under which the first and second polynucleotides are engaged via the first and second engaging sequences in the ternary complex formed by specific binding, and analyzing the first and/or second polynucleotides engaged via the first and second engaging sequences, wherein the analysis indicates the presence, absence, and/or amount of the antibody or antigen binding fragment thereof in the sample.

In any of the preceding embodiments, the complex between the first and second polypeptide-polynucleotide conjugates can be formed by hybridization between the first and second polynucleotides. In one aspect, the washing step is performed under conditions that destabilize the hybridization between the first and second polynucleotides, thereby releasing molecules of the second polypeptide-polynucleotide conjugate that are not specifically bound to the antibody or antigen binding fragment thereof. In another aspect, the sequences involved in the hybridization between the first and second polynucleotides comprise one or more cleavable sites. In one embodiment, the sequences involved in the hybridization are cleaved at the one or more cleavable sites before or during the washing step, thereby destabilizing the hybridization between the first and second polynucleotides.

In any of the preceding embodiments, the second polypeptide-polynucleotide conjugate can be kept in physical proximity to the first polypeptide-polynucleotide conjugate by a cleavable linker, before or after the first and second polypeptide-polynucleotide conjugates form the complex (the conjugate complex). In one aspect, the cleavable linker is between the first and second polypeptide-polynucleotide conjugates, or between the second polypeptide-polynucleotide conjugate and the substrate. In one aspect, the cleavable linker is cleaved before or during the washing step, optionally under conditions that destabilize the hybridization between the first and second polynucleotides.

In one aspect, a method of any of the preceding embodiments can further comprise a step of fixing the antibody or antigen-binding fragment thereof in physical proximity to the first polypeptide-polynucleotide conjugate, upon specific binding of the antibody or antigen-binding fragment thereof to the first polypeptide-polynucleotide conjugate. In one embodiment, the fixing step is carried out by cross-linking the antibody or antigen-binding fragment thereof to the specifically bound first polypeptide-polynucleotide conjugate, or by cross-linking the antibody or antigen-binding fragment thereof to the substrate. In one aspect, the second polypeptide-polynucleotide conjugate comprises two second epitopes for specific binding to the antibody or antigen binding fragment thereof, wherein the second polypeptide-polynucleotide conjugate is provided after the fixing step, and wherein the second polypeptide-polynucleotide conjugate displaces the antibody or antigen binding fragment thereof from the first polypeptide-polynucleotide conjugate.

In one aspect, a method of any of the preceding embodiments can further comprise providing a third polypeptide-polynucleotide conjugate. In one aspect, the third conjugate comprises: (1) an antibody portion that specifically binds to the Fc portion of the antibody or antigen binding fragment thereof; and (2) a third polynucleotide that comprises a third primer sequence, a third identifying sequence that identifies the antibody portion, and a third engaging sequence. In one aspect, the first or second polynucleotide is extended by a polymerase after the first and second polynucleotides are engaged, wherein the extended first or second polynucleotide is capable of engaging the third polynucleotide, and wherein the extended first or second polynucleotide is further extended by a polymerase using all or a portion of the third polynucleotide as a template.

In another aspect, disclosed herein is a method for analyzing a plurality of antibodies or antigen binding fragments thereof in a sample, the method comprising: (i) immobilizing a plurality of first polypeptide-polynucleotide conjugates on a substrate, each of the first polypeptide-polynucleotide conjugates comprising: (a) a first polypeptide comprising a first epitope for specific binding of an antibody or antigen binding fragment thereof in a plurality of antibodies or antigen binding fragments thereof; and (b) a first polynucleotide comprising a first primer sequence, a first identifying sequence that identifies the first polypeptide, and a first engaging sequence; (ii) contacting the substrate having the immobilized plurality of first polypeptide-polynucleotide conjugates with a sample containing or suspected of containing at least one of the plurality of antibodies or antigen binding fragments, whereby the at least one antibody or antigen binding fragment in the sample specifically binds to a first epitope of the immobilized plurality of first polypeptide-polynucleotide conjugates; (iii) contacting the substrate having the immobilized plurality of first polypeptide-polynucleotide conjugates with a plurality of second polypeptide-polynucleotide conjugates, each of the second polypeptide-polynucleotide conjugates comprising: (a) a second polypeptide comprising a second epitope for specific binding of an antibody or antigen binding fragment thereof in the plurality of antibodies or antigen binding fragments; and (b) a second polynucleotide comprising a second primer sequence, a second identifying sequence that identifies the second polypeptide, and a second engaging sequence, whereby the at least one antibody or antigen binding fragment specifically bound to the first epitope specifically binds to a second epitope of the plurality of second polypeptide-polynucleotide conjugates, and whereby the first and second polypeptide-polynucleotide conjugates specifically bound to the same antibody or antigen binding fragment are engaged via the first and second engaging sequences; and (iv) analyzing the first and/or second polypeptide-polynucleotide conjugates engaged via the first and second engaging sequences, wherein the analysis in step (iv) indicates the presence, absence and/or amount of the plurality of antibodies or antigen binding fragments thereof in the sample. In one aspect, the plurality of the first epitopes are overlapping epitopes, the plurality of the second epitopes are overlapping epitopes, the plurality of the first polypeptides comprise overlapping epitopes, and/or the plurality of the second polypeptides comprise overlapping epitopes.

In one aspect, the density of the first polypeptide-polynucleotide conjugate molecules immobilized or directly synthesized on the substrate is sufficiently low to substantially reduce or prevent interaction between adjacent first polypeptide-polynucleotide conjugate molecules on the substrate, or to substantially reduce or prevent interaction between the analyte molecule bound by one first polypeptide-polynucleotide conjugate molecule and an adjacent first polypeptide-polynucleotide conjugate molecule on the substrate.

In one aspect, disclosed herein is a method of manufacturing a system for analyzing an antibody or antigen binding fragment thereof, the method comprising: (i) generating an array by immobilizing or directly synthesizing a plurality of first polypeptide-polynucleotide conjugates on a substrate, each first polypeptide-polynucleotide conjugate comprising: (a) a first polypeptide comprising a first epitope for specific binding of an antibody or antigen binding fragment thereof; and (b) a first polynucleotide comprising a first identifying sequence that identifies the first polypeptide, a first engaging sequence, and optionally a first primer sequence; (ii) generating a library comprising a plurality of second polypeptide-polynucleotide conjugates, each second polypeptide-polynucleotide conjugate comprising: (a) a second polypeptide comprising a second epitope for specific binding of an antibody or antigen binding fragment thereof; and (b) a second polynucleotide comprising a second identifying sequence that identifies the second polypeptide, a second engaging sequence, and optionally a second primer sequence, wherein at least one pair of first and second polypeptide-polynucleotide conjugates is capable of specific binding to the same antibody molecule or antigen binding fragment thereof, wherein specific binding of the at least one pair to the same antibody molecule or antigen binding fragment thereof engages the first and second engaging sequences of the at least one pair.

Thus, also disclosed herein is a system, comprising: (i) an array comprising a substrate onto which a plurality of first polypeptide-polynucleotide conjugates are immobilized or directly synthesized in situ, each first polypeptide-polynucleotide conjugate comprising: (a) a first polypeptide comprising a first epitope for specific binding of an antibody or antigen binding fragment thereof; and (b) a first polynucleotide comprising a first identifying sequence that identifies the first polypeptide, a first engaging sequence, and optionally a first primer sequence; (ii) a library comprising a plurality of second polypeptide-polynucleotide conjugates, each second polypeptide-polynucleotide conjugate comprising: (a) a second polypeptide comprising a second epitope for specific binding of an antibody or antigen binding fragment thereof; and (b) a second polynucleotide comprising a second identifying sequence that identifies the second polypeptide, a second engaging sequence, and optionally a second primer sequence. In one aspect, at least one pair of a first polypeptide-polynucleotide conjugate (from the array) and a second polypeptide-polynucleotide conjugate (from the library) is capable of specific binding to the same antibody molecule or antigen binding fragment thereof. In one aspect, specific binding of the at least one pair to the same antibody molecule or antigen binding fragment thereof is capable of engaging the first and second engaging sequences of the at least one pair.

In any of the preceding embodiments, the plurality of first polypeptide-polynucleotide conjugates can be immobilized or directly synthesized on the substrate at a density that substantially reduces or prevents interaction between adjacent first polypeptide-polynucleotide conjugates on the substrate. In one aspect, the method further comprises contacting the array with the library, wherein at least one pair of first and second polypeptide-polynucleotide conjugates forms a conjugate complex. In one embodiment, the conjugate complex is formed by hybridization between the first and second polynucleotides of the at least one pair of first and second polypeptide-polynucleotide conjugates. In one example, the sequences involved in the hybridization between the first and second polynucleotides comprise one or more cleavable sites. In any of the preceding embodiments, the second polypeptide-polynucleotide conjugate of the at least one pair that forms a conjugate complex can be immobilized on the substrate via a cleavable linker. In one aspect, the method further comprises linking the first and second polypeptide-polynucleotide conjugates in the conjugate complex with a cleavable linker.

In any of the preceding embodiments, the method can further comprise providing a third polypeptide-polynucleotide conjugate which comprises: (1) an antibody portion that specifically binds to the Fc portion of the antibody or antigen binding fragment thereof; and (2) a third polynucleotide that comprises a third primer sequence, a third identifying sequence that identifies the antibody portion, and a third engaging sequence, wherein the first or second polynucleotide is capable of being extended by a polymerase after the first and second polynucleotides are engaged, wherein the extended first or second polynucleotide is capable of engaging the third polynucleotide, and wherein the extended first or second polynucleotide is capable of being further extended by a polymerase, for example, using all or a portion of the third polynucleotide as a template.

Thus, also disclosed herein is a set of polypeptide-polynucleotide conjugates, comprising: a first polypeptide-polynucleotide conjugate comprising: (a) a first polypeptide comprising a first epitope for specific binding of an antibody or antigen binding fragment thereof; and (b) a first polynucleotide comprising a first primer sequence, a first identifying sequence that identifies the first polypeptide, and a first engaging sequence; a second polypeptide-polynucleotide conjugate comprising: (a) a second polypeptide comprising a second epitope for specific binding of the antibody or antigen binding fragment thereof; and (b) a second polynucleotide comprising a second identifying sequence that identifies the second polypeptide, a second engaging sequence, and optionally a second primer sequence; and a third polypeptide-polynucleotide conjugate comprising: (a) an antibody portion that specifically binds to the Fc portion of the antibody or antigen binding fragment thereof; and (2) a third polynucleotide that comprises a third identifying sequence that identifies the antibody portion, a third engaging sequence, and optionally a third primer sequence. In one aspect, the first and second engaging sequences are capable of engaging the first and second polynucleotides. In one aspect, the first or second polynucleotide is capable of being extended by a polymerase after the first and second polynucleotides are engaged. In one aspect, the extended first or second polynucleotide is capable of engaging the third polynucleotide, for example, via interaction with the third engaging sequence. In one aspect, the extended first or second polynucleotide is capable of being further extended by a polymerase using all or a portion of the third polynucleotide as a template.

In one aspect, disclosed herein is a pair of polynucleotide conjugates, comprising: a first polynucleotide conjugate comprising: (a) a first binder for specific binding of an analyte; and (b) a first polynucleotide comprising a first primer sequence, a first identifying sequence that identifies the first binder, and a first engaging sequence; and a second polynucleotide conjugate comprising: (a) a second binder for specific binding of the analyte; and (b) a second polynucleotide comprising a second primer sequence, a second identifying sequence that identifies the second binder, and a second engaging sequence, wherein the first and second engaging sequences are capable of engaging the first and second polynucleotides, thereby engaging the first and second polynucleotide conjugates. In one aspect, the first and second binders are the same.

In one aspect, the first engaging sequence comprises a sequence hybridizable to the second engaging sequence, and/or the second engaging sequence comprises a sequence hybridizable to the first engaging sequence. In another aspect, the first engaging sequence comprises a sequence complementary to all or a portion of the second engaging sequence, and/or the second engaging sequence comprises a sequence complementary to all or a portion of the first engaging sequence.

In one aspect, each of the first and second binder further comprises a tag. In one embodiment, the tag is common between the first and second binders. In another embodiment, the tag comprises an affinity tag capable of specific binding by a capture agent. In one aspect, the first or second polynucleotide conjugate further comprises an affinity tag capable of specific binding by a capture agent. In some aspects, the capture agent is immobilized on a substrate, for example, a substrate comprising a microarray and/or a bead. In one aspect, the first or second polynucleotide conjugate is immobilized on a substrate, for example, a substrate comprising a microarray and/or a bead. In one aspect, the tag comprises a purification tag for purification of the pair. In one example, the purification tag comprises a polynucleotide sequence.

In one aspect, the first binder is conjugated to a portion substantially at the 5' of the first polynucleotide, and the second binder is conjugated to a portion substantially at the 5' of the second polynucleotide. In another aspect, the first binder is conjugated to the 5' end of the first polynucleotide, and the second binder is conjugated to the 5' end of the second polynucleotide. In yet another aspect, the first primer sequence, the first identifying sequence that identifies the first polypeptide, and the first engaging sequence are arranged in the 5' to 3' direction in the first polynucleotide, and the second primer sequence, the second identifying sequence that identifies the second polypeptide, and the second engaging sequence are arranged in the 5' to 3' direction in the second polynucleotide.

In one aspect, the first and second binders specifically bind to a bivalent or multivalent analyte. In some embodiments, the first and second binders specifically bind to an analyte that is a nucleic acid, a polysaccharide, a polypeptide, an antibody, a ligand, a receptor, or a T cell receptor.

In any of the preceding embodiments, the first and second binders can specifically bind to an analyte associated with a condition or a disease, for example, an infection or an infectious disease.

In one aspect, disclosed herein is a set of polynucleotide conjugates, the set comprising a plurality of the pairs according to any of the preceding embodiments. In one aspect of a set disclosed herein, the first polynucleotide conjugate of each of the polynucleotide conjugate pairs is immobilized on a substrate. In another aspect, the second polynucleotide conjugate of each of the polynucleotide conjugate pairs is not immobilized on the substrate, and is provided in solution.

In one embodiment, disclosed herein is a method for analyzing an analyte in a sample, comprising: (i) immobilizing a first polynucleotide conjugate on a substrate, the first polynucleotide conjugate comprising: (a) a first binder for specific binding of an analyte; and (b) a first polynucleotide comprising a first identifying sequence that identifies the first binder, a first engaging sequence, and optionally a first primer sequence; (ii) contacting the substrate having the immobilized first polynucleotide conjugate with a sample containing or suspected of containing the analyte, whereby the first binder specifically binds to the analyte in the sample; (iii) contacting the substrate having the immobilized first polynucleotide conjugate with a second polynucleotide conjugate, the second polynucleotide conjugate comprising: (a) a second binder for specific binding of the analyte; and (b) a second polynucleotide comprising a second identifying sequence that identifies the second binder, a second engaging sequence, and optionally a second primer sequence, whereby the second binder specifically binds to the analyte specifically bound to the first binder, and whereby the first and second polynucleotides are engaged via the first and second engaging sequences; and (iv) analyzing the first and/or second polynucleotides engaged via the first and second engaging sequences, wherein the analysis in step (iv) indicates the presence, absence and/or amount of the analyte in the sample. In some aspects, the first and second binders are the same or different.

In certain aspects, the first polynucleotide conjugate comprises one or more first primer sequences. In certain aspects, the second polynucleotide conjugate comprises one or more second primer sequences. In one aspect, the first or second polynucleotide conjugate comprises two primer sequences that are incorporated into a primer extension product upon engagement of the conjugates and primer extension, while the other polynucleotide conjugate does not contain a primer sequence.

In one aspect, the density of the first polynucleotide conjugate molecules immobilized or directly synthesized on the substrate is sufficiently low to substantially reduce or prevent interaction between adjacent first polynucleotide conjugate molecules on the substrate, or to substantially reduce or prevent interaction between the analyte molecule bound by one first polynucleotide conjugate molecule and an adjacent first polynucleotide conjugate molecule on the substrate.

In another embodiment, provided herein is a method for analyzing a plurality of analytes in a sample, comprising: (i) immobilizing a plurality of first polynucleotide conjugates on a substrate, each of the first polynucleotide conjugates comprising: (a) a first binder for specific binding of an analyte in a plurality of analytes; and (b) a first polynucleotide comprising a first primer sequence, a first identifying sequence that identifies the first binder, and a first engaging sequence; (ii) contacting the substrate having the immobilized plurality of first polynucleotide conjugates with a sample containing or suspected of containing at least one of the plurality of analytes, whereby the at least one analyte in the sample specifically binds to a first binder of the immobilized plurality of first polynucleotide conjugates; (iii) contacting the substrate having the immobilized plurality of first polynucleotide conjugates with a plurality of second polynucleotide conjugates, each of the second polynucleotide conjugates comprising: (a) a second binder for specific binding of an analyte in the plurality of analytes; and (b) a second polynucleotide comprising a second primer sequence, a second identifying sequence that identifies the second binder, and a second engaging sequence, whereby the at least one analyte specifically bound to the first binder specifically binds to a second binder of the plurality of second polynucleotide conjugates, and whereby the first and second polynucleotide conjugates specifically bound to the same analyte are engaged via the first and second engaging sequences; and (iv) analyzing the first and/or second polynucleotide conjugates engaged via the first and second engaging sequences, wherein the analysis in step (iv) indicates the presence, absence and/or amount of the plurality of analytes in the sample. In one embodiment, the first and second binders are the same for each analyte. In one aspect, the plurality of first polynucleotide conjugates are immobilized or directly synthesized on the substrate at a density that substantially reduces or prevents interaction between adjacent first polynucleotide conjugates on the substrate.

BRIEF DESCRIPTION OF THE DRAWINGS

FIG. 16A is a heat map showing responses to each peptide of the 11 peptides in the peptide-DNA conjugate library across all individuals. FIG. 16B shows representative data for two peptides: peptide #2 and peptide #9 shown in FIG. 16A. FIG. 16C shows overall classification performance of the 11-peptide panel in FIG. 16A.

DETAILED DESCRIPTION

Figure 1:
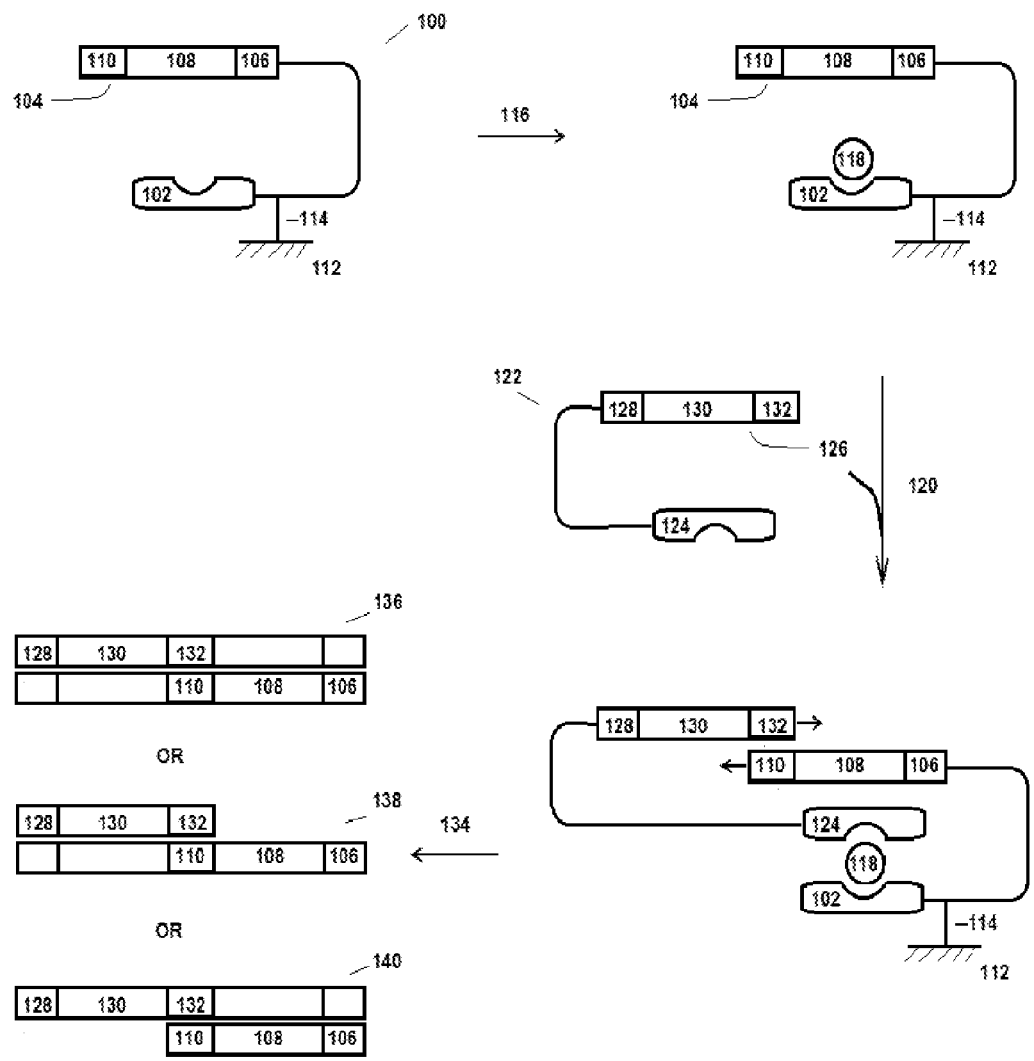
FIG. 1 is a schematic showing a method for analyzing an analyte according to one embodiment of the present disclosure.

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel et al. eds., *Current Protocols in Molecular Biology* (1987); T. Brown ed., *Essential Molecular Biology* (1991), IRL Press; Goeddel ed., *Gene Expression Technology* (1991), Academic Press; A. Bothwell et al. eds., *Methods for Cloning and Analysis of Eukaryotic Genes* (1990), Bartlett Publ.; M. Kriegler, *Gene Transfer and Expression* (1990), Stockton Press; R. Wu et al. eds., *Recombinant DNA Methodology* (1989), Academic Press; M. McPherson et al., *PCR: A Practical Approach* (1991), IRL Press at Oxford University Press; Stryer, *Biochemistry* (4th Ed.) (1995), W. H. Freeman, New York N.Y.; Gait, *Oligonucleotide Synthesis: A Practical Approach* (2002), IRL Press, London; Nelson and Cox, *Lehninger, Principles of Biochemistry* (2000) 3rd Ed., W. H. Freeman Pub., New York, N.Y.; Berg, et al., *Biochemistry* (2002) 5th Ed., W. H. Freeman Pub., New York, N.Y.; D. Weir & C. Blackwell, eds., *Handbook of Experimental Immunology* (1996), Wiley-Blackwell; A. Abbas et al., *Cellular and Molecular Immunology* (1991, 1994), W.B. Saunders Co.;

and J. Coligan et al. eds., *Current Protocols in Immunology* (1991), all of which are herein incorporated in their entireties by reference for all purposes.

Outline

1. Definitions
2. Overview
3. Polynucleotide conjugates and conjugate pairs, libraries, and sets
4. Construction of systems for analyte detection and analysis
5. Methods for antibody detection and analysis
6. Use 1. Definitions As used herein and in the appended claims, the singular forms "a," "an," and "the" include plural referents unless the context clearly dictates otherwise. For example, "a" or "an" means "at least one" or "one or more." Thus, reference to "an antibody or antigen binding fragment thereof" refers to one or more antibodies or antigen binding fragments thereof, and reference to "the method" includes reference to equivalent steps and methods disclosed herein and/or known to those skilled in the art, and so forth.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

A "subject" as used herein refers to an organism, or a part or component of the organism, to which the provided compositions, methods, kits, devices, and systems can be administered or applied. For example, the subject can be a mammal or a cell, a tissue, an organ, or a part of the mammal. Mammals include, but are not limited to, humans, and non-human animals, including farm animals, sport animals, rodents and pets.

As used herein, a "biological sample" can refer to any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

As used herein, a "composition" can be any mixture of two or more products or compounds. It may be a solution, a suspension, liquid, powder, a paste, aqueous, non-aqueous or any combination thereof.

The terms "polynucleotide," "oligonucleotide," "nucleic acid" and "nucleic acid molecule" are used interchangeably herein to refer to a polymeric form of nucleotides of any length, and comprise ribonucleotides, deoxyribonucleotides, and analogs or mixtures thereof. The terms include triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid," and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, inter-nucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, amino alkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. The terms "polynucleotide," "oligonucleotide," "nucleic acid" and "nucleic acid molecule" can comprise any suitable length, such as at least 5, 6, 7, 8, 9, 10, 20, 30, 40, 50, 100, 200, 300, 400, 500, 1,000 or more nucleotides.

It will be appreciated that, as used herein, the terms "nucleoside" and "nucleotide" include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

The terms "polypeptide," "oligopeptide," "peptide," and "protein" are used interchangeably herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The terms "binder," "binding agent," "binding moiety," and "binding group" as used herein refer to any agent or any moiety or group thereof that specifically binds to an analyte molecule of interest, e.g., a biological molecule or portions or complexes thereof with other molecules.

The analyte to be detected and analyzed herein can be any biological molecules including but not limited to proteins, nucleic acids, lipids, carbohydrates, ions, or multicomponent complexes containing any of the above. Examples of subcellular analytes of interest include organelles, e.g., mitochondria, Golgi apparatus, endoplasmic reticulum, chloroplasts, endocytic vesicles, exocytic vesicles, vacuoles, lysosomes, etc. Exemplary nucleic acid analyte can include genomic DNA of various conformations (e.g., A-DNA, B-DNA, Z-DNA), mitochondria DNA (mtDNA), mRNA, tRNA, rRNA, hRNA, miRNA, and piRNA.

As used herein, the term "binding" refers to an attractive interaction between two molecules which results in a stable association in which the molecules are in close proximity to each other. Molecular binding can be classified into the following types: non-covalent, reversible covalent and irreversible covalent. Molecules that can participate in molecular binding include proteins, nucleic acids, carbohydrates, lipids, and small organic molecules such as pharmaceutical compounds. For example, proteins that form stable complexes with other molecules are often referred to as receptors while their binding partners are called ligands. Nucleic acids can also form stable complex with themselves or others, for example, DNA-protein complex, DNA-DNA complex, DNA-RNA complex.

As used herein, the term "specific binding" refers to the specificity of a binder, e.g., an antibody, such that it preferentially binds to a target, such as a polypeptide antigen. When referring to a binding partner, e.g., protein, nucleic acid, antibody or other affinity capture agent, etc., "specific binding" can include a binding reaction of two or more binding partners with high affinity and/or complementarity to ensure selective hybridization under designated assay conditions. Typically, specific binding will be at least three times the standard deviation of the background signal. Thus, under designated conditions the binding partner binds to its particular target molecule and does not bind in a significant amount to other molecules present in the sample. Recognition by a binder or an antibody of a particular target in the presence of other potential interfering substances is one characteristic of such binding. Preferably, binders, antibodies or antibody fragments that are specific for or bind specifically to a target bind to the target with higher affinity than binding to other non-target substances. Also preferably, binders, antibodies or antibody fragments that are specific for or bind specifically to a target avoid binding to a significant percentage of non-target substances, e.g., non-target substances present in a testing sample. In some embodiments, binders, antibodies or antibody fragments of the present disclosure avoid binding greater than about 90% of non-target substances, although higher percentages are clearly contemplated and preferred. For example, binders, antibodies or antibody fragments of the present disclosure avoid binding about 91%, about 92%, about 93%, about 94%, about 95%, about 96%, about 97%, about 98%, about 99%, and about 99% or more of non-target substances. In other embodiments, binders, antibodies or antibody fragments of the present disclosure avoid binding greater than about 10%, 20%, 30%, 40%, 50%, 60%, or 70%, or greater than about 75%, or greater than about 80%, or greater than about 85% of non-target substances.

The terms "capture agent" and "capture group" as used herein refer to any moiety that allows capture of an analyte or a polynucleotide conjugate via binding to or linkage with an affinity group or domain on the analyte, or an affinity tag of the conjugate. The binding between the capture agent and its affinity tag may be a covalent bond and/or a non-covalent bond. A capture agent includes, e.g., a member of a binding pair that selectively binds to an affinity tag on a fusion peptide, a chemical linkage that is added by recombinant technology or other mechanisms, co-factors for enzymes and the like. Capture agents can be associated with a polynucleotide conjugate using conventional techniques including hybridization, cross-linking (e.g., covalent immobilization using a furocoumarin such as psoralen), ligation, attachment via chemically-reactive groups, introduction through post-translational modification and the like.

The term "antibody" as used herein includes an entire immunoglobulin or antibody or any functional fragment of an immunoglobulin molecule which is capable of specific binding to an antigen, such as a carbohydrate, polynucleotide, lipid, polypeptide, or a small molecule, etc., through at least one antigen recognition site, located in the variable region of the immunoglobulin molecule, and can be an immunoglobulin of any class, e.g., IgG, IgM, IgA, IgD and IgE. IgY, which is the major antibody type in avian species such as chicken, is also included. Secreted antibodies can be dimeric with two Ig units as with IgA, tetrameric with four Ig units like teleost fish IgM, or pentameric with five Ig units, like mammalian IgM.

An antibody includes the entire antibody as well as any antibody fragments capable of binding the antigen or antigenic fragment, for example, an epitope, of interest. Examples include complete antibody molecules, antibody fragments or linked antibody fragments, such as Fab, F(ab')$_2$, chemically linked F(ab')$_2$, Fab', scFv (single-chain variable fragment), di-scFv, sdAb (single domain antibody), trifunctional antibody, BiTE (bi-specific T-cell engager), CDRs, $V_L$, $V_H$, and any other portion of an antibody which is capable of specifically binding to an antigen. Antibodies used herein are immunoreactive or immunospecific for, and therefore specifically and selectively bind to, for example, proteins either detected (i.e., analytes in biological samples) or used for detection (i.e., binders or probes) in the assays disclosed herein. An antibody as used herein can be specific for any of the analytes, binders, or epitopes disclosed herein or any combinations thereof. In certain embodiments, an analyte itself of the present disclosure can be an antibody or fragments thereof.

As used herein, a "fragment thereof" "region thereof" and "portion thereof" can refer to fragments, regions and portions that substantially retain at least one function of the full length polypeptide.

As used herein, the term "antigen" may refer to a target molecule that is specifically bound by an antibody through its antigen recognition site. The antigen may be monovalent or polyvalent, i.e., it may have one or more epitopes recognized by one or more antibodies. Examples of kinds of antigens that can be recognized by antibodies include polypeptides, oligosaccharides, glycoproteins, polynucleotides, lipids, or small molecules, etc.

As used herein, the term "epitope" can refer to a peptide sequence of at least about 3, about 4, about 5, about 6, about 7, about 8, about 9, about 10, about 11, about 12, about 13, about 14, about 15, about 16, about 17, about 18, about 19, about 20, between about 20 and about 30, between about 30 and about 40, between about 40 and about 50, or more than about 50, and not more than about 1,000 amino acids (or any integer there between 50 and 1,000), which define a sequence that by itself or as part of a larger sequence, binds to an antibody generated in response to such sequence. There is no critical upper limit to the length of the fragment, which may, for example, comprise nearly the full-length of the antigen sequence, or even a fusion protein comprising two or more epitopes from the target antigen. An epitope for use in the present disclosure is not limited to a peptide having the exact sequence of the portion of the parent protein from which it is derived, but also encompasses sequences identical to the native sequence, as well as modifications to the native sequence, such as deletions, additions and substitutions (conservative in nature).

The terms "complementary" and "substantially complementary" include the hybridization or base pairing or the formation of a duplex between nucleotides or nucleic acids, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%. In one aspect, two complementary sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., Biochemistry, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5× SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1× SSPE, 0.1% SDS, 65° C.; 2) medium stringency: 0.2× SSPE, 0.1% SDS, 50° C. (also referred to as moderate stringency); and 3) low stringency: 1.0× SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5× Denhardt's solution, 5× SSPE, 0.2% SDS at 42° C., followed by washing in 0.2× SSPE, 0.2% SDS, at 42° C. High stringency conditions can be provided, for example, by hybridization in 50% formamide, 5× Denhardt's solution, 5× SSPE, 0.2% SDS at 42° C., followed by washing in 0.1× SSPE, and 0.1% SDS at 65° C. Low stringency hybridization can refer to conditions equivalent to hybridization in 10% formamide, 5× Denhardt's solution, 6× SSPE, 0.2% SDS at 22° C., followed by washing in 1× SSPE, 0.2% SDS, at 37° C. Denhardt's solution contains 1% Ficoll, 1% polyvinylpyrolidone, and 1% bovine serum albumin (BSA). 20× SSPE (sodium chloride, sodium phosphate, EDTA) contains 3 M sodium chloride, 0.2 M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a polymerase, for example, a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Sequence determination" and the like include determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput sequencing" or "next generation sequencing" includes sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeq™ technology by Illumina, Inc., San Diego, Calif.; HeliScope™ by Helicos Biosciences Corporation, Cambridge, Mass.; and PacBio RS by Pacific Biosciences of California, Inc., Menlo Park, Calif.), sequencing by ion detection technologies (such as Ion Torrent™ technology, Life Technologies, Carlsbad, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

"SNP" or "single nucleotide polymorphism" may include a genetic variation between individuals; e.g., a single nitrogenous base position in the DNA of organisms that is variable. SNPs are found across the genome; much of the genetic variation between individuals is due to variation at SNP loci, and often this genetic variation results in phenotypic variation between individuals. SNPs for use in the present disclosure and their respective alleles may be derived from any number of sources, such as public databases (U.C. Santa Cruz Human Genome Browser Gateway (genome.ucsc.edu/cgi-bin/hgGateway) or the NCBI dbSNP website (www.ncbi.nlm nih gov/SNP/), or may be experimentally determined as described in U.S. Pat. No. 6,969,589; and US Pub. No. 2006/0188875 entitled "Human Genomic Polymorphisms." Although the use of SNPs is described in some of the embodiments presented herein, it will be understood that other biallelic or multi-allelic genetic markers may also be used. A biallelic genetic marker is one that has two polymorphic forms, or alleles. As mentioned above, for a biallelic genetic marker that is associated with a trait, the allele that is more abundant in the genetic composition of a case group as compared to a control group is termed the "associated allele," and the other allele may be referred to as the "unassociated allele." Thus, for each biallelic polymorphism that is associated with a given trait (e.g., a disease or drug response), there is a corresponding associated allele. Other biallelic polymorphisms that may be used with the methods presented herein include, but are not limited to multinucleotide changes, insertions, deletions, and translocations. It will be further appreciated that references to DNA herein may include genomic DNA, mitochondrial DNA, episomal DNA, and/or derivatives of DNA such as amplicons, RNA transcripts, cDNA, DNA analogs, etc. The polymorphic loci that are screened in an association study may be in a diploid or a haploid state and, ideally, would be from sites across the genome. Sequencing technologies are available for SNP sequencing, such as the BeadArray platform (GOLDENGATE™ assay) (Illumina, Inc., San Diego, Calif.) (see Fan, et al., Cold Spring Symp. Quant. Biol., 68:69-78 (2003)), may be employed.

"Multiplexing" or "multiplex assay" herein may refer to an assay or other analytical method in which the presence and/or amount of multiple targets, e.g., multiple nucleic acid sequences, can be assayed simultaneously by using more than one capture probe conjugate, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

As used herein, the term "substrate" includes a mechanical support upon which material may be disposed to provide functionality, whether mechanical, biological, optical, chemical or other functionality. A substrate may be unpatterned or patterned, partitioned or unpartitioned. Molecules on a substrate may be disposed in features or may be uniformly disposed on the substrate surface. A substrate may comprise any suitable material, for example, silicon, plastic, glass, ceramic, rubber, metal, polymer, paper, and any combination thereof. In one aspect, the plastic can be polycarbonate, methyl methacrylate, polystyrene, acrylonitrile-butadiene-styrene (ABS), polyethylene, or polypropylene.

2. Overview

The majority of current multiplexed assays use traditional immunoassay principles in which capture groups are used in parallel assays to capture analytes, e.g., antibodies, during incubation with biological samples. For example, microarrays of immobilized proteins or peptides are used to capture target antibodies, followed by detection with secondary antibodies labeled with fluorescent dyes. See Cekaite et al., 2007, Methods Mol. Biol. 360: 335-348; Hartmann et al., 2009, Anal. Bioanal. Chem. 393: 1407-416; Zhu and Qian, 2012, Adv. Genet. 79: 123-155; Andresen et al., 2006, Proteomics 6: 1376-384; Antohe and Cooley, 2007, Methods Mol. Biol. 381: 299-312; Breitling et al., 2009, Mol. Biosyst. 5: 224-234. Other antibody labels have also been proposed, including the use of DNA tags for signal amplification (immuno-PCR). See Niemeyer et al., 2005, Trends Biotechnol. 23: 208-216; and Adler et al., 2008, Analyst 133: 702-718. Sensitivity of these methods, however, is limited by nonspecific binding of the secondary reporter to the surface of the solid support for the microarray or to proteins already bound to the surface. Additional drawbacks include high assay background caused by impure antigens, narrow dynamic range of detection, and inability to detect some spotted protein antigens, presumably due to loss of structure, steric interference and/or electrostatic repulsion.

Assays using encoded microspheres have also been developed. For example, the xMap technology from Luminex is commonly used for suspension microsphere assays, and other barcoded particles are also available. See Dupont et al., 2005, J. Reprod. Immunol. 66: 175-191; Lash et al., 2006, J. Immunol. Methods 309: 205-08; and Smith et al., 2005, Ann NY Acad. Sci. 1050: 286-294. In general, assays with encoded particles are less sensitive compared to corresponding single-plex assays. See Ling et al., 2007, Expert Rev. Mol. Diagn. 7: 87-98; and Liu et al., 2005, Clin. Chem. 51: 1102-09.

Assays with large antigen libraries in solution are also used. For example, large numbers of peptide antigens can be produced and assayed using phage display. See Larman et al., 2011, Nat. Biotechnol. 29: 535-541; and Zhu et al., 2013, Nat. Biotechnol. 31: 331-34. However, this approach is encumbered by interactions between complex patient samples and bacteriophage, resulting in high nonspecific background.

Provided herein are polynucleotide conjugates/constructs, systems, and methods of detecting and/or analyzing an analyte. In one aspect, the present disclosure addresses the issues of the above existing technologies.

In one embodiment, provided herein is a first polynucleotide conjugate comprising: (a) a first binder for specific binding of an analyte; and (b) a first polynucleotide comprising a first identifying sequence that identifies the first binder, a first engaging sequence, and optionally a first primer sequence. In one embodiment, there is additionally provided a second polynucleotide conjugate comprising: (a) a second binder for specific binding of the analyte; and (b) a second polynucleotide comprising a second identifying sequence that identifies the second binder, a second engaging sequence, and optionally a second primer sequence. Since the first and second polynucleotide conjugates are capable of specific binding to the same analyte (via the first and second binders, respectively), the first and second polynucleotide conjugates form a pair. In one aspect, also disclosed herein is a set of polynucleotide conjugates, the set comprising a plurality of the pairs of first and second polynucleotide conjugates. In certain embodiments, two or more of the pairs specifically bind or recognize the same analyte, for example, at the same sequence, region, motif, domain, or structure of the analyte, or at different sequences, regions, motifs, domains, or structures of the analyte. In certain other embodiments, at least two of the pairs specifically bind or recognize different analytes in a sample, making the set of polynucleotide conjugate pairs suitable for use in multiplexed assays.

It is to be understood that in certain embodiments, only one of the first and second identifying sequences is needed, as long as the first and second binders are capable of specific binding to the analyte, and the first and second engaging sequences are capable of engaging the first and second polynucleotides via interaction between the first and second engaging sequences, and thereby engaging the first and second polynucleotide conjugates. Similarly, in certain other embodiments, only one of the first and second primer sequences is needed.

In certain aspects, the binder of a polynucleotide conjugate of the present disclosure comprises one or more moieties. These moieties can be DNA/RNA, aptamers, peptides, proteins, small molecules, lipids, carbohydrates, or derivatives or analogues thereof, in any suitable combination, as long as the binder is capable of specific binding or recognition of an analyte of interest. In certain embodiments, the analyte of interest is an organic or inorganic molecule or molecular complex. The analyte can be naturally occurring, modified or derived from a naturally occurring molecule or molecular complex, or artificially synthesized. In one aspect, an analyte of the present disclosure is present in or obtained from a biological sample. For example, the analyte can be any biological molecules including but not limited to proteins, nucleic acids, lipids, carbohydrates, ions, multicomponent complexes containing any of the above, or subcellular organelles. Exemplary polypeptide analytes include antibodies, antibodies fragments, antibody conjugates, diabodies, enzymes, small peptides, cellular receptors and ligands, protein complexes, and protein-DNA/RNA complexes.

In one aspect, a first polynucleotide conjugate is provided on a substrate or a support surface, e.g., immobilized on the support surface. In some embodiments, the first polynucleotide conjugate is directly or indirectly associated with the support surface. The associate can comprise covalent and/or non-covalent linkage. In one embodiment, a substrate having the first polynucleotide conjugate is contacted with a sample containing or suspected of containing an analyte, for example, a biological sample containing an antibody of interest. In one aspect, the sample can be aqueous or non-aqueous, and can be a solution, suspension, liquid, colloid, gel, gas, powder, or paste. In other aspects, the sample can be prepared or processed in a solution, suspension, liquid, colloid, gel, and gas, in order to be flowable or substantially flowable. In one aspect, the first binder in the first polynucleotide conjugate specifically binds to an analyte in the sample. The substrate having the first polynucleotide conjugate and an analyte specifically bound thereto is then contacted with a second polynucleotide conjugate, which comprise a second binder that is capable of specific binding to the analyte, creating a first binder-analyte-second binder sandwich complex (a ternary complex). Typically, the first polynucleotide conjugate is provided on a substrate, and the second polynucleotide conjugate is provided in solution, suspension, liquid, or colloid.

In certain embodiments, the first and second polynucleotide conjugates are co-localized due to the specific binding to a common analyte. Typically, the first and second engaging sequences of the first and second polynucleotide conjugates become engaged, for example, via sequence complementarity and/or polynucleotide hybridization. In one embodiment, the first and second identifying sequences are coupled to each other via the engagement between the first and second engaging sequences. Coupling can be achieved using a variety of mechanisms. For example, the first and second identifying sequences are coupled by copying or combining into a single molecule comprising sequence information from both identifying sequences. In one embodiment, the first and second engaging sequences can be ligated, with or without extension before ligation. In other embodiments, coupling of the first and second polynucleotides is carried out by a primer extension reaction, for instance, by primer extension from the first and second engaging sequences (bi-directional primer extension), using all or a portion of the second and first polynucleotides as a template, respectively. In other embodiments, coupling of the first and second polynucleotides is carried out by primer extension from the first or second engaging sequence alone (uni-directional primer extension). The first and second polynucleotides engaged via the first and second engaging sequences can be analyzed to determine the presence, absence and/or amount of the analyte in the sample. In one embodiment, the single molecule comprising sequence information from both identifying sequences is analyzed, for example, by determining its sequence by techniques including nucleic acid sequencing. In some aspects, the first and second binders for an analyte can be the same or different.

A method disclosed herein in a multiplexed format can be used to detect and/or analyze a plurality of analytes in a sample by making use of two sets of polynucleotide conjugates. The first set of polynucleotide conjugates comprises a plurality of first polynucleotide conjugates, each of the first polynucleotide conjugates comprising: (a) a first binder for specific binding of an analyte in a plurality of analytes; and (b) a first polynucleotide comprising a first primer sequence, a first identifying sequence that identifies the first binder, and a first engaging sequence. The second set of polynucleotide conjugates comprises a plurality of second polynucleotide conjugates, each of the second polynucleotide conjugates comprising: (a) a second binder for specific binding of an analyte in the plurality of analytes; and (b) a second polynucleotide comprising a second primer sequence, a second identifying sequence that identifies the second binder, and a second engaging sequence. Typically, at least one of the sets of polynucleotide conjugates is anchored to a solid support and the other set of polynucleotide conjugates is in solution. In certain embodiments, co-localization occurs between a first polynucleotide conjugate and a second polynucleotide conjugate in the first and second sets, respectively, either directly or via a third binding agent or an analyte. Typically, the co-localization is mediate by specific binding. In some aspects, co-localization enables the sequence information contained in the first and second identifying sequences to be associated or coupled. The multiplexed format allows assays where either or both of the first and second sets of polynucleotide conjugates may comprise a plurality of binders, each binder capable of specific binding to an analyte to be detected or analyzed in a sample. In certain embodiments, either or both of the first and second sets of polynucleotide conjugates comprise at least about 2, at least about 5, at least about 10, at least about 15, at least about 20, at least about 25, at least about 30, at least about 35, at least about 40, at least about 45, at least about 50, at least about 75, at least about 100, at least about 500, at least about 750, at least about 1,000, at least about 5,000, at least about 10,000, at least about 50,000, at least about 100,000, at least about 500,000, or at least about 1,000,000 different binders. In other embodiments, the set of conjugates comprises between about $10^6$ to about $10^7$, between about $10^7$ to about $10^8$, between about $10^8$ to about $10^9$, between about $10^9$ to about $10^{10}$, between about $10^{10}$ to about $10^{11}$, between about $10^{11}$ to about $10^{12}$, between about $10^{12}$ to about $10^{13}$, between about $10^{13}$ to about $10^{14}$, between about $10^{14}$ to about $10^{15}$, between about $10^{15}$ to about $10^{16}$, between about $10^{16}$ to about $10^{17}$, between about $10^{17}$ to about $10^{18}$, or more than about $10^{18}$ different binders. For example, randomized libraries of natural or unnatural peptides, which can contain about $10^{18}$ peptides, can be used to construct the set of conjugates. In some embodiments, either or both of the first and second sets of polynucleotide conjugates comprise binders each capable of specific binding to an analyte, such that the total number of different analytes that can be detected is at least about 2, at least about 5, at least about 10, at least about 15, at least about 20, at least about 25, at least about 30, at least about 35, at least about 40, at least about 45, at least about 50, at least about 75, at least about 100, at least about 500, at least about 750, at least about 1,000, at least about 5,000, at least about 10,000, at least about 50,000, at least about 100,000, at least about 500,000, or at least about 1,000,000.

In some aspects, the systems, assays, and methods of the present disclosure provide sensitive detection, wide dynamic range, and, ability to carry out and analyze multiplexed assays involving many types of biological molecules. In certain embodiments, nucleic acid sequences are used as readouts for molecular interactions between biological molecules. Nucleic acid sequences can be determined by various means, such as mass spectrometry, hybridization to a microarray, and sequencing techniques including high throughput sequencing.

In certain embodiments, the present disclosure provides a direct mechanism for identifying and discounting false positives by examining the combinations of the first and second identifying sequences that identify the first and second binders, respectively. Typically, a true positive signal from specific binding between an analyte and the first and second binders contain the unique combination of nucleic acid sequence information of all or a portion of the first and second identifying sequences. In contrast, in some aspects, false positive signals contain incompatible combinations of nucleic acid sequence information of all or a portion of the first and second identifying sequences. Typically, such false positive signals can be easily identified. In one aspect, combinations of nucleic acid sequence information of all or a portion of two first identifying sequences or two second identifying sequences (instead of a combination of nucleic acid sequence information of all or a portion of one first identifying sequence and one second identifying sequence) can be identified as being caused by intra-set binding. For example, two first polynucleotide conjugates immobilized on adjacent positions on a substrate may be engaged without specific binding to a common analyte, particularly when the first polynucleotide conjugates are arrayed on the substrate at a high density. In another example, when the first and second identifying sequences for the first and second binders are known, and the first and second binders are known to specifically bind to an analyte of interest, the unique combination of the first and second identifying sequences indicative of specific binding to the analyte is then known. Thus, any combination that contains faulty pairings of the first and second identifying sequences can be identified as a false positive and subtracted from the resulting data. In certain embodiments, because the first polynucleotide conjugate or the set of first polynucleotide conjugates of the assays is secured to a support surface, no additional sorting of products resulting from specific binding to analyte (i.e., true positive signals) from products resulting from non-specific binding (i.e., false positives) in needed, contrary to assays that are performed in solution. For instance, after capturing of an analyte by specific binding of the first binder in a first polynucleotide conjugate, the substrate having the immobilized first polynucleotide conjugate is washed to remove non-specific binding, while the analyte remain specifically bound to the first polynucleotide conjugate. Similarly, after the second binder in a second polynucleotide conjugate specifically binds to the analyte specifically bound by the first binder, the substrate is again washed to remove non-specific binding, while the first and second polynucleotide conjugates remain bound to the analyte. Suitable stringencies for analyte capture, specific binding of the second analyte, washing, and hybridization between the engaging sequences can be achieved by methods known to one of skill in the art, for example, by controlling variables such as temperature, buffer composition, ionic strength, divalent ion concentration, and/or organic co-solvents.

An assay scheme according to one embodiment of the present disclosure is illustrated in FIG. 1. There is provided a first polynucleotide conjugate 100, for example, as one in a set of first polynucleotide conjugates. Only one first polynucleotide conjugate is shown in FIG. 1. However, it is to be understood that a first set of a plurality of first polynucleotide conjugates can be used. The first polynucleotide conjugate comprises a first binder 102 and a first polynucleotide 104. In one embodiment, each first polynucleotide conjugate comprises one first binder specific for an analyte of interest. In other embodiments, a first polynucleotide conjugate comprises a plurality of first binders. In one aspect, the plurality of first polynucleotide conjugates in the first set have different binders, and the different binders can specifically bind to the same analyte or different analytes. The first polynucleotide comprises a first primer sequence 106, a first identifying sequence 108 that identifies the first binder, and a first engaging sequence 110. In one embodiment, the first identifying sequence 108 and the first engaging sequence 110 may overlap or be combined, thus the first binder is identified by a unique first engaging sequence. In another embodiment, the first primer sequence 106 and the first identifying sequence 108 may overlap or be combined, thus the first binder is identified by a unique primer sequence, and the conjugate can be subjected to primer specific PCR for identifying the conjugate or conjugate pair. Typically, the first polynucleotide conjugate is associated with a substrate 112, optionally via a linker 114. It is to be understood that the linker can be positioned at any suitable position, for example, at the 5' of the first polynucleotide (e.g., at the 5' end of the first primer sequence), or at a position in the polypeptide portion in the first polynucleotide conjugate, for example, a position separate from the first binder. The linker may comprise one or more covalent and/or non-covalent linkages, for example, a biotin-streptavidin pair. In other aspects, the linker is cleavable. In some embodiments, the first polynucleotide is directly linked to the substrate, or chemically synthesized in situ directly on the substrate.

In certain aspects, primers for amplification or sequencing can be designed based on all or a portion of the first or second primer sequence. In some embodiments, the first or second primer sequence comprises a universal adapter sequence, and additional sequences can be added to the universal adapter sequence. The added sequences are then used as the basis for designing primers for amplification or sequencing all or a portion of the first or second polynucleotide, or the primer extension product.

In step 116, the substrate having the first polynucleotide conjugate is contacted with an analyte 118. The analyte can be provided in a sample containing the analyte, for example, a biological sample (such as serum, plasma, blood, urine, or other body fluids) containing an antibody indicative of an infection. In one aspect, the substrate having the first polynucleotide conjugate is contacted with a sample suspected of containing the analyte. The analyte specifically binds to the first binder in the first polynucleotide conjugate.

In step 120, a second polynucleotide conjugate 122 is provided, typically in solution. Although only one second polynucleotide conjugate is shown in FIG. 1, it is to be understood that a second set of a plurality of second polynucleotide conjugates can be used. The second polynucleotide conjugate comprises a second binder 124 and a second polynucleotide 126. In one embodiment, each second polynucleotide conjugate comprises one second binder specific for the analyte of interest. In other embodiments, a second polynucleotide conjugate comprises a plurality of second binders. In one aspect, the plurality of second polynucleotide conjugates in the second set have different second binders, and the different binders can specifically bind to the same analyte or different analytes. The second polynucleotide comprises a second primer sequence 128, a second identifying sequence 130 that identifies the second binder, and a second engaging sequence 132. In one embodiment, the second identifying sequence 130 and the second engaging sequence 132 may overlap or be combined, thus the second binder is identified by a unique second engaging sequence. In another embodiment, the second primer sequence 128 and the second identifying sequence 130 may overlap or be combined, thus the second binder is identified by a unique primer sequence, and the conjugate can be subjected to primer specific PCR for identifying the conjugate or conjugate pair. The second binder then specifically binds to the analyte specifically bound to the first polynucleotide conjugate, creating a first binder-analyte-second binder sandwich complex. The first and second polynucleotide conjugates are thus co-localized via specific binding to the common analyte. As a result, the first and second engaging sequences of the first and second polynucleotide conjugates become engaged, for example, via sequence complementarity, polynucleotide hybridization, and/or ligation.

In step 134, the first and second identifying sequences are coupled to each other via the engagement between the first and second engaging sequences. In one embodiment, the first and second engaging sequences can be ligated. In other embodiments, the first and second identifying sequences are coupled by primer extension from the first and second engaging sequences to generate a double-stranded product 136, by primer extension from the first engaging sequence only to generate product 138 (e.g., by blocking primer extension from the second engaging sequence via phosphorylation of the 3' end of the second engaging sequence), or by primer extension from the second engaging sequence only to generate product 140 (e.g., by blocking primer extension from the first engaging sequence via phosphorylation of the 3' end of the first engaging sequence). The products can contain sequence information of all or a portion of the first or second identifying sequence, and can be subjected to sequence determination, for example, by mass spectrometry or nucleic acid sequencing. The products can be optionally amplified using primers that bind to the first primer sequence 106 and/or second primer sequence 128, for example, prior to sequence determination. Determination of the sequences of the products is used to analyze the absence, presence, and/or amount of the analyte in the sample.

3. Polynucleotide Conjugates and Conjugate Pairs, Libraries, and Sets

In certain embodiments, disclosed herein is a polypeptide-polynucleotide conjugate comprising: (a) a polypeptide for specific binding of an analyte; and (b) a polynucleotide comprising an identifying sequence that identifies the polypeptide, an engaging sequence, and optionally a primer sequence. In other embodiments, disclosed herein is a pair of polypeptide-polynucleotide conjugates, comprising a first polypeptide-polynucleotide conjugate and a second polypeptide-polynucleotide conjugate. The first and second polypeptide-polynucleotide conjugates each comprises: (a) a polypeptide for specific binding of an analyte; and (b) a polynucleotide comprising an identifying sequence that identifies the polypeptide, an engaging sequence, and optionally a primer sequence. In certain embodiments, the first and second engaging sequences are capable of engaging the first and second polynucleotides, and become engaged when the first and second polypeptide-polynucleotide conjugates co-localize, for example, due to their specific bind to the same analyte. Since the first and second polypeptide-polynucleotide conjugates are capable of specific binding to the same analyte (via the first and second polypeptides, respectively), the first and second polypeptide-polynucleotide conjugates form a pair. In some aspects, the first and second polypeptides in a pair specifically bind and/or recognize the same analyte, for example, by specific binding and/or recognition of the same sequence, region, motif, domain, or structure (e.g., a protein secondary structure, tertiary structure, or quaternary structure) of an analyte. In certain other aspects, the first and second polypeptides specifically bind and/or recognize different sequences, regions, motifs, domains, or structures of the same analyte. In yet other aspects, the first and second polypeptides are the same.

In one aspect, also disclosed herein is a set of polypeptide-polynucleotide conjugates, the set comprising a plurality of the pairs of first and second polypeptide-polynucleotide conjugates disclosed in any of the embodiments herein or combinations thereof. In certain embodiments, two or more of the pairs specifically bind or recognize the same analyte, for example, at the same sequence, region, motif, domain, or structure of the analyte, or at different sequences, regions, motifs, domains, or structures of the analyte. In certain other embodiments, at least two of the pairs specifically bind or recognize different analytes.

In one aspect, all or part of the polypeptide portion of a polypeptide-polynucleotide conjugate is encoded by nucleic acid sequences within the polypeptide-polynucleotide conjugate. For example, the identifying sequence within the polynucleotide portion of the polypeptide-polynucleotide conjugate can encode all or part of the polypeptide portion. In other embodiments, the nucleic acid sequence that encodes all or a portion of the polypeptide can overlap or coincide with the identifying sequence, the primer sequence, and/or the engaging sequence. In yet other embodiments, the nucleic acid sequence that encodes all or a portion of the polypeptide is distinct from the identifying sequence, the primer sequence, and the engaging sequence, and can be positioned at any suitable position within the polypeptide-polynucleotide conjugate. Arrays having immobilized polypeptide-polynucleotide conjugates and methods of constructing such arrays include those disclosed in US 2012/0270748, entitled "Peptide Display Arrays," which is incorporated herein by reference for all purposes.

The polynucleotide portion of a polypeptide-polynucleotide conjugate can be a polynucleotide of any suitable length, and can include ribonucleotides, deoxyribonucleotides, analogs thereof, or any combinations thereof. The polynucleotide portion in some aspects is synthetic. The polynucleotide portion can be single-, double-, and/or triple-stranded DNA, RNA, PNA, or LNA. In some embodiments, all or part of the polynucleotide portion of a polypeptide-polynucleotide conjugate is RNA. For example, the first and second engaging sequences can be one DNA and one RNA, and when engaged, the RNA engaging sequence can be extended by a reverse transcriptase to generate an extension product.

Figure 2:
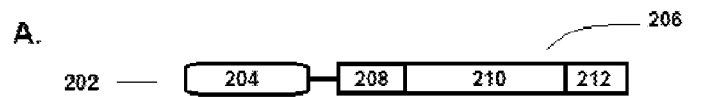
FIGS. 2A-2E are schematic drawings of the polynucleotide conjugates according to some embodiments of the present disclosure.
Figure 2:
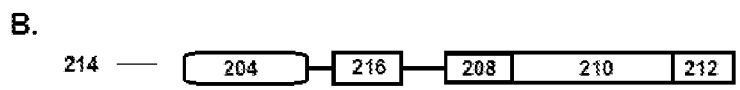
Figure 2:
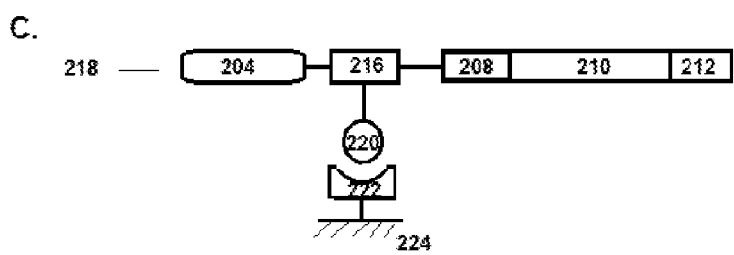
Figure 2:
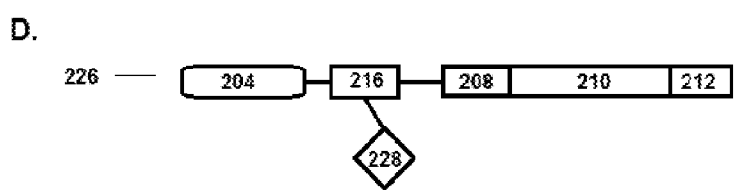
Figure 2:
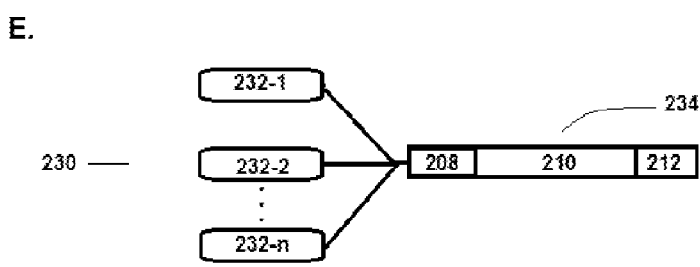
Figure 2:
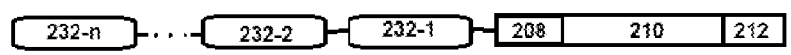
Figure 2:
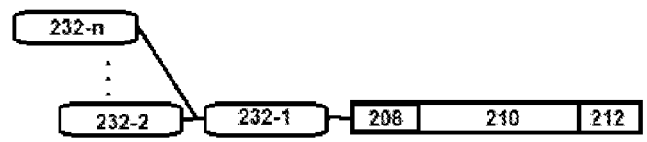

A polypeptide-polynucleotide conjugate 202 according to one embodiment of the present disclosure is illustrated in FIG. 2A. The polypeptide-polynucleotide conjugate comprises a polypeptide portion 204 and a polynucleotide portion 206. In one embodiment, when the analyte of interest is an antibody or antigen binding fragment, the polypeptide portion comprises an epitope for specific binding of the antibody or antigen binding fragment. The polynucleotide portion comprises a primer sequence 208, an identifying sequence 210 that identifies the polypeptide portion, and an engaging sequence 212. In one embodiment, the primer sequence, the identifying sequence, and the engaging sequence are arranged in the 5' to 3' direction in the polynucleotide portion. In another embodiment, the polypeptide portion is conjugated to a portion substantially at the 5' end of the polynucleotide portion. In yet other embodiment, the polypeptide portion is conjugated to the 5' end of the polynucleotide portion. It is to be understood that in certain aspects, there can be additional polynucleotide sequences between the primer sequence and the identifying sequence, and between the identifying sequence and the engaging sequence. In addition, there can be overlap in sequence between the primer sequence, identifying sequence, and engaging sequence.

As shown in FIG. 2B, a polypeptide-polynucleotide conjugate 214 according to one embodiment of the present disclosure further comprises a tag 216. In one embodiment, the tag is at the C-terminus of the polypeptide portion. In another embodiment, the tag is conjugated to a portion substantially at the 5' end of the polynucleotide portion. In yet other embodiments, the tag is conjugated to the 5' end of the polynucleotide portion. In other embodiments, the tag can be at the N-terminus of the polypeptide portion, or linked to any suitable amino acid residue within the polypeptide portion. In one aspect, the tag comprises an affinity tag 220 capable of specific binding by a capture agent 222, which in some embodiments is immobilized on a substrate 224, as shown in the polypeptide-polynucleotide conjugate 218 of FIG. 2C. It is to be understood that the polypeptide-polynucleotide can be covalently or non-covalently bound, either directly or indirectly, to the substrate. For example, a direct chemical bond between the tag (or another portion of the polypeptide-polynucleotide conjugate) and the substrate can be used to immobilize the polypeptide-polynucleotide conjugate.

In another embodiment, the polypeptide-polynucleotide conjugate further comprises a purification tag. For example, tag 216 can further comprise a purification tag. In other examples, a purification tag 228 is attached or linked to tag 216 in FIG. 2D. In one embodiment, the purification tag is an oligonucleotide, for example, a DNA or RNA fragment. In one aspect, the purification tag is common between a pair of first and second polypeptide-polynucleotide conjugates. In another aspect, the purification tag is common among the plurality of first and second polypeptide-polynucleotide conjugates in a set of multiple pairs of first and second polypeptide-polynucleotide conjugates. In yet another aspect, the purification tag is used for purification of an individual polypeptide-polynucleotide conjugate, a pair or a set. In certain embodiments, full-length members of the pair or set are purified using the purification tag.

In yet another embodiment depicted in FIG. 2E, a polypeptide-polynucleotide conjugate 230 comprises a plurality of polypeptide portions 232-1, 232-2, . . . , 232-n, conjugated to a polynucleotide portion 234. The polypeptide portions can be conjugated to the polynucleotide portion in parallel (e.g., as shown in the top panel of FIG. 2E), in tandem (e.g., as shown in the middle panel of FIG. 2E), or in a branched configuration (e.g., as shown in the bottom panel of FIG. 2E). In certain embodiments, integer n equals to 2, 3, 4, 5, 6, 7, 8, 9, or 10. In other embodiments, integer n is greater than about 10, about 15, or about 20.

In certain embodiments, a polypeptide-polynucleotide conjugate comprises one or more enzyme cleavage sites. In one aspect, the enzyme cleavage site is in the polypeptide portion of the conjugate. In another aspect, the enzyme cleavage site is in the polynucleotide portion of the conjugate. In some embodiments, the enzyme cleavage site is in the primer sequence, the identifying sequence, or the engaging sequence. In one aspect, the first and second polypeptide-polynucleotide conjugates form a complex, for example, by a covalent and/or noncovalent interaction, before specific binding to an analyte. In some embodiments, the enzyme cleavage site in the polypeptide-polynucleotide conjugate is used for controlling the stability of the engaged first and second polypeptide-polynucleotide conjugates.

In particular embodiments, the engaging sequence is cleavable, at one or more nucleic acid residues. For example, the engaging sequence may include one or more uracil bases or deoxyuridine (dU) moieties. In one aspect, dUTP can be incorporated into the polynucleotide portion of the polypeptide-polynucleotide conjugate, for example, by including dUTP or substituting dUTP for dTTP in a PCR reaction for amplifying the polynucleotide portion, or during synthesis of a primer used for making, amplifying, or modifying the polynucleotide portion. A uracil DNA glycosylase (UDG) can be used to cleave the glycosidic bond between the uracil base and the deoxyribose sugar. See, Duncan, 1981, The Enzymes 14:565, ed.: Boyer P. Double or single-stranded dU-containing DNA is a substrate for UDG, whereas RNA and normal dT-containing DNA are not. The enzyme does not act upon free dUTP or free deoxyuridine. After UDG cleaves the uracil base from the phosphodiester backbone, the resulting abasic (apyrimidinic) sites block replication by DNA polymerases, and are labile to acid/base hydrolysis. In particular embodiments, UDG is used in combination with DNA glycosylase-lyase Endonuclease VIII. UDG catalyses the excision of a uracil base, forming an apyrimidinic site while leaving the phosphodiester backbone intact. The lyase activity of Endonuclease VIII breaks the phosphodiester backbone at the 3' and 5' sides of the abasic site so that base-free deoxyribose is released. In one embodiment, the USER (Uracil-Specific Excision Reagent) enzyme from New England Biolabs is used. It is to be understood that other similar enzymes or enzyme combinations can be used. In certain embodiments, the 3' end of the cleaved oligonucleotide is treated to allow extension by a polymerase. In one aspect, the 3' end of the cleaved oligonucleotide is dephosphorylated, for instance, by a polynucleotide kinase (PNK) such as a T4 PNK.

Upon analyte binding, in some aspects, the engaged first and second engaging sequences form a double-stranded or a single-stranded oligonucleotide. Cleavage (e.g., UDG-mediated cleavage of dU-containing DNA) within the double-stranded or single-stranded oligonucleotide destabilizes the engaged first and second engaging sequences. For example, cleaving a short oligonucleotide off the 3' end leads to the departure of the cleaved portion from the first or second engaging sequence. In another example, cleavage of the short oligonucleotide allows the cleaved portion to be displaced by a polymerase, for example, a DNA polymerase. In one embodiment, one base or nucleic acid residue is cleaved from the 3' end of the first and/or second engaging sequences. In certain embodiments, an oligonucleotide (either double-stranded or single-stranded) of about 2, about 3, about 4, about 5, about 6, about 7, about 8, about 9, about 10, about 11, about 12, about 13, about 14, about 15, or more than about 15 bases or nucleic acid residues is cleaved from the 3' end of the first and/or second engaging sequences. In certain aspects, the first and/or second engaging sequences cleaved at the 3' ends are capable of being extended by an agent, for example, a polymerase. In certain embodiments, the first and/or second engaging sequences are terminated, for example, by including dideoxynucleotides or 3' modifications, such that extension by an agent (e.g., a polymerase) from the terminated engaging sequence is blocked. In one aspect, cleavage at the 3' ends of the first and/or second engaging sequences removes the blockage.

The agent for extension of a cleaved polynucleotide, for example, the first and/or second engaging sequences cleaved at the 3' or 5' ends, may be any compound or system which will function to accomplish the synthesis of primer extension products, including enzymes. Suitable enzymes for this purpose include, for example, E. coli DNA polymerase I, Klenow fragment of E. coli DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. The suitable enzyme will facilitate combination of the nucleotides in the proper manner to form extension products which include complementary sequences to a template polynucleotide. In some embodiments, the synthesis/extension is initiated at the 3' end of the first engaging sequence hybridized to the second engaging sequence and proceed in the 5' to 3' direction along the second engaging sequence, until synthesis terminates, producing molecules of different lengths. In certain embodiments, synthesis/extension proceeds in the 5' to 3' direction along the second engaging sequence, the second identifying sequence, and/or the second primer sequence, while optionally, synthesis/extension also proceeds in the 5' to 3' direction along the first engaging sequence, the first identifying sequence, and/or the first primer sequence. It is, however, envisaged that in certain embodiments, synthesis/extension can terminate at any position before reaching the 5' end of the polynucleotide portion that is used as the template.

Also provided herein is a pair of polypeptide-polynucleotide conjugates, each of which is capable of specific binding to the same analyte (via the first and second polypeptides, respectively). In one aspect, the first or second polypeptide-polynucleotide conjugate of the pair is provided on a support, while the other conjugate of the pair is provided in solution. In certain embodiments, the immobilized polypeptide-polynucleotide conjugate of the pair is provided at a low surface density on the support such that co-localization of two immobilized polypeptide-polynucleotide conjugates is minimized In one aspect, the low surface density reduces intra-set binding, and ensures specific binding of an analyte to the immobilized polypeptide-polynucleotide conjugate, and specific binding of the polypeptide-polynucleotide conjugate in solution to the analyte specifically bound to the immobilized conjugate. In certain aspects, the analyte of interest is a bivalent analyte (e.g., a bivalent antibody such as an IgG). Low surface density of the immobilized polypeptide-polynucleotide conjugate on the support prevents the bivalent analyte from simultaneously binding to two immobilized polypeptide-polynucleotide conjugates, which analyte would then be unavailable for specific binding of the conjugate provided in solution. In one aspect, low surface density of the immobilized conjugates reduces false positive signals due to non-specific binding of the analyte to the substrate. For example, when the analyte non-specifically binds to the substrate surface and does not bind to an immobilized conjugate, even if a conjugate provided in solution is able to bind the analyte, the chance of the conjugate provided in solution interacting with an immobilized conjugate is low due to the low surface density of the immobilized conjugates. Thus, in certain embodiments, low surface density of the immobilized polypeptide-polynucleotide conjugate is critical.

Figure 15:
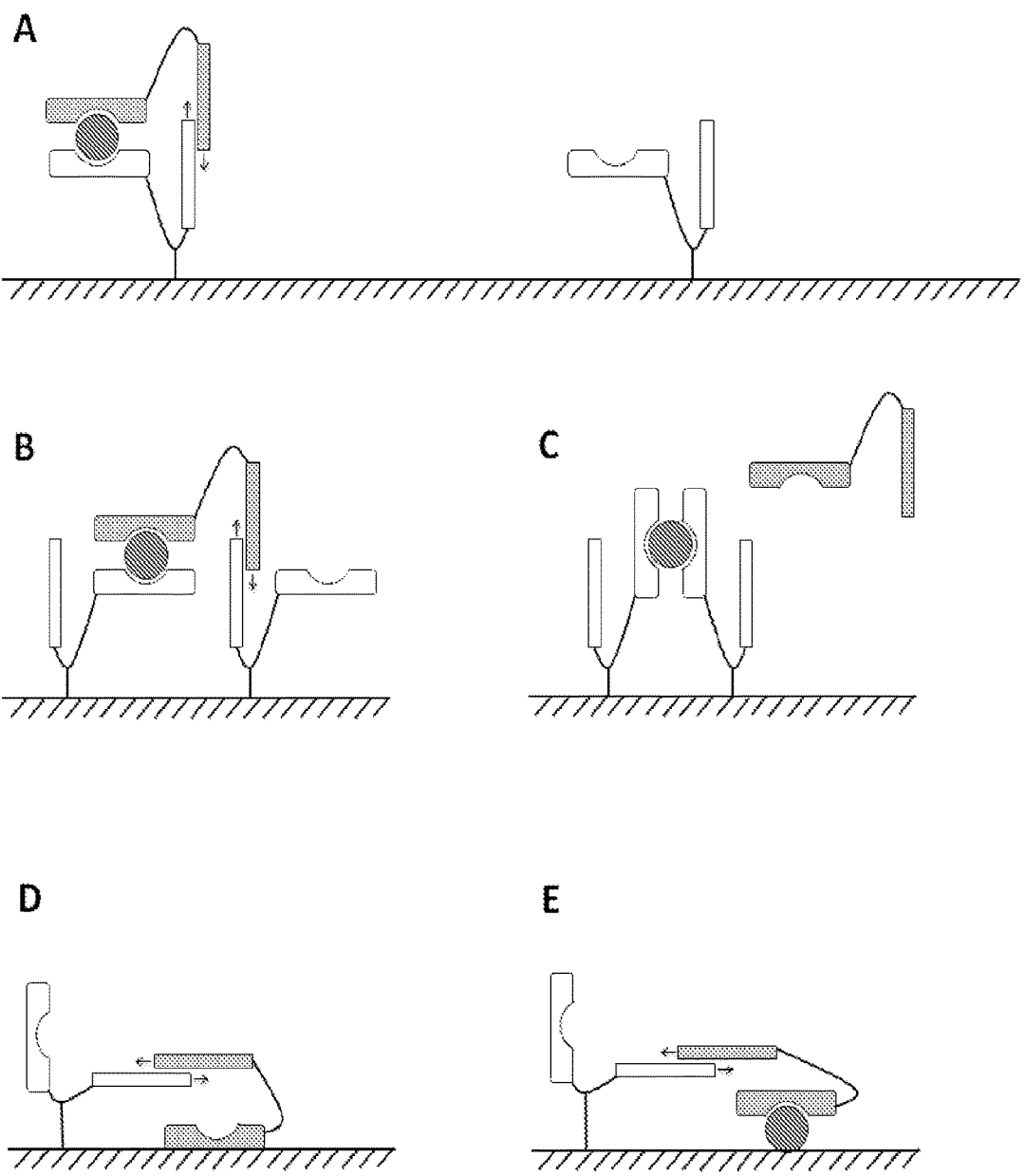
FIGS. 15A-15E are schematics showing interactions influenced by surface density of immobilized conjugates on a substrate according to some embodiments of the present disclosure.

In some aspects, the density of the immobilized polypeptide-polynucleotide conjugates on the substrate is so low as to substantially reduce or prevent an analyte bound to one immobilized conjugate from interacting with an adjacent immobilized conjugate. For example, as shown in FIG. 15A, a desired primer extension product can be generated between a pair of immobilized and soluble conjugates specifically bound to the same analyte, while an adjacent immobilized conjugate does not interact with the pair of immobilized and soluble conjugates or the analyte. In some aspects, when the surface density of the immobilized conjugates is high, the soluble member of a conjugate pair specifically bound to the same analyte may interact with an adjacent immobilized conjugate, giving rise to an intra-set primer extension product, as shown in FIG. 15B. In other aspects, as shown in FIG. 15C, two adjacent immobilized conjugates may occupy both binding sites on a bivalent analyte, rendering it unavailable for specific binding of a conjugate provided in solution. In some aspects, a polypeptide-polynucleotide conjugate provided in solution (i.e., a second conjugate) may non-specifically bind to the substrate at a position close to an immobilized conjugate, as shown in FIG. 15D. In one aspect, the concentration of the soluble conjugates is controlled to substantially reduce or eliminate non-specific binding of the soluble conjugates to the substrate, thereby reducing background or false positive signals of the assay. In another aspect, due to the low surface density of the immobilized polypeptide-polynucleotide conjugates, the chance of the non-specifically bound second conjugate interacting with an immobilized conjugate is substantially reduced or eliminated, thereby reducing background or false positive signals of the assay. In some aspects, as shown in FIG. 15E, an analyte may non-specifically bind to the substrate in proximity to an immobilized conjugate, but not to the immobilized conjugate itself. In one aspect, non-specific binding of the analyte to the substrate is substantially reduced or eliminated, thereby reducing background or false positive signals of the assay. In another aspect, due to the low surface density of the immobilized polypeptide-polynucleotide conjugates, the chance of the non-specifically bound analyte or a second conjugate bound to the analyte interacting with an immobilized conjugate is substantially reduced or eliminated, thereby reducing background or false positive signals of the assay.

In some aspects, for example, in a multiplexed assay, the immobilized conjugates comprise binders specific for a plurality of analytes $A_1, A_2, \ldots, A_i, \ldots, A_n$, where n is an integer greater than 1, and $1 \leq i \leq n$. In one aspect, there is no requirement that the density of the total number of immobilized conjugates (i.e., the conjugates specific for analytes $A_1, A_2, \ldots, A_i, \ldots,$ or $A_n$ collectively) is low, as long as the "effective density" of the immobilized molecules of the analyte $A_i$-specific conjugate is sufficiently low. Low effective density of analyte $A_i$-specific conjugate is achieved, for example, due to the presence of many immobilized conjugates specific for other analytes. In one embodiment, the effective density of analyte $A_i$-specific conjugates immobilized on the substrate is sufficiently low to prevent analyte $A_i$ from binding to two adjacent analyte $A_i$-specific conjugates, thus eliminating or reducing intra-set binding. Assay signals caused by intra-set binding can be identified, for example, by the combination of the first and second identifying sequences. In other aspects, the effective density of analyte $A_i$-specific conjugates is sufficiently low to eliminate or reduce false positive signals due to non-specific binding of analyte $A_i$ to the substrate. For example, even if an $A_i$-specific conjugate provided in solution is able to bind the analyte non-specifically bound to the substrate, the chance of the conjugate provided in solution interacting with an immobilized $A_i$-specific conjugate is low due to the low effective surface density of the immobilized $A_i$-specific conjugates. Thus, in certain aspects, particularly for multiplexed assays, the density of immobilized conjugates on a substrate can increase as complexity increases, while the effective density of conjugates specific for each individual analyte remains low.

In one aspect, potential increase in non-specific interactions resulting from higher density of the total number of immobilized conjugates can be mitigated by identifying systematic non-specific interactions, e.g., those resulting from direct conjugate-conjugate interactions that are not mediated by analyte. The conjugates that are more likely to engage in non-specific interactions can be removed.

In some aspects, while the density of the immobilized polypeptide-polynucleotide conjugates on the substrate is so low as to substantially reduce or prevent adjacent conjugates from interacting, interactions between some adjacent conjugates are allowed. For example, some adjacent polypeptide-polynucleotide conjugates on a substrate may interact when they are immobilized using a random access method. Since the overall frequency of interactions can be kept sufficiently low, the ability of the present assay to detect true positive signals is not comprised.

In certain embodiments, when the interactions between conjugates or between an analyte and a conjugate (for example, interactions between two adjacent immobilized conjugates, interaction between a soluble conjugate non-specifically bound to the substrate and an immobilized conjugate, or interaction between an analyte non-specifically bound to two adjacent immobilized and/or soluble conjugates) are referred to as being substantially reduced or prevented, the undesired interactions (i.e., the interactions to be reduced or prevented) occurs in less than about 50%, less than about 40%, less than about 30%, less than about 20%, less than about 10%, less than about 5%, less than about 1%, less than about 0.5%, less than about 0.1%, less than about 0.05%, less than about 0.01%, less than about 0.005%, or less than about 0.001% of all the interactions between conjugates or between analytes and conjugates in an assay.

In other aspects, the conjugates can be immobilized on a substrate by ordered molecule deposition and/or using a microfluidic device, in order to tightly control the spatial distribution of the conjugates. In certain embodiments, each conjugate is immobilized at a known location (e.g., at position (x, y)) on a substrate. Distance between the known locations can be determined, for example, based on the length of the conjugate molecule, in order to eliminate or reduce the frequency of interactions between adjacently arrayed conjugates.

In certain embodiments, the analyte concentration in a sample is above the inverse of its binding constant to the peptide portion of the first and/or second polypeptide-polynucleotide conjugates. In other embodiments, the analyte concentration in a sample is below or substantially the same as the inverse of the analyte's binding constant to the first and/or second peptide portions. Under such circumstances, the present disclosure provides methods of increasing the efficiency of capturing the analyte by the first and/or second polypeptide-polynucleotide conjugates.

In certain aspects, a pair of the first and second polypeptide-polynucleotide conjugates is pre-loaded on a support, before capturing of a bivalent analyte. In certain aspects, one or both of the first and second polypeptide-polynucleotide conjugates are immobilized or anchored on the support. In some embodiments, it is envisaged that one polypeptide-polynucleotide conjugate of the pair is loaded on the support before loading of the other conjugate. In certain other aspects, the first and second polypeptide-polynucleotide conjugates are pre-loaded on the support substantially simultaneously. In one aspect, a transient complex forms between the first and second polypeptide-polynucleotide conjugates before analyte binding. Consequently, a ternary complex between the bivalent analyte and the first and second polypeptide-polynucleotide conjugates is formed immediately upon analyte capture. In the ternary complex, one binding site of the bivalent analyte interacts with the first polypeptide-polynucleotide conjugate and the other binding site with the second polypeptide-polynucleotide conjugate. In one aspect, following analyte capture, the support is washed under conditions that destabilize the transient complex between the first and second polypeptide-polynucleotide conjugates, retaining the polypeptide-polynucleotide conjugates engaged in the ternary complex while releasing those not engaged in the ternary complex (e.g., those first and second polypeptide-polynucleotide conjugates interacting via the engaging sequences only, and not via specific binding to the bivalent analyte). In this case, only the polypeptide-polynucleotide conjugates specifically bound to the bivalent analyte (e.g., an antibody) in the ternary complex contribute to assay signal.

In some embodiments, concentration of an analyte is lower than the inverse value of the analyte's binding constant to a binder, for example, the polypeptide portion of a polypeptide-polynucleotide conjugate. In certain embodiments, the analyte of interest is a low affinity antibody (i.e., an antibody with a low binding constant). In one aspect, when the first and second polypeptide-polynucleotide conjugates are presented sequentially to a low affinity antibody, only a fraction of the molecules of the low affinity antibody are captured by the first polypeptide-polynucleotide conjugate. The binding constant of the low affinity antibody also determines binding of the second polypeptide-polynucleotide conjugate to the antibody, in which again only a fraction of the antibody molecules bound to the first conjugates would specifically bind to the second conjugate. In contrast, conjugates of the transient conjugate complex are in physical proximity, and both are available for specific binding to the analyte. Thus in certain aspects, allowing the first and second polypeptide-polynucleotide conjugates to form a transient conjugate complex before analyte binding increases capture efficiency and/or affinity (e.g., capturing more analyte molecules, or capturing analytes with higher affinity), when compared to sequential interaction between the analyte and the first conjugate followed by interaction between the second conjugate and the analyte/first conjugate complex.

In certain aspects of the sequential presentation of the first and second polypeptide-polynucleotide conjugates, the later presented second conjugate, when presented at a sufficiently high concentration/density on a substrate, may displace the first conjugate from the analyte and result in loss of assay signal. In one aspect, allowing the first and second polypeptide-polynucleotide conjugates to form a transient conjugate complex before analyte binding reduces analyte displacement by the polypeptide-polynucleotide conjugates. In one embodiment, transient conjugate complex formation ameliorates issues associated with use of excessive amounts of polypeptide-polynucleotide conjugates, such as analyte displacement and consequent loss of signal. In another aspect, transient conjugate complex formation reduces or eliminates the presence of free polypeptide-polynucleotide conjugates for prolonged periods of time.

In certain other aspects, no separate step for delivering the second polypeptide-polynucleotide conjugate is necessary. In one embodiment, the transient conjugate complex can be pre-formed, and then associated with a substrate. In one embodiment, the transient conjugate complex can be pre-formed in bulk and stored for prolonged periods of time.

Figure 3:
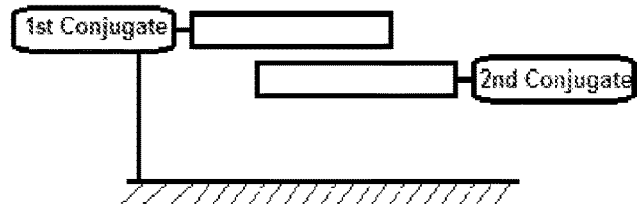
FIGS. 3A-3D are schematic drawings of the polynucleotide conjugate pairs according to some embodiments of the present disclosure.
Figure 3:
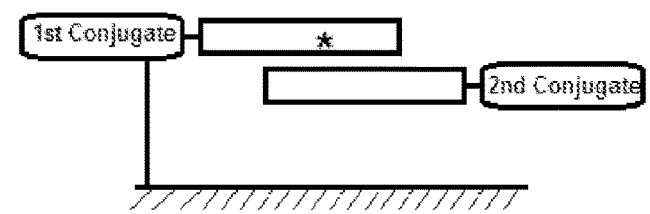
Figure 3:
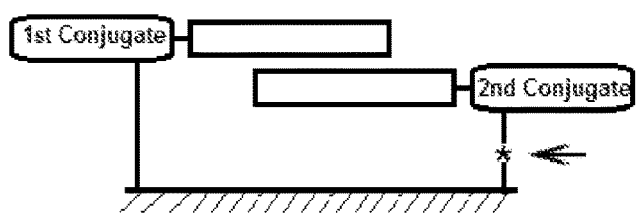
Figure 3:
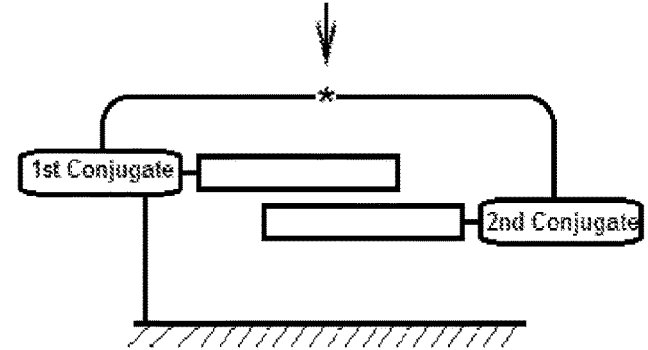

A number of configurations of the first and second polypeptide-polynucleotide conjugates can be used to promote transient conjugate complex formation between the first and second polypeptide-polynucleotide conjugates. Exemplary configurations are shown in FIG. 3A-3D, and it is to be understood the configurations can be used alone or in any suitable combination. For example, shown in FIG. 3A is a transient conjugate complex formed through polynucleotide hybridization between the polynucleotide portions of the first and second polypeptide-polynucleotide conjugates. In certain aspects, the transient conjugate complex formation and solid support immobilization (e.g., via streptavidin/biotin interaction) are preformed under conditions favoring high stability, such as low temperatures and high salt concentrations. In other aspects, stability of the transient conjugate complex is controlled by controlling hybridization conditions, for example, by controlling variables such as temperature, buffer composition, ionic strength, divalent ion concentration, and organic co-solvents.

FIG. 3B shows a transient conjugate complex formed through polynucleotide hybridization between the polynucleotide portions of the first and second polypeptide-polynucleotide conjugates, and the polynucleotide involved in the hybridization can comprise one or more cleavable sites. The stability of the transient conjugate complex is controlled by hybridization conditions and the length of the polynucleotide involved in the hybridization. In one aspect, cleavage at the cleavable sites shortens sequence involved in the hybridization and thus destabilizes the transient conjugate complex. In one embodiment, the cleavable site is cleavable by an enzyme such as UDG.

FIG. 3C shows a transient conjugate complex formed through polynucleotide hybridization between the polynucleotide portions of the first and second polypeptide-polynucleotide conjugates. In addition, the second polypeptide-polynucleotide conjugate is attached to the support by a linker, for example, a cleavable linker. In one embodiment, the linker is a covalent linker or a non-covalent linker. Suitable cleavable linkers include and are not limited to disulfide linkers and photo-cleavable biotin linkers. For example, diol containing linkers can be used. In one aspect, conditions favoring hybridization are used for the transient conjugate complex formation and the solid support loading (e.g., streptavidin/biotin interaction). In certain embodiments, after the first and second polypeptide-polynucleotide conjugates are immobilized on the support, conditions weakening hybridization can be used if needed, since the two conjugates of the transient conjugate complex are held in proximity by their linkers to the solid support. In other embodiments, upon analyte binding, the linker attaching the second polypeptide-polynucleotide conjugate is cleaved to release the second polypeptide-polynucleotide conjugates not engaged in ternary complexes (e.g., those second polypeptide-polynucleotide conjugates interacting with the first polypeptide-polynucleotide conjugates via the engaging sequences only, and not via specific binding to the analyte).

Shown in FIG. 3D is a transient conjugate complex formed through polynucleotide hybridization between the polynucleotide portions of the first and second polypeptide-polynucleotide conjugates, and by a linker between the first and second polypeptide-polynucleotide conjugates. In one embodiment, the linker is a covalent linker or a non-covalent linker. In certain aspects, the linker is a cleavable linker. Suitable cleavable linkers include and are not limited to disulfide linkers and photo-cleavable biotin linkers. For example, diol containing linkers can be used. In certain aspects, the linker is between the first and second polypeptide portions of the conjugates. In other aspects, the linker is between portions other than the first and second engaging sequences of the first and second polypeptide-polynucleotide conjugates. In certain embodiments, the linker does not affect specific binding of an analyte to the polypeptide portions of the conjugate pair. In certain embodiments, upon analyte binding, the linker is cleaved to release the second polypeptide-polynucleotide conjugates not engaged in ternary complexes (e.g., those second polypeptide-polynucleotide conjugates interacting with the first polypeptide-polynucleotide conjugates via the engaging sequences only, and not via specific binding to the analyte).

In one aspect, also disclosed herein is a set of polypeptide-polynucleotide conjugates, the set comprising a plurality of the pairs of first and second polypeptide-polynucleotide conjugates disclosed in any of the embodiments herein or combinations thereof. In certain embodiments, either or both of the first and second sets of polypeptide-polynucleotide conjugates comprise at least about 2, at least about 5, at least about 10, at least about 15, at least about 20, at least about 25, at least about 30, at least about 35, at least about 40, at least about 45, at least about 50, at least about 75, at least about 100, at least about 500, at least about 750, at least about 1,000, at least about 5,000, at least about 10,000, at least about 50,000, at least about 100,000, at least about 500,000, or at least about 1,000,000 different polypeptides. In some embodiments, either or both of the first and second sets of polypeptide-polynucleotide conjugates comprise polypeptides each capable of specific binding to an analyte, for example, an antibody, such that the total number of different analytes that can be detected is at least about 2, at least about 5, at least about 10, at least about 15, at least about 20, at least about 25, at least about 30, at least about 35, at least about 40, at least about 45, at least about 50, at least about 75, at least about 100, at least about 500, at least about 750, at least about 1,000, at least about 5,000, at least about 10,000, at least about 50,000, at least about 100,000, at least about 500,000, or at least about 1,000,000. In certain embodiments, either or both of the first and second sets of polypeptide-polynucleotide conjugates comprise polypeptides each comprising one or more epitopes capable of specific binding to an antibody, such as a monoclonal antibody. In certain embodiments, either or both of the first and second sets of polypeptide-polynucleotide conjugates comprise polypeptides each comprising one or more epitopes capable of specific binding to a collection of antibodies, for example, a polyclonal antibody, or antibodies specific to a marker associated with a disease or a condition.

4. Construction of Systems for Analyte Detection and Analysis

Also provided herein are methods for constructing systems for analyte detection and analysis, for example, reagents, arrays, devices, and platforms for detecting and analyzing antibodies. For example, a polypeptide-polynucleotide conjugate can be produced in a number of ways. For example, methods for constructing polypeptide-polynucleotide conjugates and polypeptide arrays by in vitro translation have been developed, including protein in situ array (PISA) production, nucleic acid programmable protein array (NAPPA) production, DNA to protein array (DAPA) construction, and arraying of proteins using in situ puromycin capture. See, for example, He and Taussig, Nucleic Acids Res., 29: e73 (2001); Ranachandran, et al., Science, 305: 86-90 (2004); He, Nat. Methods, 5:175-177 (2008); and Tao and Zhu, Nat. Biotech, 24:1253-1254 (2006), all of which are incorporated herein by reference in their entireties for all purposes. In addition to approaches that require individually synthesized nucleic acid templates, methods for constructing polypeptide-polynucleotide conjugates and polypeptide arrays are also described in U.S. Patent Application Publication Nos. US 2011/0245101, US 2012/0270748 and US 2012/0258871, all of which are incorporated herein by reference in their entireties for all purposes.

In certain embodiments, the polynucleotide portion of a polypeptide-polynucleotide conjugate of the present disclosure may be created by synthesis methods known in the art. In certain embodiments, the primer sequence and/or the engaging sequence can be different or the same among the polypeptide-polynucleotide conjugates. In certain embodiment, the polynucleotide portion comprises a sequence that encodes all or a portion of the polypeptide portion of the conjugate. For example, the identifying sequence may encode all or a portion of the polypeptide portion of the conjugate. In certain aspects, the primer sequence and/or the engaging sequence are common among the polypeptide-polynucleotide conjugates, and the identifying sequence is the sequence that varies among the polypeptide-polynucleotide conjugates. In certain embodiments, polypeptide-polynucleotide conjugates of the present disclosure comprise a common UTR region and/or a common region encoding a peptide tag for purification. In some embodiments, the common region among the polypeptide-polynucleotide conjugates is about 20, about 30, about 40, about 50, about 60, about 70, about 80, about 90, about 100, about 110, about 120, about 130, about 140, about 150, about 160, about 170, about 180, about 190, about 200 nucleotides in length. In other embodiments, this common region is longer than about 200 nucleotides in length. In other embodiments, the polypeptide-encoding region is about 10, about 20, about 30, about 40, about 50, about 60, about 70, about 80, about 90, about 100, about 110, about 120, about 130, about 140, about 150, about 160, about 170, about 180, about 190, about 200 nucleotides in length. In other embodiments, the polypeptide-encoding region is longer than about 200 nucleotides in length. In yet other embodiments, the total length of the common region and the polypeptide-encoding region is about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, or more than about 400 nucleotides. In certain aspects, one or more portions of the polypeptide-polynucleotide conjugates are synthesized first, and optionally arrayed on a support, before additional portions of the conjugates are added, for example, by a ligation reaction. For example, the polypeptide-encoding regions can be directly synthesized on a support in situ to form an array, then the common regions are added.

In certain embodiments, a polypeptide-polynucleotide conjugate is constructed by combining an existing polypeptide-polynucleotide conjugate (which comprises a polypeptide portion and a polynucleotide portion, which polynucleotide portion comprises an identifying sequence and optionally a primer sequence) and an engaging sequence. In one embodiment, the existing polypeptide-polynucleotide conjugate is a polypeptide-cDNA conjugate, for example, one in which the cDNA encodes all or a portion of the polypeptide portion.

In one embodiment, construction of a polypeptide-cDNA conjugate comprises optimization of codon usage, secondary structure, and/or GC content. In one aspect, a polypeptide-cDNA conjugate is produced by subjecting a cDNA construct to in vitro translation. In certain aspects, translational efficiency is influenced by both the secondary structures of mRNA, including those in the 5' UTR and ribosomal binding site, and codon usage biases. In certain embodiments, potential effects of secondary structure on translation efficiency are minimized by optimizing the polypeptide-encoding cDNA regions. In certain embodiments, the first polypeptide-cDNA conjugate (e.g., one immobilized on a support) and the second polypeptide-cDNA conjugate (e.g., one provided in solution) have the same polypeptide portion, or different polypeptide portions that comprise binders that specifically bind to the same binding site, sequence, region, epitope, domain, or structure of the analyte. In some aspects, hairpins may form in the primer extension products formed by joining the first and second polypeptide-cDNA conjugates, through interaction between regions that encode the same polypeptide portion and share sequence complementarity. Such hairpins structures may form during amplification and/or sequencing of the primer extension products. In certain embodiments, the same polypeptide portion or the same epitope between the first and second polypeptide-cDNA conjugates are encoded differently (e.g., by alternative codon usage) to maximize polypeptide yields and minimize unwanted hairpin formation.

In one embodiment, the engaging sequences of the first and second polypeptide-cDNA conjugates comprise complementary sequences. In one embodiment, design of the complementary sequences for primer extension (for example, regions E1 and E1' in FIG. 4) is guided by the rules of post-T7-promotor nucleotide-specific variation to maximize mRNA production. See Milligan and Uhlenbeck, Methods in enzymology 180, 51 (1989). In certain embodiments, a polypeptide-cDNA conjugate of the present disclosure further comprises a UTR region and a region encoding a peptide tag for purification. In some aspects, the engaging sequences are designed to minimize mis-hybridization between the two conjugates at the polypeptide-encoding sequences, the primer sequences, and/or the UTRs on the polypeptide-polynucleotide conjugate. In certain aspects, the UTR region and the region encoding the peptide tag for purification is common among a set of polypeptide-cDNA conjugates. In some embodiments, the common region is about 10, about 20, about 30, about 40, about 50, about 60, about 70, about 80, about 90, about 100, about 110, about 120, about 130, about 140, about 150, about 160, about 170, about 180, about 190, about 200 nucleotides in length. In other embodiments, this common region is longer than about 200 nucleotides in length. In other embodiments, the polypeptide-encoding region is about 10, about 20, about 30, about 40, about 50, about 60, about 70, about 80, about 90, about 100, about 110, about 120, about 130, about 140, about 150, about 160, about 170, about 180, about 190, about 200 nucleotides in length. In other embodiments, the polypeptide-encoding region is longer than about 200 nucleotides in length. In yet other embodiments, the total length of the common region and the polypeptide-encoding region is about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, or more than about 400 nucleotides. In other aspects, the total length of the common region and the polypeptide-encoding region is between about 80 and about 140 nucleotides in length.

Methods of producing arrays of the polypeptide-polynucleotide conjugates are also disclosed. In one embodiment, sets of nucleic acids synthesized on a substrate surface (e.g., a planar substrate or a set of beads) are utilized. In certain embodiments, nucleic acids of known sequence encoding amino acid sequences, for example, the primer sequence and the identifying sequence of a polypeptide-polynucleotide conjugate of the present disclosure, are synthesized directly onto the surfaces, e.g., using chemical synthesis techniques. The identity of the sequences at each different location or site on the array may be predetermined or determined following synthesis on the solid substrate or assembly (e.g., in the case of beads) into a fixed format, such as a microarray. The sequence identities may also be determined after construction of the polypeptide-polynucleotide conjugate array. Following the synthetic production of the nucleic acids, additional nucleic acids comprising desired sequence information (e.g., sequences encoding elements of the polypeptide-polynucleotide conjugate such as affinity tags, sequences necessary for transcription or translation, engaging sequences, and the like) are attached to the synthesized nucleic acids on the substrate surface using methods such as chemical and/or enzymatic ligation, primer extension, amplification, etc. The resultant polynucleotide portions are used as templates for the production of the polypeptide portions of the polypeptide-polynucleotide conjugates, via in vitro transcription and translation. It is also envisaged that the polypeptide portion and the polynucleotide portion of the conjugate can be prepared separately and then joined, for example, using chemical synthesis, recombinant technology, peptide and nucleic acid chemistry, or any combination thereof. In other embodiments, the primer sequence, the identifying sequence, and the engaging sequence can be prepared separately in any suitable sequence, and joined to form the polynucleotide portion of the conjugate. In certain embodiments, the polynucleotide portion can be synthesized to have each of these elements, or the polynucleotide portion can be constructed on the substrate by addition of the various elements to an initial oligonucleotide associated with the substrate surface.

In some aspects, polypeptide-polynucleotide conjugates are arrayed on a substrate. It is also within the present disclosure that in certain embodiments, the polypeptide portion and the polynucleotide portion are not directly physically linked, e.g., by conjugation. For example, a polypeptide and a polynucleotide can be independently immobilized on a substrate in physical proximity (e.g., at the same location in an array). Even though there is no direct physical linkage between the polypeptide and polynucleotide, they can function together as a polypeptide-polynucleotide conjugate disclosed herein due to physical proximity or association with the same location in an array. For example, binding of an analyte to the immobilized polypeptide would allow a polypeptide-polynucleotide conjugate provided in solution to be brought into proximity with the immobilized polynucleotide on the substrate. In some aspects, the flexibility afforded by being able to attach the polynucleotide and polypeptide separately to the substrate rather than to each other can be an advantage when forming an array. The polypeptide and the polynucleotide can be independently immobilized, substantially concurrently or sequentially, on the substrate. In certain aspects, ordered molecule deposition and/or a microfluidic device are used to achieve co-localization or physical proximity between the polypeptide and the polynucleotide immobilized on the substrate.

In certain embodiments, a polynucleotide array comprising all or a portion of the polynucleotide portions of a set of polypeptide-polynucleotide conjugates is generated first. Methods of generating polynucleotide arrays include and are not limited to production of arrays using the Affymetrix GeneChip technology (Affymetrix, Santa Clara, Calif.), including techniques disclosed in U.S. Pat. Nos. 7,736,906, 7,691,330, 7,547,775, 5,744,305, 5,677,195, 5,143,854 and U.S. Patent Application Publication Nos. 2010/0305006 and 2009/0192050; Agilent microarray technologies (Agilent Technologies, Inc., Santa Clara, Calif.), including but not limited to techniques disclosed in U.S. Pat. Nos. 7,642,097, 7,588,889, 656,740; 6,613,893; 6,599,693; 6,589,739; 6,587,579; 6,420,180; 6,387,636; 6,309,875; 6,232,072; 6,221,653; and 6,180,351 and U.S. Patent Application Publication No. 2006/0078889; Illumina) microarray technology (Illumina, Inc., San Diego, Calif., including but not limited to synthesis techniques disclosed in disclosed in U.S. Pat. Nos. 6,942,968, 6,858,394, 6,770,441, 6,429,027; and other synthesis techniques such as those disclosed in U.S. Pat. Nos 5,807,522, 5,700,637 and 5,445,934 and US Appln No. 2004/0259146. The arrays can be produced on a planar surface, or on a series of discrete surfaces, e.g., beads, that together form an array. The polypeptide-polynucleotide array can then be produced using any single-stranded or double-stranded polynucleotide arrays. In one embodiment, polypeptide portions of the conjugates are produced from the arrayed polynucleotide portions via in vitro transcription and translation, wherein the produced polypeptide portions are conjugated to the arrayed polynucleotide portions, forming a polypeptide-polynucleotide array. In other embodiments, polypeptide portions are prepared separately and then attached to the arrayed polynucleotide portions to form the polypeptide-polynucleotide array.

Other suitable methods for polynucleotide array production can be found, for example, in U.S. Pat. No. 7,556,919, issued July 2009 to Chenchik et al.; U.S. Pat. No. 7,291,471 issued November 2007 to Sampson et al.; U.S. Pat. No. 6,294,336, issued September 2001 to Boyce-Jacino et al.; U.S. Pat. No. 6,291,183, issued September 2001 to Pirrung et al.; U.S. Pat. No. 6,284,497 issued September 2001 to Sabanayagam et al.; U.S. Pat. No. 6,261,776 issued July 2001 to Pirrung et al.; U.S. Pat. No. 6,222,030 issued April 2001 to Dellinger et al.; U.S. Pat. No. 6,087,112, issued July 2000 to Dale; U.S. Pat. No. 6,077,674 issued June 200 to Schliefer and May; U.S. Pat. No. 5,919,523 issued July 1999 to Sundberg et al.; U.S. Pat. No. 5,861,242 issued January 1999 to Chee et al.; U.S. Pat. No. 5,856,174 issued January 1999 to Lipshutz et al; U.S. Pat. No. 5,837,832 issued November 1998 to Chee et al.; U.S. Pat. No. 5,770,722, issued June 19989 to Lockhart et al; U.S. Pat. No. 5,750,669, issued May 1998 to Rosch et al; U.S. Pat. No. 5,843,655 issued December 1998 to McGall; U.S. Pat. No. 5,723,320 issued March 1998 to Dehlinger; U.S. Pat. No. 5,695,940 issued December 1997 to Drmanac et al.; U.S. Pat. No. 5,631,724 issued May 1997 to Stem et al.; U.S. Pat. No. 5,556,752 issued September 1996 to Lockhart et al.; U.S. Pat. No. 5,525,464 issued July 1996 to Drmanac et al; U.S. Pat. No. 5,492,806 issued February 1996 to Drmanac et al; and U.S. Pat. No. 5,436,327 issued July 1995, all of which are incorporated by reference in their entireties for all purposes.

In certain embodiments, a substrate of the present disclosure can be porous or nonporous. In one aspect, a porous substrate is used for achieving higher surface loading than a nonporous substrate. Suitable substrates include substrates composed of materials such as glass, polyacrylamide-coated glass, ceramics, silica, silicon, quartz, various plastics, and the like. In one aspect, the substrate is a bead. In another aspect, the substrate is a planar surface. In certain embodiments, the planar surface is in the range of from about 0.02 $cm^2$ to about 20 $cm^2$ or even larger. The limit on substrate size is based on the detection methods used and the ability to resolve (e.g., in the case of fluorescent markers, the ability to optically resolve) the different constructs/conjugates and/or regions of constructs/conjugates on the surface. As detection methods continue to improve, substrate size may increase.

The format of the substrates of the present disclosure includes substantially planar surfaces as well as substrates with introduced variations to the substrate surface, e.g., depressions, wells, pedestals and the like. Such substrates are generally comprised of a material or group of materials having a rigid or semi-rigid surface or surfaces. In certain aspects, it is desirable to physically separate regions on an array with, for example, wells, raised regions, pedestals, etched holes, or the like. Such substrates can be produced, e.g., using multi-layer coating technologies or other techniques in the art. Examples of techniques for production of pattered arrays includes thermal and/or electron beam vapor deposition, replication, transfer, or film deposition; the CVD-type processes (LPCVD, PECVD, etc.); PVD-type processes such as sputtering, e.g., DC magnetron sputtering; ion-assisted deposition processes and sol-gel processes. Layers of substrate are optionally transferred onto the base by bonding or molecular adhesion.

In different aspects of the present disclosure, linkers may be used to attach the polypeptide-polynucleotide conjugates to a surface. Numerous types of linkers can be used, and the linker will generally be selected based on the type of construct, (amino acid, nucleic acid, etc.), the desired properties of the linker (length, flexibility) and other similar characteristics. Such linkers may comprise nucleotides, polypeptides, or a suitable synthetic material. The linker structures are preferably hydrocarbon base polymers which are comprised of biocompatible polymeric materials (e.g., polyethylene glycol). In certain aspects, the linkers used herein comprise one or more cleavable sites, to allow manipulation of the stability of the various complexes disclosed herein, for example, the ternary complex comprising the first polypeptide-polynucleotide conjugate, the analyte, and the second polypeptide-polynucleotide conjugate. In other aspects, the first and second polypeptide-polynucleotide conjugates form a complex, with or without attachment to the substrate. Cleavable linkers can be used to link the first and second polypeptide-polynucleotide conjugates, and/or link the conjugates and the substrate.

In certain aspects, the surface-immobilized conjugates comprise a cleavable linker directly attached to the substrate that allows specific conjugates to be separated from the substrate. In some aspects, the cleavable linker will be the same or identical for all of the surface-immobilized conjugates. In other aspects, certain subsets of conjugates on the substrate will have the same cleavable linker, where this cleavable linker differs from the cleavable linkers used with the other subsets on the same substrate surface. This allows certain conjugates to be separated from the substrate when others are not.

In certain embodiments, the polypeptide-polynucleotide conjugate arrays are fabricated by ordered molecule deposition, in which the position of a molecule is specified prior to its transfer and association onto a substrate. In other embodiments, the polypeptide-polynucleotide conjugate arrays are fabricated by random molecule deposition, in which the position of the molecule is randomly allocated on the substrate. Random molecule deposition may be accomplished by inkjet printing or pin-spotting. In certain other aspects, molecules and reagents for arraying the polypeptide-polynucleotide conjugates are delivered to the surface of a substrate using one or more microfluidic devices. For example, a microfluidic system can be integrated into the substrate upon which the molecules and reagents are disposed, or externally attached on top of the substrate. Microfluidic passages for holding and carrying fluid may be formed on and/or above the planar substrate by a fluidics layer abutted to the substrate. In other embodiments, any suitable combination of an ordered molecule deposition method, a random molecule deposition method, and a method based on microfluidic device can be used to array the conjugates of the present disclosure. Methods for depositing molecules on an array, including random access methods and microfluidic device based methods, are disclosed in U.S. Patent Application No. US 2011/0245111, entitled "Spatially encoded biological assays," and in U.S. Application Ser. No. 61/839,320, entitled "Spatially encoded biological assays using a microfluidic device," the disclosures of which are incorporated herein by reference for all purposes.

In particular embodiments, the conjugates disclosed herein are deposited on a substrate at a density that minimizes the interaction between individual conjugates immobilized on the substrate, before or after analyte capture. In one aspect, the density of a set of first polypeptide-polynucleotide conjugates immobilized on the substrate is sufficiently low to minimize or eliminate engagement between the first polypeptide-polynucleotide conjugates, including engagement between the first engaging sequences of the first conjugates. Therefore, false positive assay signals resulting from "intra-set" engagement or co-localization between the first polypeptide-polynucleotide conjugates are minimized or eliminated. In another aspect, the spacing between individually immobilized first conjugates substantially eliminates simultaneous binding of an analyte molecule to any two immobilized first conjugates. For example, a set of first polypeptide-polynucleotide conjugates each comprising an epitope for specific binding of an antibody analyte is immobilized on a substrate. The density of the first polypeptide-polynucleotide conjugates is so low that binding of the same antibody molecule to two adjacent first polypeptide-polynucleotide conjugates is prevented. In this case, one variable region of each bivalent antibody binds to the epitope on a first polypeptide-polynucleotide conjugate immobilized on the surface, while the other variable region of the antibody is not occupied and is available for specific binding of a second polypeptide-polynucleotide conjugate provided in solution.

In certain embodiments, the density of the immobilized polypeptide-polynucleotide conjugate on a substrate is determined for each type of conjugate. For example, the longer a conjugate is, the lower the density should be in order to prevent co-localization or interaction between two immobilized polypeptide-polynucleotide conjugates. In certain aspects, increasing the spacing between the immobilized conjugates (i.e., lowering the density) increases the signal to background ratio of the presently disclosed assays.

In some embodiments, the polynucleotide conjugates of the present disclosure are deposited or immobilized on a substrate at an average density of about 1 molecule/$\mu m^2$, about 2 molecules/$\mu m^2$, about 3 molecules/$\mu m^2$, about 4 molecules/$\mu m^2$, about 5 molecules/$\mu m^2$, about 6 molecules/$\mu m^2$, about 7 molecules/$\mu m^2$, about 8 molecules/$\mu m^2$, about 9 molecules/$\mu m^2$, or about 10 molecules/$\mu m^2$. In other embodiments, the polynucleotide conjugates are deposited or immobilized at an average density of about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400, about 405, about 410, about 415, about 420, about 425, about 430, about 435, about 440, about 445, about 450, about 455, about 460, about 465, about 470, about 475, about 480, about 485, about 490, about 495, or about 500 molecules/$\mu m^2$ on a substrate. In other embodiments, the polynucleotide conjugates are deposited or immobilized at an average density of lower than about 1 molecule/$\mu m^2$, or at an average density of higher than about 500 molecules/$\mu m^2$ on a substrate. In yet other embodiments, the polynucleotide conjugates are deposited or immobilized on a substrate at an average density of about 1 molecule/$mm^2$, about 10 molecules/$mm^2$, about 50 molecules/$mm^2$, about 100 molecules/$mm^2$, about 150 molecules/$mm^2$, about 200 molecules/$mm^2$, about 250 molecules/$mm^2$, about 300 molecules/$mm^2$, about 350 molecules/$mm^2$, 400 molecules/$mm^2$, about 450 molecules/$mm^2$, about 500 molecules/$mm^2$, about 550 molecules/$mm^2$, about 600 molecules/$mm^2$, about 650 molecules/$mm^2$, about 700 molecules/$mm^2$, about 750 molecules/$mm^2$, about 800 molecules/$mm^2$, about 850 molecules/$mm^2$, about 900 molecules/$mm^2$, about 950 molecules/$mm^2$, or about 1000 molecules/$mm^2$. In still other embodiments, the polynucleotide conjugates are deposited or immobilized on a substrate at an average density between about $1\times10^3$ and about $0.5\times10^4$ molecules/mm², between about $0.5\times10^4$ and about $1\times10^4$ molecules/mm², between about $1\times10^4$ and about $0.5\times10^5$ molecules/mm², between about $0.5\times10^5$ and about $1\times10^5$ molecules/mm², between about $1\times10^5$ and about $0.5\times10^6$ molecules/mm², or between about $0.5\times10^6$ and about $1\times10^6$ molecules/mm². In other embodiments, the average density of the polynucleotide conjugates deposited or immobilized on a substrate can be, for example, between about 1 molecule/cm² and about 5 molecules/cm², between about 5 and about 10 molecules/cm², between about 10 and about 50 molecules/cm², between about 50 and about 100 molecules/cm², between about 100 and about $0.5\times10^3$ molecules/cm², between about $0.5\times10^3$ and about $1\times10^3$ molecules/cm², $1\times10^3$ and about $0.5\times10^4$ molecules/cm², between about $0.5\times10^4$ and about $1\times10^4$ molecules/cm², between about $1\times10^4$ and about $0.5\times10^5$ molecules/cm², between about $0.5\times10^5$ and about $1\times10^5$ molecules/cm², between about $1\times10^5$ and about $0.5\times10^6$ molecules/cm², or between about $0.5\times10^6$ and about $1\times10^6$ molecules/cm².

In some embodiments, the average spacing or distance between immobilized polynucleotide conjugates on a substrate is about 10 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, about 205 nm, about 210 nm, about 215 nm, about 220 nm, about 225 nm, about 230 nm, about 235 nm, about 240 nm, about 245 nm, about 250 nm, about 255 nm, about 260 nm, about 265 nm, about 270 nm, about 275 nm, about 280 nm, about 285 nm, about 290 nm, about 295 nm, about 300 nm, about 305 nm, about 310 nm, about 315 nm, about 320 nm, about 325 nm, about 330 nm, about 335 nm, about 340 nm, about 345 nm, about 350 nm, about 355 nm, about 360 nm, about 365 nm, about 370 nm, about 375 nm, about 380 nm, about 385 nm, about 390 nm, about 395 nm, or about 400 nm. In other embodiments, the average spacing or distance between immobilized polynucleotide conjugates on a substrate is between about 400 and about 450 nm, between about 450 and about 500 nm, between about 500 and about 550 nm, between about 550 and about 600 nm, between about 600 and about 650 nm, between about 650 and about 700 nm, between about 700 and about 750 nm, between about 750 and about 800 nm, between about 800 and about 850 nm, between about 850 and about 900 nm, between about 900 and about 950 nm, or between about between about 950 and about 1000 nm. In still other embodiments, the average spacing or distance between immobilized polynucleotide conjugates on a substrate is between about 1 and about 5 µm, between about 5 and about 10 µm, between about 10 and about 15 µm, between about 15 and about 20 µm, between about 20 and about 25 µm, between about 25 and about 30 µm, between about 30 and about 35 µm, between about 35 and about 40 µm, between about 40 and about 45 µm, between about 45 and about 50 µm, between about 50 and about 55 µm, between about 55 and about 60 µm, between about 60 and about 65 µm, between about 65 and about 70 µm, between about 70 and about 75 µm, between about 75 and about 80 µm, between about 80 and about 85 µm, between about 85 and about 90 µm, between about 90 and about 95 µm, or between about 95 and about 100 µm. In certain embodiments, even larger average spacing or distance between immobilized polynucleotide conjugates on a substrate (thus even lower average density immobilized polynucleotide conjugates on the substrate) can be used, for example, about 100 µm, about 200 µm, about 300 µm, about 400 µm, about 500 µm, about 600 µm, about 700 µm, about 800 µm, about 900 µm, about 1 mm, about 2 mm, about 3 mm, about 4 mm, about 5 mm, about 6 mm, about 7 mm, about 8 mm, about 9 mm, about 1 cm, or larger than about 1 cm.

In certain embodiments, the concentration of the conjugate provided in solution is controlled to reduce background and/or false positive results of the assay. In other embodiments, the ratio between the immobilized conjugate molecules and the soluble conjugate molecules is controlled to reduce background and/or false positive results of the assay. In other aspects, the density of the immobilized conjugates, the concentration of the soluble conjugates, and/or the ratio between the numbers of two conjugate molecules are such that non-specific binding is substantially reduced or eliminated, and at the same time, there are enough conjugate molecules (the immobilized or soluble conjugate, or both) to produce robust specific signals by specific analyte capture and detection.

In some embodiments, the concentration of a soluble conjugate used in the assay is about 0.0001 nM, about 0.001 nM, about 0.01 nM, about 0.1 nM, about 1 nM, about 2 nM, about 5 nM, about 10 nM, about 20 nM, about 50 nM, about 100 nM, about 200 nM, about 500 nM, or about 1000 nM. In other embodiments, the concentration of a soluble conjugate used in the assay is between about 0.0001 nM and about 0.001 nM, between about 0.001 nM and about 0.01 nM, between about 0.01 nM and about 0.1 nM, between about 0.1 nM and about 1 nM, between about 1 nM and about 2 nM, between about 2 nM and about 5 nM, between about 5 nM and about 10 nM, between about 10 nM and about 20 nM, between about 20 nM and about 50 nM, between about 50 nM and about 100 nM, between about 100 nM and about 200 nM, between about 200 nM and about 500 nM, between about 500 nM and about 1000 nM, or more than about 1000 nM.

In some embodiments, the ratio between the soluble conjugate molecules and the immobilized conjugate molecules used in the assay is about 0.00001:1, about 0.0001:1, about 0.001:1, about 0.01:1, about 0.1:1, about 1:1, about 2:1, about 5:1, about 10:1, about 15:1, about 20:1, about 25:1, about 30:1, about 35:1, about 40:1, about 45:1, about 50:1, about 55:1, about 60:1, about 65:1, about 70:1, about 75:1, about 80:1, about 85:1, about 90:1, about 95:1, about 100:1, or any ratio in between the above listed ratios.

5. Methods for Antibody Detection and Analysis

Also disclosed herein are methods for antibody detection and analysis. In one aspect, a method for analyzing an antibody or antigen binding fragment thereof in a sample, is disclosed. The method comprises immobilizing a first polypeptide-polynucleotide conjugate on a substrate. The first polypeptide-polynucleotide conjugate comprises a first polypeptide comprising a first epitope for specific binding of an antibody or antigen binding fragment thereof, and a first polynucleotide comprising a first primer sequence, a first identifying sequence that identifies the first polypeptide, and a first engaging sequence. The method further comprises contacting the substrate having the immobilized first polypeptide-polynucleotide conjugate with a sample containing or suspected of containing the antibody or antigen binding fragment thereof, whereby the first epitope specifically binds to the antibody or antigen binding fragment thereof in the sample. The method further comprises contacting the substrate having the immobilized first polypeptide-polynucleotide conjugate with a second polypeptide-polynucleotide conjugate. The second polypeptide-polynucleotide conjugate comprises a second polypeptide comprising a second epitope for specific binding of the antibody or antigen binding fragment thereof, and a second polynucleotide comprising a second primer sequence, a second identifying sequence that identifies the second polypeptide, and a second engaging sequence. The second epitope specifically binds to the antibody or antigen binding fragment specifically bound to the first epitope, such that the first and second polynucleotides and the antibody form a sandwich complex. The first and second polynucleotides are brought into proximity bind the antibody, and become engaged via the first and second engaging sequences. The method further comprises analyzing the first and/or second polynucleotides engaged via the first and second engaging sequences, for example, by determining the nucleic acid sequence of all or a portion of the first and/or second polynucleotides. In some aspects, analysis of the engaged nucleic acid sequences comprises primer extension, ligation, amplification (e.g., PCR amplification), and/or nucleic acid sequencing. The analysis indicates the presence, absence and/or amount of the antibody or antigen binding fragment thereof in the sample.

In one aspect of the present disclosure, the polynucleotide portions of the first and second polypeptide-polynucleotide conjugates are not PCR amplified unless they are joined together as a result of specific binding of polypeptide portions of the conjugates to the same analyte, e.g., an antibody. Proximity-dependent DNA ligation assay (PLA) has been used for protein target detection. See Darmanis et al., 2011, PLoS One 6, e25583; Flanigon et al., 2013, Nature Biotechnol. 30, 153-58, the disclosures of which are incorporated by reference. All components of PLA are present in one assay vial at the same time since both DNA tagged detection antibodies are added to a sample. This makes high multiplexing extremely difficult, due to the opportunity for non-specific interaction between the DNA tags. In one aspect, the presently disclosed methods utilize a plurality of first polypeptide-polynucleotide conjugates associated with a substrate, each of the first polypeptide-polynucleotide conjugates is separated from its neighbors by a distance sufficient to avoid interaction, and the set of second polypeptide-polynucleotide conjugates is added after analyte binding, e.g., after antibody capture by the first polypeptide-polynucleotide conjugates.

Figure 4:
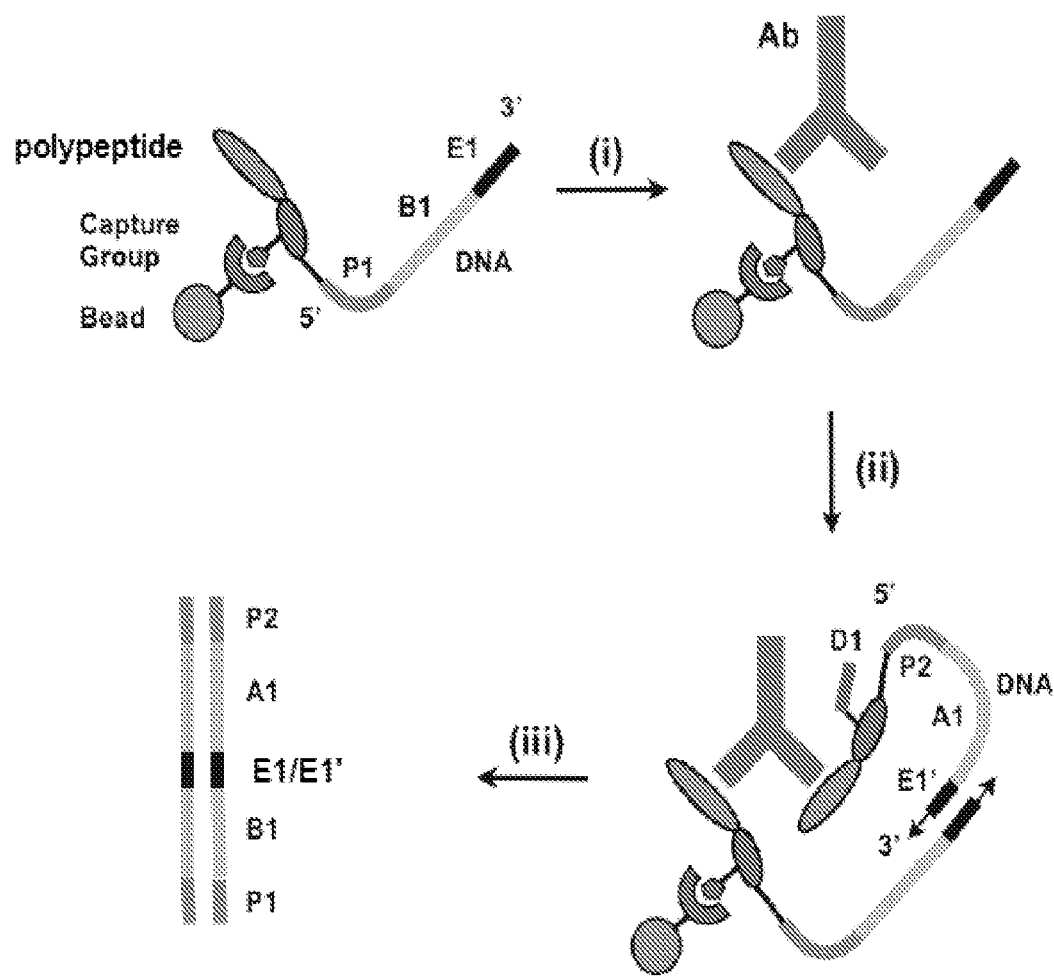
FIG. 4 is a schematic showing a method for analyzing an antibody according to one embodiment of the present disclosure.

One exemplary scheme is shown in FIG. 4. Provided in FIG. 4 is a first polypeptide-polynucleotide conjugate (e.g., a first polypeptide-DNA conjugate) immobilized on a substrate, for example, via biotin interaction with a streptavidin coated magnetic bead. It is to be understood that other methods for immobilizing the conjugate can be used, for example, by direct chemical synthesis on the substrate. Only one first polypeptide-DNA conjugate is shown in FIG. 4. However, it is envisaged that a library of first polypeptide-DNA conjugates can be immobilized on the surface, for instance, in an array format. Each individual first polypeptide-DNA conjugate of the library may be prepared separately according to the present disclosure. In other aspects, all or a portion of the library is produced, purified, and/or immobilized on the substrate in a batch format.

As shown in FIG. 4, in one aspect, each first polypeptide-DNA conjugate in the library comprises an affinity tag (e.g., an affinity tag that contains a biotin moiety) that is capable of being specifically captured by a capture group (e.g., a capture group containing a streptavidin moiety) on the substrate. In some embodiments, the affinity tag is at the C-terminus of the polypeptide portion of the polypeptide-DNA conjugate (as shown in FIG. 4), or at other suitable locations within the polypeptide-DNA conjugate. In certain embodiments, the affinity tag is common among the first polypeptide-DNA conjugates in the library. In other embodiments, different affinity tag/capture group combinations may be used among the first polypeptide-DNA conjugates in the library, such that subpopulations of the library can be distinguished from each other.

The first polypeptide-DNA conjugate shown in FIG. 4 also comprises a polypeptide portion that comprises an antigen region, for example, an epitope specific for an antibody of interest or antigen-binding fragment thereof. In certain embodiments, the polypeptide portion and/or the antigen region of a first polypeptide-DNA conjugate is specific to each conjugate, i.e., the polypeptide portion and/or the antigen region is substantially unique among the conjugates in the library. In other embodiments, the polypeptide portion and/or the antigen region can be common for at least two first polypeptide-DNA conjugates in the library. For example, the library may comprise two or more polypeptide-DNA conjugates having the same polypeptide portion and/or the antigen region, but with different affinity tags and capture agents or different DNA portions that contain identifying sequences that identify the polypeptide portions. In some aspects, this approach allows formation of arrays having internal control mechanisms, for example, to help identify false positives in an assay or to ensure that the specificity of the assay is not adversely affected by the process of constructing or using the array.

The DNA portion of the first polypeptide-DNA conjugate shown in FIG. 4 comprises a three regions, P1, B1, and E1. P1 is a primer sequence, for example, for amplification and/or sequencing of a primer extension product formed following engagement of the first and second engaging sequences. B1 is an identifying sequence that identifies the polpeptide portion of the conjugate. E1 is an engaging sequence. In one aspect, each of the n (n is an integer) first polypeptide-DNA conjugates in the library contains: (1) a primer sequence P1, which may be the same or different among the first conjugates; (2) an identifying sequence, i.e., B1, B2, . . . , Bn; and (3) an engaging sequence E1, which may be the same or different among the first conjugates.

In step (i) as shown in FIG. 4, the immobilized first polypeptide-DNA conjugate is contacted with a sample containing an antibody of interest, or a collection of antibodies of interest. Under suitable conditions, the bivalent antibody shown in FIG. 4 specifically binds to the polypeptide portion containing an epitope for the antibody. In one aspect, only one of the two antigen-binding regions of the antibody is occupied, leaving the other antigen-binding region available for specific binding of a second polypeptide-DNA conjugate.

In step (ii) of FIG. 4, a library of second polypeptide-DNA conjugates is provided, and is contacted with the substrate having the immobilized first polypeptide-DNA conjugate specifically bound to the antibody. In certain embodiments, a second polypeptide-DNA conjugate in the library has the same polypeptide portion and/or the antigen region as the immobilized first polypeptide-DNA conjugate. In one aspect, however, the second polypeptide-DNA conjugate comprises a DNA portion (P2-A1-E1') that is different from the first polypeptide-DNA conjugate (P1-B1-E1). P2 is a second primer sequence, for example, for amplification and/or sequencing of a primer extension product formed following engagement of the first and second engaging sequences. A1 is an identifying sequence that identifies the polpeptide portion of the second conjugate. E1' is an engaging sequence that is hybridizable to E1, for example, via sequence complementarity. In one aspect, each of the n second polypeptide-DNA conjugates in the library contains: (1) a primer sequence P2, which may be the same or different among the second conjugates; (2) an identifying sequence, i.e., A1, A2, . . . , An; and (3) an engaging sequence E1', which may be the same or different among the second conjugates. In certain embodiments, the first or second polypeptide-DNA conjugate further comprises a tag for purification, for example, tag D1 in FIG. 4 is attached to a common C-terminal tag and can be used for purification of full-length library members. In certain embodiments, the tag for purification is a short DNA fragment.

Binding of the second polypeptide-DNA conjugate to the remaining antigen-binding region of the antibody brings the first and second polypeptide-DNA conjugates in physical proximity For example, the first and second polypeptide-DNA conjugates and the antibody form a ternary "sandwich" complex, allowing the first engaging sequence E1 and the second engaging sequence E1' to engage. In step (iii) of FIG. 4, E1 and E1' serve as "primers" for extension, using the DNA portion of the second conjugate and the DNA portion of the first conjugate, respectively, as templates. In one embodiment, primer extension is catalyzed by a DNA polymerase in the 5' to 3' direction. In one aspect, as shown in FIG. 4, the primer extension product is a double-stranded DNA construct (P1-B1-E1-A1-P2), resulting in permanent association of the identifying sequences B1 and A1. The DNA construct and/or its complement can be amplified and sequenced, for example, using sequence information from one or both of the primer sequences P1 and P2. The assay can be easily multiplexed. For example, each first polypeptide and second polypeptide pair can be uniquely identified by a corresponding identifying sequence pair (e.g., B1-A1, B2-A2, . . . , Bn-An). In one aspect, qPCR with pair specific primers can be used to detect and/or quantify the primer extension product.

In certain aspects, the first or second engaging sequence can be blocked at the 3' terminus or designed in a way that prohibits extension of the DNA portion of the first and second conjugate, respectively. For example, E1 or E1' can include dideoxynucleotides or 3' modifications, such that extension by a polymerase is blocked. Thus, in one aspect, the primer extension product is generated by extending the first engaging sequence only or the second engaging sequence only.

The primer extension product can be analyzed to determine the absence, presence, or amount of the antibody in the sample. All or a portion of the sequence of the primer extension product can be determined. In one aspect, the primer extension product is amplified and/or sequenced. Sequence information of the first primer P1 and/or the second primer P2 can be used for the amplification and/or sequencing.

In certain embodiments, the primer extension products are subjected to high-throughput, next-generation sequencing, or highly parallel next-generation sequencing methods. Suitable sequencing technologies include but are not limited to SOLiD™ technology (Life Technologies, Inc.), HiSeq, MiSeq, or Genome Analyzer (all from Illumina, Inc.). Such next-generation sequencing methods can be carried out, for example, using a one pass sequencing method or using paired-end sequencing. Next generation sequencing methods include, but are not limited to, hybridization-based methods, such as disclosed in e.g., Drmanac, U.S. Pat. Nos. 6,864,052; 6,309,824; and 6,401,267; and Drmanac et al., U.S. patent publication 2005/0191656; sequencing-by-synthesis methods, e.g., U.S. Pat. Nos. 6,210,891; 6,828,100; 6,969,488; 6,897,023; 6,833,246; 6,911,345; 6,787,308; 7,297,518; 7,462,449 and 7,501,245; US Publication Application Nos. 20110059436; 20040106110; 20030064398; and 20030022207; Ronaghi, et al., Science, 281:363-365 (1998); and Li, et al., Proc. Natl. Acad. Sci., 100:414-419 (2003); ligation-based methods, e.g., U.S. Pat. Nos. 5,912, 148 and 6,130,073; and U.S. Pat. Appln Nos. 20100105052, 20070207482 and 20090018024; nanopore sequencing, e.g., U.S. Pat. Appln Nos. 20070036511; 20080032301; 20080128627; 20090082212; and Soni and Meller, Clin Chem 53:1996-2001 (2007), as well as other methods, e.g., U.S. Pat. Appln Nos. 20110033854; 20090264299; 20090155781; and 20090005252; also, see, McKernan, et al., Genome Res. 19:1527-41 (2009) and Bentley, et al., Nature 456:53-59 (2008), all of which are incorporated herein in their entireties for all purposes.

In certain aspects, allowing the first and second polypeptide-polynucleotide conjugates to form a transient conjugate complex before binding of the antibody analyte increases capture efficiency and/or affinity, when compared to sequential interaction, e.g., interaction between the antibody and the first conjugate followed by interaction between the second conjugate and the antibody/first conjugate complex. In particular examples, methods employing pre-formed transient complexes between the first and second conjugates are used for detection and/or analysis of low affinity antibodies, for example, antibodies with a low binding constant for an epitope. This approach is particularly useful when the concentration of the antibody analyte in a sample is low, for example, when the antibody concentration is close to or below about the inverse value of the antibody's binding constant.

In one aspect, a transient conjugate complex is formed through polynucleotide hybridization between the polynucleotide portions of the first and second polypeptide-polynucleotide conjugates. In certain aspects, conditions favoring high stability, such as low temperatures and high salt concentrations, are used to promote formation of the transient conjugate complex before antibody binding. Similar conditions are used for the antibody to bind to the transient conjugate complex, the two antigen-binding regions (e.g., the variable regions of the antibody) specifically binding to the polypeptide portions of the first and second conjugates, respectively. In certain aspects, conditions are used to maintain the integrity of the antibody, and the sample containing the antibody (e.g., a serum sample). In certain embodiments, conditions are chosen to avoid or reduce protein precipitation in the sample. Upon antibody binding and formation of the ternary complex, washing can be performed under conditions where DNA hybridization is significantly weakened while protein/protein interaction is substantially not affected. For example, interaction between the antibody and the epitopes on the first and second polypeptide-polynucleotide conjugates is substantially not affected, and serves to maintain stability of the ternary complex. Exemplary washing conditions include low salt concentration buffers, elevated temperature (37° C. to 40° C.), and buffers with low concentrations of DMSO or formamide. Under such conditions, polypeptide-polynucleotide conjugate complexes that are maintained solely by polynucleotide hybridization are destabilized, and the second polypeptide-polynucleotide conjugate not specifically bound by the antibody (e.g., bound to the antibody outside the variable region) can be washed away. Thus, assay signals resulting from non-specific binding can be reduced. On the other hand, the second polypeptide-polynucleotide conjugate specifically bound by the antibody (i.e., bound to the variable region of the antibody) remain in the ternary complex. Next, conditions that favor polynucleotide hybridization and maintain specific protein/protein interactions can be used to allow the first and second engaging sequences to hybridize, for subsequent primer extension and production of an extension product that results from specific binding of the antibody.

In another aspect, a transient conjugate complex is formed through polynucleotide hybridization between the polynucleotide portions of the first and second polypeptide-polynucleotide conjugates. Conditions favoring high stability are used to promote formation of the transient conjugate complex before antibody binding, and for the antibody to bind to the transient conjugate complex. In this example, one or more cleavable sites are introduced into the polynucleotide involved in hybridization in order to regulate stability of the transient conjugate complex. One example of the cleavable sites are dU-containing residues introduced into DNA. In one aspect, upon antibody binding, the cleavable sites in the hybridized sequences are cleaved, for example, by treating with UDG in combination with DNA glycosylase-lyase Endonuclease VIII, to shorten sequences involved in hybridization and thus destabilize the transient conjugate complex. In this example, a washing step can be used to wash away the second polypeptide-polynucleotide conjugate not specifically bound by the antibody, thereby reducing assay signals resulting from non-specific binding. On the other hand, the second polypeptide-polynucleotide conjugate specifically bound by the antibody remain in the ternary complex during the wash. Washing conditions that weaken polynucleotide hybridization and maintain specific protein/protein interaction can be used in combination with the cleavage of the hybridization sequences. After washing away non-specifically bound second polypeptide-polynucleotide conjugates, conditions that favor polynucleotide hybridization and maintain protein/protein interactions can be used to allow the first and second engaging sequences to hybridize. In cases where the engaging sequences are cleaved by UDG at the 3' end before the washing step, the cleaved engaging sequences can be dephosphorylated (e.g., by a polynucleotide kinase) to allow extension by a polymerase. The first and/or second engaging sequences can be blocked at the 3' ends to prevent primer extension. Thus, only the cleaved engaging sequences can result in a primer extension product, indicative of specific binding of the conjugates to the antibody analyte.

In another embodiment, a transient conjugate complex is formed through polynucleotide hybridization between the polynucleotide portions of the first and second polypeptide-polynucleotide conjugates. Similar to the above embodiments, conditions favoring high stability are used to promote formation of the transient conjugate complex before antibody binding, and for the antibody to bind to the transient conjugate complex. In this case, the second polypeptide-polynucleotide conjugate is attached to the support by a cleavable linker. In one aspect, the cleavable linker is introduced after the first and second polypeptide-polynucleotide conjugates are brought into proximity through polynucleotide hybridization. In another aspect, the first and second polypeptide-polynucleotide conjugates are deposited in proximity on the substrate, before and independent of polynucleotide hybridization. In yet another aspect, the first and second polypeptide-polynucleotide conjugates are allowed to form a transient conjugate complex via polynucleotide hybridization, before the complex is deposited on the substrate. Upon antibody binding, the cleavable linker is cleaved to release the second polypeptide-polynucleotide conjugates not specifically bound by the antibody. A washing step can be used to wash away the second polypeptide-polynucleotide conjugate not specifically bound by the antibody, thereby reducing assay signals resulting from non-specific binding. On the other hand, the second polypeptide-polynucleotide conjugate specifically bound by the antibody remain in the ternary complex during the wash. Washing conditions that weaken polynucleotide hybridization and maintain protein/protein interaction can be used in combination with the cleavage of the linker. After the washing step, conditions that favor polynucleotide hybridization and maintain protein/protein interactions are used to allow the first and second engaging sequences to hybridize.

In yet another embodiment, a transient conjugate complex formed through polynucleotide hybridization between the polynucleotide portions of the first and second polypeptide-polynucleotide conjugates, and by a cleavable linker between the first and second polypeptide-polynucleotide conjugates. Similar to the above embodiments, conditions favoring high stability are used to promote formation of the transient conjugate complex before antibody binding, and for the antibody to bind to the transient conjugate complex. In one aspect, the cleavable linker is introduced after the first and second polypeptide-polynucleotide conjugates are brought into proximity through polynucleotide hybridization. In another aspect, the cleavable linker is introduced between the first and second polypeptide-polynucleotide conjugates before deposition on the substrate. Upon antibody binding, the cleavable linker is cleaved to release the second polypeptide-polynucleotide conjugates not specifically bound by the antibody. A washing step can be used to wash away the second polypeptide-polynucleotide conjugate not specifically bound by the antibody, thereby reducing assay signals resulting from non-specific binding. On the other hand, the second polypeptide-polynucleotide conjugate specifically bound by the antibody remain in the ternary complex during the wash. Washing conditions that weaken polynucleotide hybridization and maintain specific protein/protein interaction can be used in combination with the cleavage of the linker. After the washing step, conditions that favor polynucleotide hybridization and maintain specific protein/protein interactions are used to allow the first and second engaging sequences to hybridize.

Figure 5:
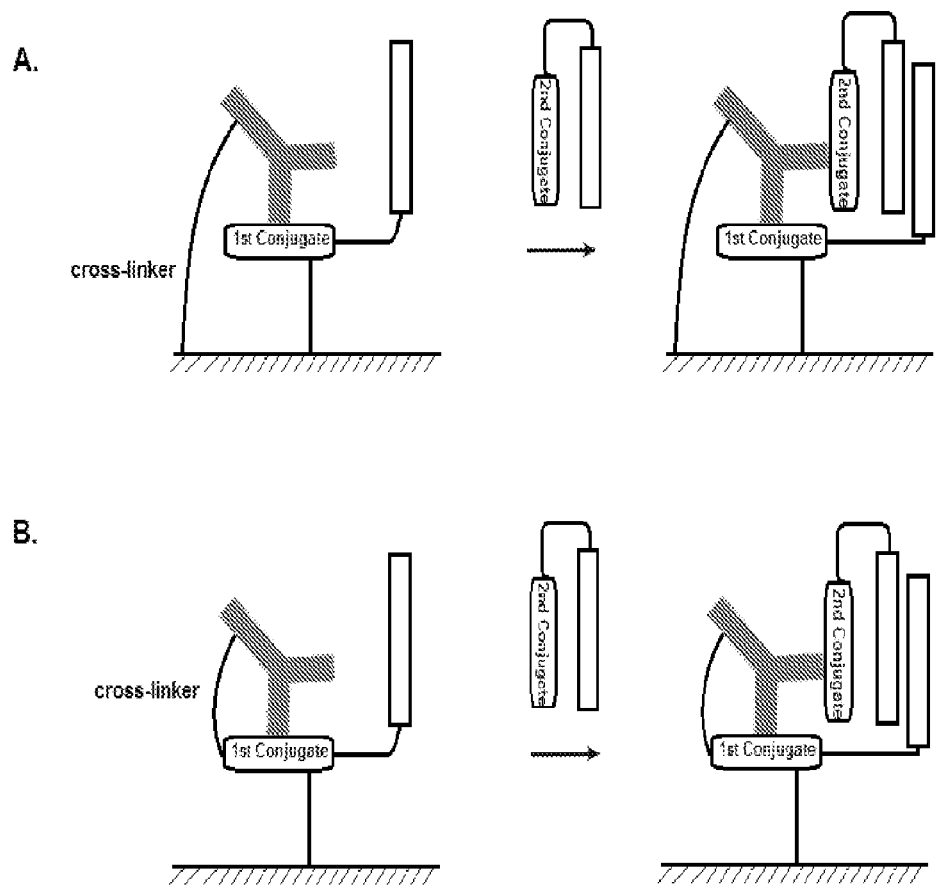
FIGS. 5A-5B are schematics demonstrating methods for analyzing an antibody according to some embodiments of the present disclosure.

In any of the preceding embodiments, a method disclosed herein can further comprise a step of cross-linking an antibody analyte specifically bound by a first polypeptide-polynucleotide conjugate to the conjugate, and/or cross-linking the antibody analyte to the substrate where the conjugate is immobilized. For example, upon antibody binding to an immobilized first polypeptide-polynucleotide conjugate and after washing away unbound components in a sample (e.g., other antibodies in the sample that do not specifically bind to the first polypeptide-polynucleotide conjugate), the specifically bound antibody analyte can be cross-linked, as shown in FIG. 5A and FIG. 5B. In certain aspects, the cross-linking is stable. In other aspects, the cross-linking is reversible or irreversible. In certain embodiments, by cross-linking, the antibody analyte is secured in the physical proximity of the first polypeptide-polynucleotide conjugate to which it is specifically bound. The analyte and the first polypeptide-polynucleotide conjugate, now co-localized or in close physical proximity, are available for a second polypeptide-polynucleotide conjugate to bind and form a ternary complex. In one aspect, even when the second polypeptide-polynucleotide conjugate is provided in excess and is capable of displacing the antibody specifically bound to the first polypeptide-polynucleotide conjugate, the antibody and the first conjugate is still secured in physical proximity by cross-linking (e.g., cross-linking the antibody to the first conjugate or to the substrate). In certain embodiments, even when the binding between the antibody and the first polypeptide-polynucleotide conjugate is disturbed, the cross-linking agent/linker is still capable of securing the antibody and the first conjugate in physical proximity, allowing the second polypeptide-polynucleotide conjugate to bind and the first and second engaging sequences to engage and be extended by a polymerase.

A number of approaches can be used for cross-linking. In one aspect, the antibody is covalently cross-linked to the substrate and/or first polypeptide-polynucleotide conjugate using a bi-functional protein reactive cross-linking reagent, for example, paraformaldehyde, glutaraldehyde, bis-NHS-linkers. In another aspect, the antibody is cross-linked by using a covalent/affinity linking reagent, e.g., NHS-linker-biotin. For instance, the biotin moiety binds to the substrate which comprises streptavidin moieties, and the NHS moiety cross-links to the antibody. In yet another aspect, the antibody is cross-linked by using a reagent having affinity to both the antibody and the substrate, for example, a biotinylated anti-Fc antibody. In this case, the anti-Fc antibody recognizes and binds to Fc region of the analyte antibody and the biotin moiety binds to the substrate comprising streptavidin moieties. In still other aspects, the antibody is cross-linked by an on demand activable reactive reagent. In one embodiment, the first polypeptide-polynucleotide conjugate further comprises an on demand activable reactive moiety. In some embodiments, reactive moiety is activated only upon antibody binding to the first polypeptide-polynucleotide conjugate, for example, forming a covalent bond with the bound antibody. Examples of the activable reactive reagent include photoactivable molecules such as aryl azide and benzophenone reagents. In other aspects, any suitable combination of the cross-linking methods described herein can be used.

In some embodiments, a bivalent or multivalent second polypeptide-polynucleotide conjugate is used in a method disclosed herein. For example, a bivalent second polypeptide-polynucleotide conjugate comprises two polypeptide portions, each comprising an epitope for specific binding to an antigen-binding region of the antibody. In one aspect, the two polypeptide portions of the bivalent conjugate are identical or comprise the same epitope for antibody binding. In another aspect, the two polypeptide portions of the bivalent conjugate are different (e.g., comprising different epitopes) and each specifically binds to an antigen-binding region of a bispecific antibody, a bispecific scFv (bis-scFV), or a diabody.

Figure 6:
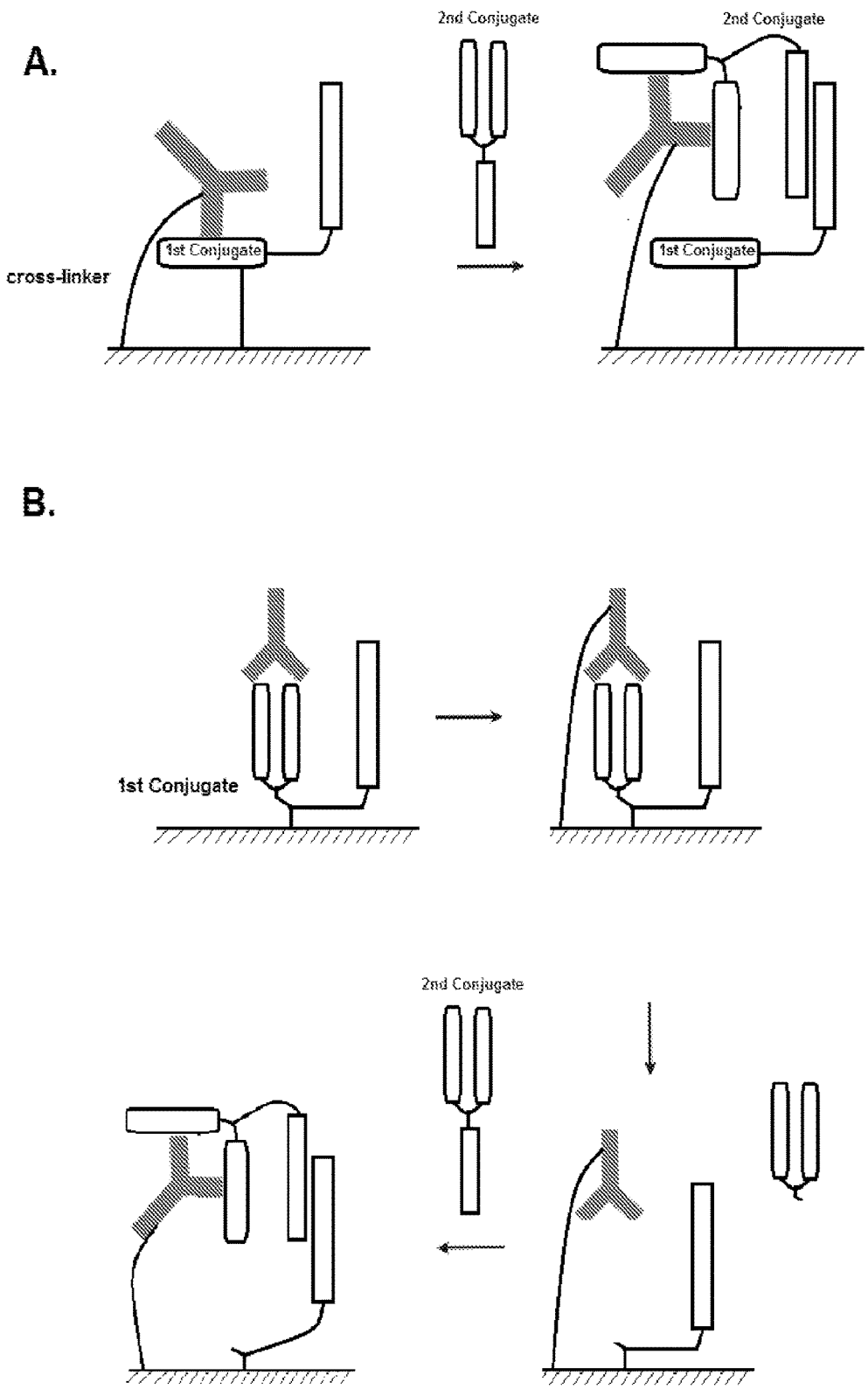
FIG. 6A and FIG. 6B are schematics showing methods for analyzing an antibody according to some embodiments of the present disclosure.

In the example shown in FIG. 6A, upon antibody binding to the immobilized first polypeptide-polynucleotide conjugate, the antibody is cross-linked to the substrate and is secured in physical proximity to the first conjugate. A bivalent second polypeptide-polynucleotide conjugate is provided to displace the antibody specifically bound to the first conjugate. Even though the interaction between the antibody and the first conjugate is disrupted, they are secured in physical proximity by the cross-linker. The bivalent second polypeptide-polynucleotide conjugate can specifically bind one or both of the antigen-binding regions of the antibody. In one aspect, a bivalent polypeptide-polynucleotide conjugate has a higher affinity to the antibody than a monovalent polypeptide-polynucleotide conjugate. In another aspect, a bivalent polypeptide-polynucleotide conjugate displaces antibody binding more easily than a monovalent conjugate. Therefore, fewer molecules of the bivalent polypeptide-polynucleotide conjugate can be used compared to a monovalent conjugate, thus reducing the background of the assay. After binding of the bivalent second polypeptide-polynucleotide conjugate to the antibody, the complex between the second conjugate and the antibody is secured in physical proximity to the first conjugate immobilized on the substrate as shown in FIG. 6A, even though there is no antibody-epitope interaction between the antibody and the first conjugate. Thus, the first and second engaging sequences can bring the two polynucleotide portions together for primer extension.

In the example shown in FIG. 6B, an immobilized bivalent first polypeptide-polynucleotide conjugate is used to capture the antibody analyte. In one aspect, this approach is particularly suitable for capturing a low affinity antibody, because the bivalent conjugate binds to both antigen-binding regions of the antibody and thus binds to the antibody with a higher affinity than a monovalent conjugate. Upon antibody capture, the antibody is cross-linked to the substrate and is secured in physical proximity to the first conjugate. The polypeptide portions of the bivalent first conjugate can then be cleaved, for example, at one or more enzyme-cleavable sites within the first conjugate. The cleaved polypeptide portions are released, while the polynucleotide portion of the first conjugate remains attached to the substrate, in proximity to the cross-linked antibody analyte. In certain aspects, conditions favoring dissociation between the bound first epitopes and antigen-binding regions are used, allowing the cleaved polypeptide portions to be released and washed away. In one aspect, such dissociation can be easily achieved due to the low antigen-binding affinity of the antibody analyte. For example, one of the standard antibody purification techniques uses low pH elution to elute antibodies from a column with immobilized antigens. A bivalent second polypeptide-polynucleotide conjugate is then provided. Even though the interaction between the antibody and the first conjugate is disrupted, the antibody and the polynucleotide portion of the first conjugate are secured in physical proximity The bivalent second polypeptide-polynucleotide conjugate can specifically bind to one or both of the antigen-binding regions of the antibody. After binding of the bivalent second polypeptide-polynucleotide conjugate to the antibody, the complex between the second conjugate and the antibody is secured in physical proximity to the polynucleotide portion of the first conjugate, which remains immobilized on the substrate as shown in FIG. 6B, even though there is no antibody-epitope interaction between the antibody and the first conjugate. Thus, the first and second engaging sequences can bring the two polynucleotide portions together for primer extension.

In one aspect, disclosed herein is a method for detecting a multivalent antibody or antibody complex. For example, multimeric antibodies such as IgA and IgM can be detected. In one aspect, a bivalent or multivalent polypeptide-polynucleotide conjugate is immobilized on a substrate. For example, the conjugates shown in FIG. 2E can be used. In one aspect, the bivalent or multivalent conjugates are attached to the substrate at a sufficiently low density, for example, a single antibody could interact with both polypeptides of a bivalent conjugate but not with any neighboring conjugates. In the case of an immobilized bivalent conjugate, the two antigen-binding sites of one of antibody subunits of an IgM molecule can bind to the two polypeptide portions of the conjugate, respectively. The remaining antigen-binding sites of the IgM are available to bind the second conjugate provided in solution. In certain aspects, the second conjugate can be monovalent or bivalent, and in one embodiment, the latter has higher affinity for the IgM molecule.

In other embodiments, a bivalent or multivalent polypeptide-polynucleotide conjugate can have a single polynucleotide portion, or multiple polynucleotide portions. In one aspect, a bivalent or multivalent conjugate can be formed by linking two or more monovalent conjugates together.

In one aspect, the bivalent or multivalent polypeptide-polynucleotide conjugate increases the avidity of the interaction with an antibody, allowing capture of lower affinity antibodies. This is important since IgM typically has lower affinity than IgG. Multimeric antibodies (e.g., IgA and IgM) would still have 2 or 8 antigen-binding sites available for a second conjugate to bind, while IgG, IgE and IgD would not have any remaining antigen-binding sites to capture a second conjugate. This would give specificity for multimeric antibodies. Thus, in one embodiment, a bivalent or multivalent polypeptide-polynucleotide conjugate can be used to suppress signals from IgG, IgE, and/or IgD molecules, and to specifically detect multimeric antibodies such as IgM.

In addition to the first and second polypeptide-polynucleotide conjugates, in certain embodiments, a method of the present disclosure comprises the use of a third polypeptide-polynucleotide conjugate. In one aspect, the first and second polypeptide-polynucleotide conjugates specifically bind to the antigen-binding regions of an antibody analyte, and the third conjugate specifically binds to the antibody in a region other than the antigen-binding regions, for example, the constant regions, the hinges regions, or the Fc region.

Figure 7:
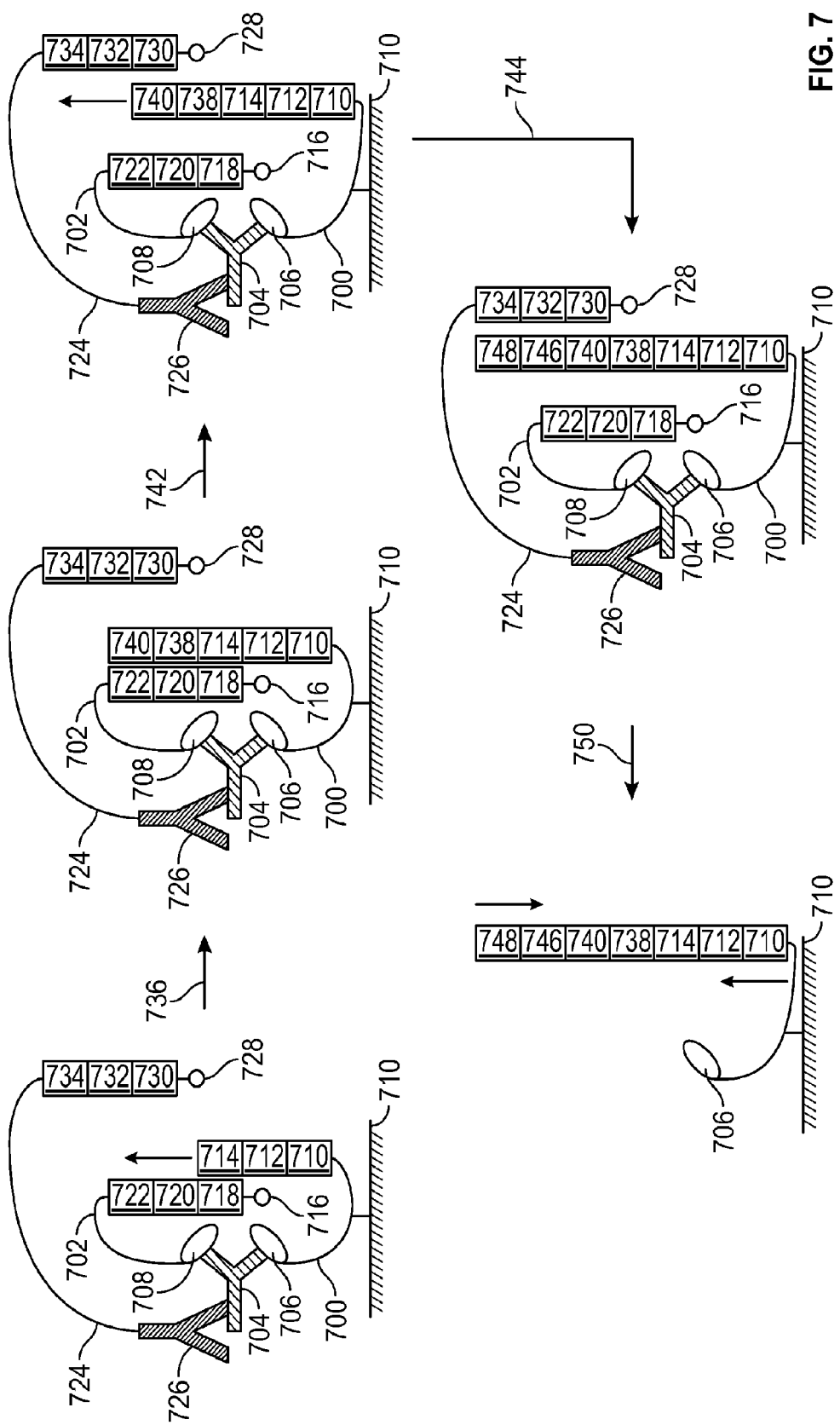
FIG. 7 is a schematic showing a method for analyzing an antibody according to one embodiment of the present disclosure.

In the example shown in FIG. 7, a first polypeptide-polynucleotide conjugate 700, a second polypeptide-polynucleotide conjugate 702, and an antibody 704 form a ternary complex, through specific binding of the first polypeptide portion 706 and the second polypeptide portion 708 to the two antigen-binding regions of the antibody, respectively. In one aspect, the first polypeptide-polynucleotide conjugate is immobilized on a substrate. In this example, the first polypeptide-polynucleotide conjugate comprises a primer sequence 710, an identifying sequence 712 that identifies the first polypeptide portion 706, and an engaging sequence 714, and the second polypeptide-polynucleotide conjugate comprises a 3' blocker 716 that blocks primer extension, an engaging sequence 718, an idiotype extension/coding sequence 720, and an isotype extension sequence 722. As shown in FIG. 7, the first engaging sequence 714 and the second engaging sequence 718 are hybridizable to each other and the engaged sequences are subject to primer extension. In this example, since the second engaging sequence is blocked at the 3' end (by blocker 716), only the polynucleotide portion of the first conjugate is extended by a polymerase using the polynucleotide portion of the second conjugate as a template. In one aspect, blocker 716 is completely or partially degradable. For example, blocker 716 comprises one or more dUs instead of dTs, and is degradable by UDG or the USER enzyme mix. Also provided is a third polypeptide-polynucleotide conjugate 724, which comprises an antibody 726 specific for the Fc portion of the antibody analyte. In certain aspects, the antibody in the third polypeptide-polynucleotide conjugate is specific for the Fc of an antibody isotype, for example, IgG1, IgG2, IgM, IgD, IgE, IgA, or Ig Y. The third polypeptide-polynucleotide conjugate further comprises a polynucleotide portion comprising a 3' blocker 728 that blocks primer extension, an isotype extension sequence 730 that shares sequence homology with the isotype extension sequence 722, an isotype coding sequence 732, and a primer sequence 734. In some embodiments, isotype extension sequence 730 is identical to isotype extension sequence 722, or isotype extension sequence 730 is hybridizable to a sequence complementary to isotype extension sequence 722. FIG. 7 shows the third polypeptide-polynucleotide conjugate bound to the Fc portion of the antibody. However, it is to be understood that in certain aspects, the third conjugate is provided after the first and second conjugates and the antibody form a ternary complex, while in other aspects, the third conjugate is provided substantially concurrently with first conjugate, second conjugate, and/or the antibody analyte. For example, the third conjugate can form a complex with the antibody analyte, and the pre-formed complex is then contacted with the firs conjugate or a transient conjugate complex formed by the first and second conjugates.

In step 736, the polynucleotide portion of the first polypeptide-polynucleotide conjugate undergoes primer extension using the polynucleotide portion of the second polypeptide-polynucleotide conjugate as a template. The first polynucleotide portion is extended to contain an idiotype extension/coding sequence 738 complementary to sequence 720, and an isotype extension sequence 740 complementary to sequence 722. Thus, the extended first polynucleotide portion incorporates the information from the second polypeptide-polynucleotide conjugate. In one aspect, idiotype extension/coding sequence 720 is an identifying sequence that identifies polypeptide portion 708 of the second polypeptide-polynucleotide conjugate. In one aspect, isotype extension sequence 722 shares sequence homology with isotype extension sequence 730 of the third polypeptide-polynucleotide conjugate, therefore isotype extension sequence 740 of the second polypeptide-polynucleotide conjugate is hybridizable to sequence 730 the third polypeptide-polynucleotide conjugate.

In step 742, the second polynucleotide portion and the extended first polynucleotide portion are dissociated from each other. In one aspect, due to sequence complementarity between sequences 730 and 740, the third polynucleotide portion and the extended first polynucleotide portion are engaged and the engaged sequences are subjected to primer extension. In this example, because the third polynucleotide portion is blocked at the 3' end (by blocker 728), only the extended first polynucleotide portion is further extended. In one aspect, blocker 728 is completely or partially degradable. For example, blocker 728 comprises one or more dUs instead of dTs, and is degradable by UDG or the USER enzyme mix.

In step 744, a further extended first polynucleotide portion is generated, comprising an isotype coding sequence 746 complementary to sequence 732, and a primer sequence 748 complementary to sequence 734. Thus, the further extended first polynucleotide portion incorporates information from the third polypeptide-polynucleotide conjugate. For example, isotype coding sequence 732 can be an identifying sequence that identifies antibody 726 of the third polypeptide-polynucleotide conjugate. Therefore, in one aspect, the further extended first polynucleotide portion incorporates information from all three polypeptide-polynucleotide conjugates. For example, the further extended first polynucleotide portion comprises sequence 712 that identifies the first polypeptide portion 702, idiotype extension/coding sequence 738 that identifies the second polypeptide portion 708, and isotype coding sequence 746 that identifies antibody 726 specific for the Fc portion of the antibody analyte. Accordingly, in one aspect, detection of the further extended first polynucleotide portion depends on co-localization of two antigen-binding regions and the Fc portion of the antibody analyte. In one embodiment, the extension-dependent re-extension of a polypeptide-polynucleotide conjugate further increases the specificity of an assay disclosed herein.

In certain embodiments, a fourth polypeptide-polynucleotide conjugate can be used, and the fourth conjugate specifically binds to the antibody analyte in a region other than the regions that specifically bind to the first, second, and third polypeptide-polynucleotide conjugates. In one aspect, a primer extension product incorporates information from all four polypeptide-polynucleotide conjugates, for example, sequence information that identifies the first, second, third, and fourth polypeptide portions of the conjugates and therefore identifies the regions on the antibody that the conjugates specifically bind. In other embodiments, even more polypeptide-polynucleotide conjugates, for example, a fifth, sixth, or seventh conjugate, can be used in the present method.

In one embodiment, for example, as shown in step 750 of FIG. 7, primer sequences 710 and 748 (or complements thereof) can be used to amplify and/or sequence the further extended first polynucleotide portion as shown in FIG. 7. In one aspect, detection of all or a portion of sequence of the further extended first polynucleotide portion indicates co-localization of all three conjugates, and is therefore a specific signal that depends on specific binding of all three conjugates to the same analyte antibody molecule. In another aspect, detection of all or a portion of sequence of the further extended first polynucleotide portion indicates the absence, presence, and/or amount of the antibody analyte in a sample, for example a biological sample such as serum, plasma, urine or another body fluids.

In one embodiment, for example in step 742 of FIG. 7, the second polynucleotide portion dissociates from the extended first polynucleotide portion in order for the third polynucleotide portion and the extended first polynucleotide portion to be engaged. Dissociation can be achieved in a number of ways, for example, by heating, degradation and/or removal of the second polypeptide-polynucleotide conjugate, degradation and/or removal of the second polynucleotide portion, or use of polynucleotide portions with differential affinities, or any combination thereof. For example, the second polynucleotide portion can be engineered to be preferentially cleaved or degraded, e.g., a RNA second polynucleotide portion is more readily cleaved or degraded than a DNA or peptide nucleic acid (PNA) first or third polynucleotide portion. In another example, the first, second, and third polynucleotide portions each comprises DNA, RNA, PNA, and/or locked nucleic acid (LNA). For instance, the first and second polynucleotide portions are made of LNA and DNA, respectively, and become hybridized to extend the first polynucleotide portion before adding the third conjugate. Complementary LNA and PNA hexamers bind to each other with significantly higher affinity than each binds to DNA, and with far greater affinity than DNA binds to complementary DNA. In addition, the hybridization of an LNA oligomer to a PNA oligomer is unaffected by the ionic strength of the buffer, making the LNA/PNA pair an attractive candidate as a replacement for DNA in programmable assembly. See, Ng and Bergstrom, 2005, "Alternative nucleic acid analogues for programmable assembly: hybridization of LNA to PNA," Nano Lett. 5(1):107-11, the disclosure of which is incorporated by reference in its entirety for all purposes. A third polynucleotide portion made of PNA binds to the LNA first polynucleotide portion with significantly higher affinity than the DNA second polynucleotide portion, and thus displaces the second polynucleotide portion from the first polynucleotide portion. Polynucleotides with differential affinities can be used in conjunction with heating and/or altering ionic strength of the buffer to promote dissociation of the first and second polynucleotide portions and/or association of the first and third polynucleotide portions.

6. Use

In one aspect, a method disclosed herein takes advantage of the bivalent or multivalent nature of an analyte. For example, an antibody can be bivalent in that it possesses two antigen-binding regions, each for specific binding of a peptide epitope. The antibody can also be bifunctional, for example, as in the case of bispecific antibodies. In one embodiment, a library of polypeptide-DNA conjugates is first anchored to a solid support at a loading density low enough to result in one polypeptide binding event per antibody. Second, target antibodies are captured by the anchored polypeptide-DNA conjugates from a biological sample. Third, a second library of polypeptide-DNA conjugates is added and allowed to bind to the second antigen-binding regions on the antibodies bound to the anchored polypeptide-DNA conjugates. Next, the DNA portions of the conjugates bound to the same antibody analyte are combined and sequenced to identify the interacting molecules, e.g., the antibody and the peptide epitopes in the conjugates and. An anomalous DNA portion combinations resulting from non-specific binding are easily identified, permitting highly specific and sensitive antibody assays. In one aspect, the peptide epitopes used herein are more powerful than full length proteins for differentiating closely related antigens. In one aspect, the present method is used for resolving pathogen strains and individual protein variations that affect disease treatment and outcomes. In one aspect, the use of polypeptide-DNA libraries enables high multiplexing and the ability to quickly design and test assays based only on sequence information. A method disclosed herein therefore has the potential to positively impact many areas of basic research and clinical diagnostics. For example, methods disclosed herein are useful for the detection of antibodies to *Borrelia*, the Lyme disease pathogen.

In certain aspects, disclosed herein are methods for detecting antibodies in clinical samples. These assays are especially important when PCR-based techniques cannot be used. For example, a method of the present disclosure is used to detect an immune reaction to pathogens present at low abundance (e.g., Lyme disease, tuberculosis, Kaposi's sarcoma), to detect autoimmune antibodies, to detect antibodies to tumor associated antigens.

In other aspects, the present disclosure provides capabilities for specific and multiplexed detection of antibodies. In yet other aspects, the present compositions, systems, and methods are used in disease proteomics and personalized medicine, for example, for simultaneous detection of many antibodies. This represents significant advances because it is increasingly appreciated that patients and their pathologies are heterogeneous. Thus, single biomarker measurements often do not achieve meaningful predictive power. Such power can, however, be provided when multiple biomarkers are analyzed together. In addition, conducting multiple measurements without multiplexing is likely to be prohibitively laborious and/or require unacceptably large quantities of sample. As a result, the presently disclosed multiplexed antibody detection represents significant advances in early and improved disease diagnostics.

In one embodiment, provide herein are highly multiplexed, specific antibody detection methods. In one aspect, the present methods combine binding assays with next-generation sequencing techniques. In another aspect, the use of peptides as antigens allows development of reagents directly from sequence information without the need to clone or purify individual protein antigens and allows removal of areas on the protein antigens that contribute to nonspecific signal. For example, specific detection of Lyme disease biomarkers in human serum is disclosed.

The provided methods generally are carried out using samples, typically biological samples and samples derived therefrom, containing an analyte or a collection of analytes of interest. In some embodiments, the sample is obtained or derived from a subject having or suspected of having a particular disease or condition of interest. In some examples, the sample is or is derived from a bodily fluid, such as blood (e.g., whole blood or fraction thereof, such as plasma or serum), e.g., maternal blood, saliva, urine, spinal fluid, synovial fluid, amniotic fluid, lachrymal fluid, ichor, lymphatic fluid, or cerebrospinal fluid. In certain aspects, the sample is a liquid sample. In some aspects, the sample is extracellular fluid. In some aspects, the sample is an extracellular sample, for example, a sample that contains or is derived from an extracellular fluid, such as plasma. In some aspects, the sample contains a pathogen-induced or pathogen-reactive analyte, e.g., an analyte reactive to a viral or bacterial molecule. In other embodiment, an analyte in induced in a host by a pathogen component. In some aspects, the sample contains other molecules of similar physical or chemical properties in addition to the analyte of interest. For example, a serum sample from a patient with viral infection contains many serum proteins including antibodies in addition to antibodies against viral components. Samples for use with the provided methods include those that are derived from such biological samples, such as those prepared as a result of protein purification or enrichment from such a biological sample.

In one aspect, Lyme samples with corresponding clinical history are utilized, and the assay results for each sample are correlated with the corresponding clinical history of the sample. In another aspect, test samples include those from patients initially tested negative for Lyme, but later diagnosed with Lyme disease based on clinical symptoms. In yet another aspect, samples from post-Lyme disease syndrome (PLDS) patients are tested. In some embodiments, the present compositions, systems, and methods are used for early Lyme disease detection and/or for detection of PLDS.

Lyme disease or Lyme borreliosis is caused by a number of *Borrelia* species including *Borrelia burgdorferi, Borrelia afzelii*, and *Borrelia garinii* that are transmitted by ticks. It is the most commonly reported vector-borne infection in the US with over 250,000 cases between 2002 and 2011 (cdc.gov/lyme/). The disease has a long list of symptoms (cdc.gov/lyme/signs_symptoms/index.html). Additionally, ~10-20% of Lyme disease patients will have PLDS with lingering symptoms of fatigue, pain, or joint and muscle aches.

In some embodiments, the present methods detect host response antibodies to *Borrelia,* including but not limited to antibodies for the following antigens: VlsE protein, polyprotein VlsE-OspC-VlsE-OspC, a 26-mer C6 peptide from VlsE, and a combination of VlsE protein and pepC10 peptide. In certain embodiments, the present systems and methods are sensitive to a Lyme disease-associated antibody during early stages of infection, for example, the first few weeks after infection, due to the ability to detect low levels of antibodies. In certain embodiments, early detection of *Borrelia* during the first few weeks of infection reduces or eliminates the need for follow-up testing, results in increased efficiency of treatment with antibiotics, improves specificity of detection and treatment, and/or reduces misdiagnosis that leads to unnecessary treatment with toxic drugs. In other aspects, the present methods differentiate between *Borrelia* species or strains that cause a particular infection. For example, peptides from various *Borrelia* species and strains can be used to characterize the infection. In other examples, a method of the present disclosure is easily optimized for a pathogen, for example, *Borrelia,* due to the ability to screen many peptide epitopes and to detect multiple antibodies. For instance, the present methods are used for selection of antigens that are specific for a particular infection and do not cross-react with antibodies resulting from other infections. In yet other aspects, the present methods distinguish PLDS patients from fully recovered patients. In one embodiment, a method of the present disclosure is used to determine the stage of active or antecedent infection in Lyme borreliosis and PLDS patients, and this information is used to guide therapies.

In one aspect, libraries of polypeptide-DNA conjugates are generated for analysis of a sample containing antibodies of interest or suspected of containing the antibodies. For example, a library of polypeptide-DNA conjugates comprising 9-mer, 10-mer, 11-mer, 12-mer, 13-mer, 14-mer, 15-mer, 16-mer, 17-mer, 18-mer, 19-mer, 20-mer, 21-mer, 22-mer, 23-mer, 24-mer, 25-mer, 26-mer, 27-mer, 28-mer, 29-mer, or 30-mer peptide epitopes can be produced and used in a method disclosed herein. The peptide epitopes can be derived, for instance, from the Immune Epitope DataBase (www.iedb.org). The polypeptide-DNA conjugate libraries can cover about 10, about 50, about 100, about 150, about 200, about 250, about 300, about 350, about 400, about 450, about 500, about 550, or about 600 organisms or species. In one aspect, the polypeptide-DNA conjugate libraries comprise control peptide epitopes, for example, those derived from peptide tags HA, FLAG, and c-Myc. In another aspect, the polypeptide-DNA conjugate libraries comprise peptide epitopes derived from pathogen- or disease-associated proteins, for example, VlsE (e.g., from *Borrelia burgdorferi*), OspA, OspC, BmpA, DbPA, DbPB, p83/p100, p88, p66, Flagellar filament, and other *Borrelia* proteins. In yet another aspect, the polypeptide-DNA conjugate libraries comprise peptide epitopes derived from protein variants of pathogen- or disease-associated proteins, for example, protein variants from three major species of *Borrelia* (*B. burgdorferi, B. garinii* and *B. afzelii*) known to cause Lyme disease. The species of pathogenic *Borrelia* show different symptoms and tick vector specificity. Even within regions where only one of *Borrelia* species is found, Lyme disease progresses very differently from one patient to another. Thus, due to the capacity to multiplex, the presently disclosed methods are well suited to screen disease-associated or pathogen-derived epitopes in order to study their correlation with disease etiology, progression, and prognosis.

Next-generation sequencing platforms, such as MiSeq (Illumina Inc., San Diego, Calif.), can be used for highly multiplexed assay readout. A variety of statistical tools, such as the Proportion test, multiple comparison corrections based on False Discovery Rates (see Benjamini and Hochberg, 1995, Journal of the Royal Statistical Society Series B (Methodological) 57, 289-300), and Bonferroni corrections for multiple testing, can be used to analyze assay results. In addition, approaches developed for the analysis of differential expression from RNA-Seq data can be used to reduce variance for each analyte and increase overall power in the analysis. See Smyth, 2004, Stat. Appl. Genet. Mol. Biol. 3, Article 3.

Polypeptide-polynucleotide conjugates, conjugate pairs, conjugate sets and/or libraries comprising a proteome are well within the scope of the present disclosure, and can be manufactured at low cost. For example, a library of polypeptide-polynucleotide conjugates comprising peptide epitopes representing an individual human's proteome (or various subsets of the individual's proteome) can be constructed and used to screen for the absence, presence, and/or amount of antibodies in sera. In one aspect, a polypeptide-polynucleotide conjugate set comprising an individual's proteome or one or more reference proteomes is used to screen for antibodies associated with a condition or a disease, for example, cancers, autoimmune diseases, or infections.

The proteome can be of any organism, e.g., a prion, a virus, a bacteria, a fungus, a microorganism, a vector (e.g., a tick, a fly, or a mosquito), and a mammal. Thus, the present methods can be used to detect a number of infectious diseases or infection states in a subject. Pathogenic viruses include, but are not limited to, Retroviridae (e.g., human immunodeficiency viruses, such as HIV-1 (also referred to as HTLV-III, LAV or HTLV-III/LAV, or HIV-III); and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Bimaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxyiridae (variola viruses, vaccinia viruses, pox viruses); and Iridoviridae (e.g., African swine fever virus); Hepatitis C virus; and unclassified viruses (e.g., the agent of delta hepatitis (thought to be a defective satellite of hepatitis B virus); Norwalk and related viruses, and astroviruses).

Pathogenic bacteria include, but are not limited to, *Helicobacter pyloris, Borelia burgdorferi, Legionella pneumophila, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum*, pathogenic strains of *Escherichia coli, Streptobacillus moniliformis, Treponema pallidium, Treponema pertenue, Leptospira*, and *Actinomyces israelli*.

Infectious fungi include, but are not limited to, *Cryptococcus neoformans, Histoplasma capsulatum, Coccidioides immitis, Blastomyces dermatitidis, Chlamydia trachomatis, Candida albicans*.

Infectious protozoa include, but are not limited to, *Plasmodium* spp., e.g., *Plasmodium falciparum;* Trypanosomes, e.g., *Trypanosoma cruzi;* and *Toxoplasma gondii*.

Allergens include, but are not limited to, pollens, insect venoms, animal dander dust, fungal spores and drugs (e.g. penicillin). Examples of natural, animal and plant allergens include proteins specific to the following genera: Canine (*Canis familiaris*); *Dermatophagoides* (e.g. *Dermatophagoides farinae*); *Felis* (*Felis domesticus*); *Ambrosia* (*Ambrosia artemiisfolia;* Lolium (e.g. *Lolium perenne* or *Lolium multiflorum*); *Cryptomeria* (*Cryptomeria japonica*); *Alternaria* (*Alternaria alternata*); Alder; *Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Charnaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*). Use of epitopes from the above allergens in the present methods for antibody detection and analysis is also envisaged.

Any of a variety of known tumor-associated antigens (TAA) can be used to derive epitopes for detecting tumor-associated antibodies according to the present disclosure. Tumor-associated antigens (or epitope-containing fragments thereof) include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV 18, TUAN, alpha-feto protein (AFP), OFP, CA-125, CA-50, CA-19-9, renal tumor-associated antigen G250, EGP-40 (also known as EpCAM), S100 (malignant melanoma-associated antigen), p53, prostate tumor-associated antigens (e.g., PSA and PSMA), and p21ras.

Antibodies associated with autoimmunity or autoimmune diseases, e.g., autoantibodies, can be detected according to the present disclosure. Exemplary autoantibodies include and are not limited to: antinuclear antibodies, anti-SSA/Ro autoantibodies, anti-La/SS-B autoantibodies, anti-centromere antibodies, anti-neuronal nuclear antibody-2, anti-dsDNA, anti-Jo1, anti-RNP, anti-Smith, anti-topoisomerase antibodies, anti-histone antibodies, anti-p62 antibodies, anti-sp100 antibodies, anti-glycoprotein-210 antibodies, anti-transglutaminase antibodies, anti-tTG, anti-eTG, anti-ganglioside antibodies, anti-actin antibodies, anti-CCP, liver kidney microsomal type 1 antibody, Lupus anticoagulant, anti-thrombin antibodies, anti-neutrophil cytoplasmic antibody (ANCA), c-ANCA, p-ANCA, Rheumatoid factor, antismooth muscle antibody, anti-mitochondrial antibody, anti-SRP, anti-VGCC, and anti-VGKC.

Other antigens of interest include, but are not limited to, sperm-associated antigens, venoms, hormones, and the like. Sperm-associated proteins are known in the art, and a nucleic acid molecule encoding any such protein is suitable for use herein. See, e.g., Primakoff (1994) *Reproductive Immunol.* 31:208-210; Naz et al. (1995) *Human Reprod. Update* 1:1-18; Kerr et al. (1998) *J. Reprod. Immunol.* 40:103-118; and U.S. Pat. No. 6,197,940. Hormones of interest include, but are not limited to, human chorionic gonadotrophin (hCG). Hormones such as hCG are useful to elicit specific antibodies, for use as contraceptive. Venoms of interest include those from any poisonous animal, e.g., snake venoms, including, but not limited to, α-neurotoxins, kappa toxins, β-neurotoxins, dendrotoxins, cardiotoxins, myotoxins, and hemorrhaging. Of particular interest in many embodiments are modified venoms that elicit specific antibodies, but are not themselves toxic. Such modified venoms are useful to elicit an immune response to a venom, and in many embodiments, elicit a protective immune response such that, upon subsequent exposure to the venom from an animal source, any adverse physiological effects of the venom are mitigated. Any of these antigens can be used to derive epitopes for detecting antibodies according to the present disclosure.

The following examples are intended to further describe and illustrate various aspects of the present disclosure, but not to limit, the scope of the present disclosure in any manner, shape, or form, either explicitly or implicitly.

EXAMPLE 1

Detection of Anti-HA Antibodies with HA Probes

In this example, a capture probe and a detection probe pair was used to detect anti-human influenza virus hemagglutinin antibodies (anti-HA antibodies).

The capture probe and detection probe pair was produced by conjugation of chemically synthesized peptide and oligonucleotide using established techniques, purified and characterized. They can also be produced by in vitro transcription and translation methods. See, for example, Kozlov et al., 2012, PLoS One 7, e37441. Both the capture probe and detection probe are polypeptide-polynucleotide conjugates, and both contain the HA affinity tag (SEQ ID NO: 1, YPYDVPDYA, amino acids 99 to 107 of the human influenza virus hemagglutinin). See, Wilson et al., 1984, Cell 37, 767-778. The HA affinity tag serves as the epitope for the anti-HA antibodies that were detected in this example. This assay format is termed the DBA format. FIG. 4 provides a schematic showing the DBA format according to one embodiment of the present disclosure.

Figure 8:
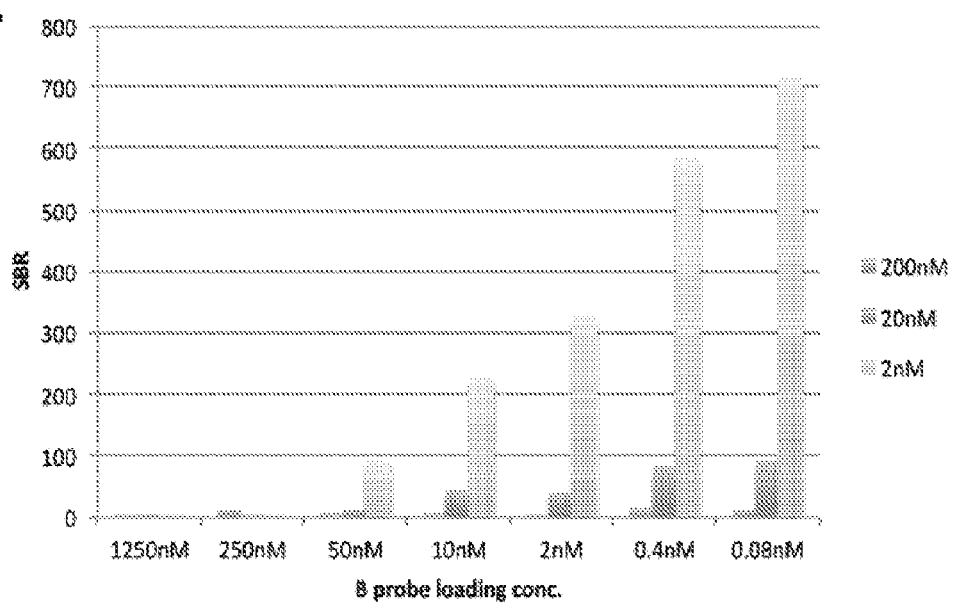
FIG. 8A shows the relationship between the signal-to-background ratios (SBR) and conjugate concentrations of DBA assays according to some embodiments of the present disclosure.
FIG. 8B shows the relationship between the 40-Ct values and conjugate concentrations of DBA assays according to some embodiments of the present disclosure. Ct is the qPCR characteristics representing cycle threshold, and is the number of cycles it takes for the signal to raise above a threshold in qPCR (qPCR background). 40 cycles is the maximum detectable Ct in the system used. The 40-Ct values are reference-independent and are used to show both signal and background changes.
Figure 8:
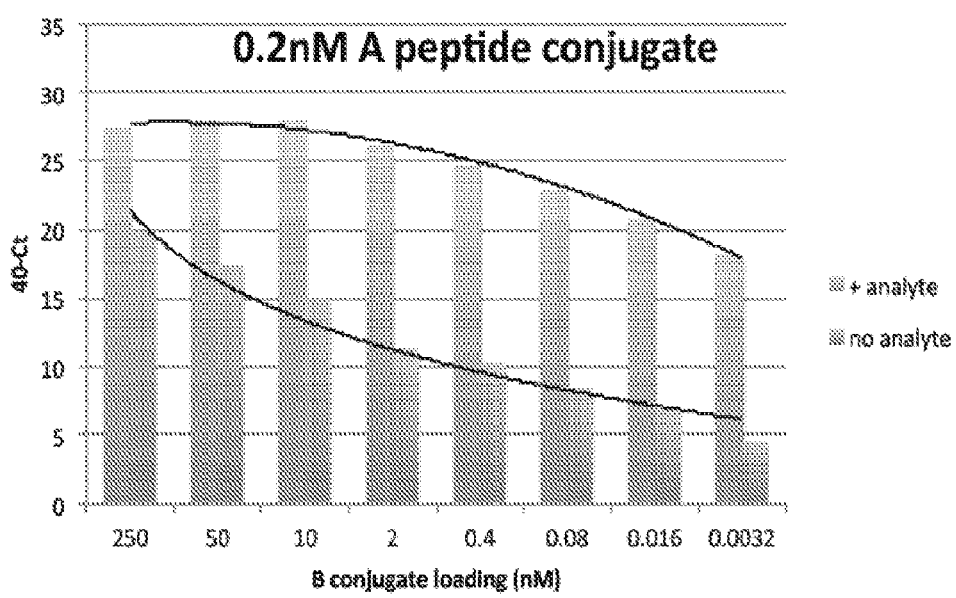

The capture probe and detection probe pair was first used to detect a rabbit anti-HA polyclonal antibody at a concentration of 6 nM. Control samples included an anti-FLAG antibody (6 nM), and a blank vehicle control containing no antibodies. As shown in FIG. 8A, a fixed quantity of streptavidin beads (1 µl, 1% solution) was loaded with 1 µl of different concentrations of the capture probe (B). 10 µl of different concentrations of the detection probe (A) were then used upon capture of the analyte, the rabbit anti-HA polyclonal antibody. When the capture probe (B) and the detection probe (A) are co-localized due to specific binding to an anti-HA antibody, polymerase extension produces a joint product of A and B that can be detected. In this example, detection and quantitation of the relative yield of product was by qPCR.

A matrix of 7 concentrations of the capture probe B (0.08 nM, 0.4 nM, 2 nM, 10 nM, 50 nM, 250 nM, and 1250 nM) versus 3 different concentrations of the detection probe A (2 nM, 20 nM, and 200 nM) was tested. Data were collected for the rabbit anti-HA polyclonal antibody (6 nM) and the control anti-FLAG antibody (6 nM). The signal-to-background ratio (SBR) was calculated as 2^(Ct[no antibody control]−Ct[antibody sample]). Relationship between the SBR and the concentrations of the capture probe and the detection probe is shown in FIG. 8A.

In another experiment, a matrix of 8 concentrations of the capture probe (0.0032 nM, 0.016 nM, 0.08 nM, 0.4 nM, 2 nM, 10 nM, 50 nM, and 250 nM) versus 3 different concentrations of the detection probe A (0.02 nM, 0.2 nM, and 2 nM) was tested. For example, as shown in FIG. 8B, the concentration of the detection probe A was kept at 0.2 nM, and lower concentrations of the capture probe B were used than those shown in FIG. 8B. In addition, a mouse monoclonal antibody was used instead of the rabbit polyclonal antibody in FIG. 8A. Results for the detection probe A at the 0.02 nM and 2 nM concentrations are not shown, and demonstrated a similar pattern to that shown in FIG. 8B for the detection probe A concentration kept at 0.02 nM. Data were collected for the mouse anti-HA monoclonal antibody (6 nM) and the control mouse anti-FLAG antibody (6 nM). Relationship between the 40-Ct value and the concentrations of the capture probe, with or without the mouse anti-HA monoclonal antibody in the sample, is shown in FIG. 8B. These results indicate that the background ("no analyte") decreased more rapidly than the signal did, as the concentration of the capture probe decreased.

This example demonstrates that the DBA assay is capable of detecting anti-HA antibody. The signal for anti-FLAG antibody was within 2-fold of the no antibody control. The signal of anti-HA antibody was up to ~30,000 fold over the background, demonstrating high specificity. In this example, signal, background and SBR were depended on the probe concentrations or the surface densities of the probes. For example, high probe concentrations resulted in lower SBR, as a result of higher background. In this example, as probe concentration was increased, the background signal grew at a faster rate than analyte-specific signal.

This example demonstrates that concentrations of the probes and/or the densities of the probes on a substrate, e.g., on the surface of beads, can be manipulated to achieve optimal signal to background ratio.

EXAMPLE 2

Detection of Anti-HA Antibodies with an HA Probe and a Secondary Antibody

Figure 9:
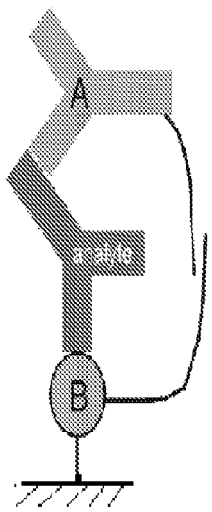
FIG. 9A is a schematic showing a complex formed between a polypeptide-polynucleotide conjugate pair and an antibody analyte according to one embodiment of the BSC assay format of the present disclosure.
FIG. 9B shows the relationship between the 40-Ct values and conjugate concentrations of BSC assays according to some embodiments of the present disclosure.
FIG. 9C shows a comparison between the DBA and BSC assays, and relationships between the 40-Ct values and conjugate concentrations for each assay format, according to some embodiments of the present disclosure.
Figure 9:
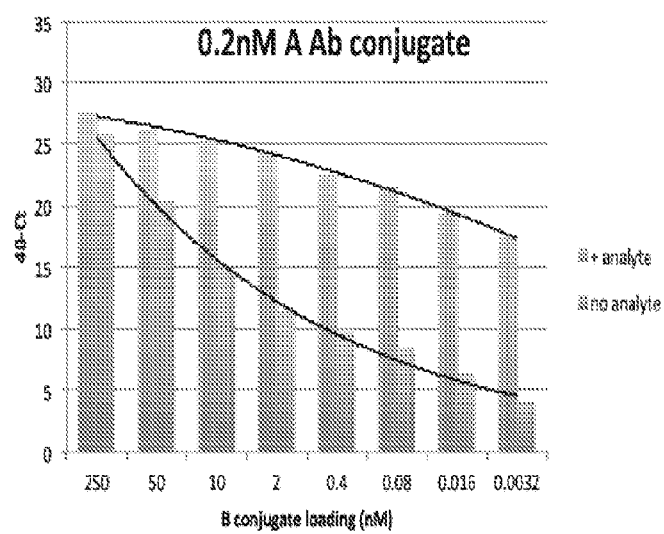
Figure 9:
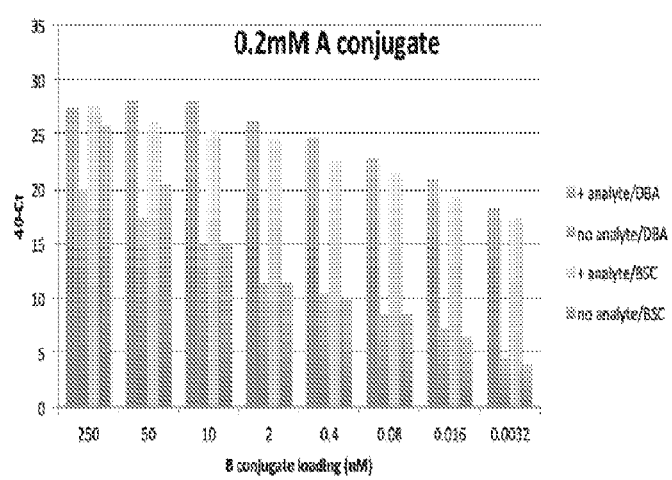

In this example, a capture probe and a detection probe pair was used to detect an anti-human influenza virus hemagglutinin antibody (anti-HA antibody). The capture probe is a polypeptide-polynucleotide conjugate, and contains the HA affinity tag (SEQ ID NO: 1, YPYDVPDYA, amino acids 99 to 107 of the human influenza virus hemagglutinin) as described in Example 1. The HA affinity tag serves as the epitope for an anti-HA mouse monoclonal antibody that was detected in this example. The detection probe is a polypeptide-polynucleotide conjugate containing an anti-mouse antibody. This assay format is termed the BSC format. A schematic of a complex formed between the capture probe (B), the antibody analyte, and the detection probe (A) according to one embodiment of the BSC format is shown in FIG. 9A. Note that the detection probe A in FIG. 9A is a polypeptide-polynucleotide conjugate, and the polypeptide portion is an antibody that binds to a constant region of the antibody analyte, while the capture probe B is a polypeptide-polynucleotide conjugate in which the polypeptide portion specifically binds to an antigen-binding region of the antibody analyte.

The capture probe and detection probe pair was used to detect an anti-HA mouse monoclonal antibody at a concentration of 6 nM. Control samples included an anti-FLAG mouse antibody (6 nM), and a blank vehicle control containing no antibodies. As shown in FIG. 9B, a fixed quantity of streptavidin beads (1 µl, 1% solution) was loaded with 1 µl of different concentrations of the capture probe (B). 10 µl of different concentrations of the detection probe (A) were then used upon capture of the analyte, anti-HA mouse monoclonal antibody. When the capture probe (B) and the detection probe (A) are co-localized due to binding to an anti-HA antibody (e.g., the anti-HA mouse monoclonal antibody in this example), polymerase extension produces a joint product of A and B that can be detected. In this example, detection and quantitation of the relative yield of product was by qPCR.

A matrix of 8 concentrations of the capture probe B (0.0032 nM, 0.016 nM, 0.08 nM, 0.4 nM, 2 nM, 10 nM, 50 nM, and 250 nM) versus 3 different concentrations of the detection probe A (2 nM, 0.2 nM, and 0.02 nM) was tested. For example, as shown in FIG. 9B, the concentration of the detection probe A was kept at 0.2 nM. Results for the detection probe A at the 0.02 nM and 2 nM concentrations are not shown, and demonstrated a similar pattern to that shown in FIG. 9B for the detection probe A concentration kept at 0.02 nM. Data were collected for the mouse anti-HA monoclonal antibody (6 nM) and the control anti-FLAG antibody (6 nM). Relationship between the 40-Ct value and the concentrations of the capture probe, with or without the mouse anti-HA monoclonal antibody in the sample, is shown in FIG. 9B. These results indicate that the background ("no analyte") decreased more rapidly than the signal did, as the concentration of the capture probe decreased.

Data from FIG. 8B and FIG. 9B were plotted side-by-side and shown in FIG. 9C. In the DBA format, both the capture probe B and the detection probe A were polypeptide-DNA conjugates containing the HA affinity tag (the epitope for anti-HA antibodies in the sample). In the BSC format, the capture probe B was a polypeptide-DNA conjugate containing the HA affinity tag, while the detection probe A was a secondary antibody-DNA conjugate.

The example shows that an anti-HA antibody can be detected using the BSC assay format. The signal for anti-FLAG antibody was within 2-fold of the no antibody control. The signal of anti-HA antibody was up to ~8,000 fold over the background, demonstrating high specificity. In this example, signal, background, and signal to background ratio (SBR) were depended on the probe concentrations or the surface densities of the probes. For example, high probe concentrations resulted in lower SBR, as a result of higher background. In this example, as probe concentration was increased, the background signal grew at a faster rate than analyte-specific signal. This example demonstrates that concentrations of the probes and/or the densities of the probes on a substrate, e.g., on the surface of beads, can be manipulated to achieve optimal signal to background ratio.

As shown in FIG. 9C, the background grew faster in the BSC assay format than in the DBA format, as the concentration of the capture probe B increased. In one aspect, the secondary antibody in the detection probe used in the BSC format may exhibit more non-specific binding than the HA affinity tag in the detection probe used in the DBA format.

EXAMPLE 3

Titration of Anti-HA Antibodies Detected by HA Probes

In this example, a capture probe and a detection probe pair was used to detect anti-human influenza virus hemagglutinin antibodies (anti-HA antibodies). Both of the capture probe and detection probe were polypeptide-polynucleotide conjugates containing the HA affinity tag as described in Example 1.

Figure 10:
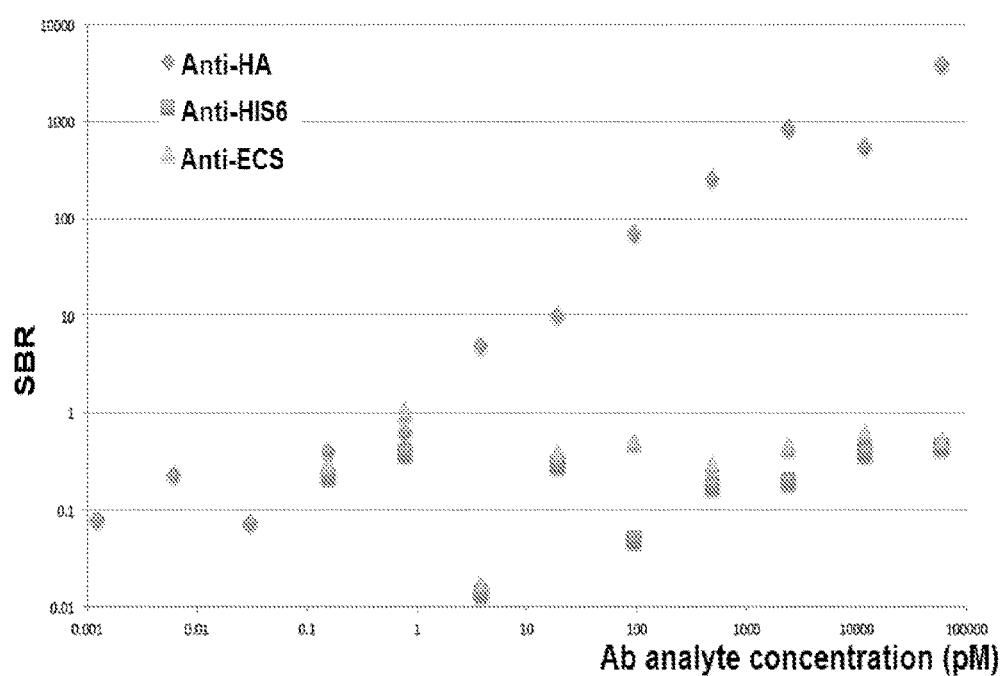
FIG. 10 shows the relationship between the signal-to-background ratios (SBR) and analyte concentrations of DBA assays according to some embodiments of the present disclosure.

The capture probe and detection probe pair was used to detect a rabbit anti-HA polyclonal antibody in a series of samples containing 60 nM-1 fM of the antibody. Control samples included an anti-ECS antibody, an anti-HIS antibody, and a blank vehicle control containing no antibodies. A fixed amount of streptavidin beads (1 µl, 1% solution) was loaded with 1 µl of 0.4 nM capture probe (B), and 10 µl of 0.2 nM detection probe (A) was added upon capture of the rabbit anti-HA polyclonal antibody by the capture probe B. When the capture probe B and the detection probe A are co-localized due to specific binding to an anti-HA antibody, polymerase extension produces a joint product of A and B that can be detected. In this example, detection and quantitation of the relative yield of product was done by qPCR. The analyte concentration was plotted again the signal-to-background ratio, as shown in FIG. 10.

In this example, the limit of detection (LOD) for polyclonal rabbit anti-HA antibody was ≥1 pM. This example demonstrates that the DBA assay format is specific for detecting the anti-HA antibody, and does not detect even high concentrations of anti-ECS or anti-HIS antibodies.

EXAMPLE 4

Detection of Anti-HA Antibodies in Serum-containing Samples

This example describes using the DBA and BSC assay formats for detecting anti-HA antibodies in samples containing other antibodies and proteins, for example, samples containing serum.

Figure 11:
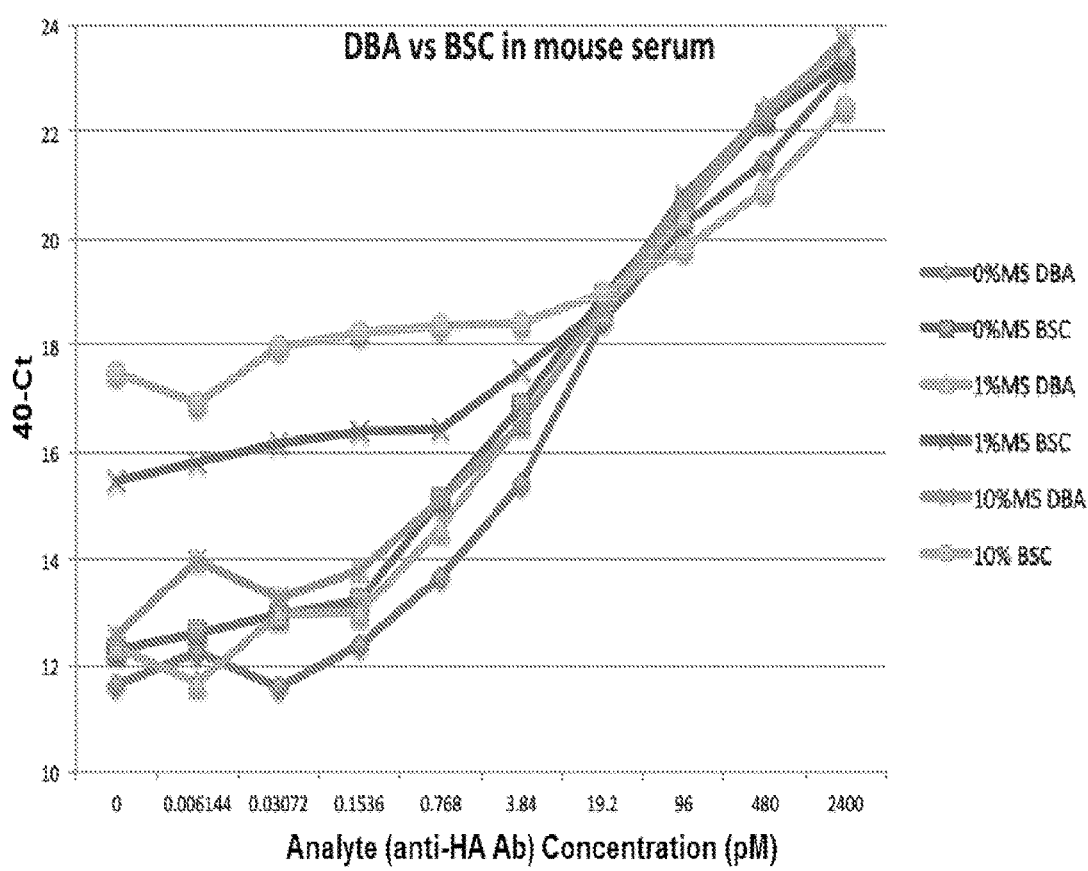
FIG. 11 shows a comparison between the DBA and BSC assays, and relationships between the 40-Ct values and analyte concentrations for each assay format, according to some embodiments of the present disclosure.

A fixed quantity of streptavidin beads (1 µl, 1% solution) was loaded with 1 µl of 0.4 nM capture probe (B). 10 µl of 0.2 nM detection probe (A) were added upon capture of the analyte, an anti-HA mouse monoclonal antibody. In the DBA format, both the capture probe B and the detection probe A were polypeptide-DNA conjugates containing the HA affinity tag (the epitope for anti-HA antibodies in the sample). In the BSC format, the capture probe B was a polypeptide-DNA conjugate containing the HA affinity tag, while the detection probe A was a secondary antibody-DNA conjugate in which the secondary antibody is an anti-mouse antibody. A series of samples containing 2.4 nM-6 fM of the monoclonal mouse anti-HA antibody, in the absence or in the presence of total mouse serum, were tested. The samples contained 0%, 1%, or 10% of the mouse serum, indicated by 0% MS, 1% MS, and 10% MS, respectively, in FIG. 11. A blank vehicle control containing no antibodies was used.

Detection and quantitation of the relative yield of products between the capture and detection probes was accomplished by qPCR.

This example demonstrated that in the absence of mouse serum, BSC and DBA assays showed comparable performance, and both assay formats showed LOD<1 pM. In the presence of mouse serum, background signal in the BSC format increased significantly while the increase of background in the DBA format was minimal. In the BSC format, the sample containing 10% mouse serum showed greater increase in background than the sample containing 1% mouse serum, when both are compared to the sample containing 0% mouse serum. In this example, the DBA assay format was less prone to increased background in the presence of serum than the BSC assay format, resulting in higher sensitivity of the DBA assay format. In one aspect, the secondary antibody in the detection probe used in the BSC format may exhibit more non-specific binding than the HA affinity tag in the detection probe used in the DBA format. For example, the secondary antibody can bind to other antibodies in the serum, while the HA affinity tag specifically binds to the monoclonal mouse anti-HA antibody and not to antibodies originated from the mouse serum.

EXAMPLE 5

Detection of Anti-C6 Antibodies in Human Serum

This example describes detection of anti-C6 antibodies in human serum.

The C6 peptide (MKKDDQIAAAIALRGMAKDGK-FAVK, SEQ ID NO: 2) is a conserved immunogenic region of VlsE protein of *Borrelia burgdorferi*. The C6 peptide can be used for Lyme borreliosis diagnosis. Depending on the stage of the disease, there can be a 50-80% correlation between disease and C6 peptide response.

Optimization of the concentrations of polypeptide-DNA conjugates based on the C6 peptide in the DBA assay format was carried using methods similar to those in Example 1. A set of anti-C6 antibody positive and negative human serum samples was used at a fixed concentration. The samples were tested for the presence of C6 binding antibodies by a commercial ELISA assay (Immunetics) first to determine whether they were C6 antibodies positive or negative. 0.02 nM of the detection probe A and 0.4 nM of the capture probe B were used in subsequent assays.

Figure 12:
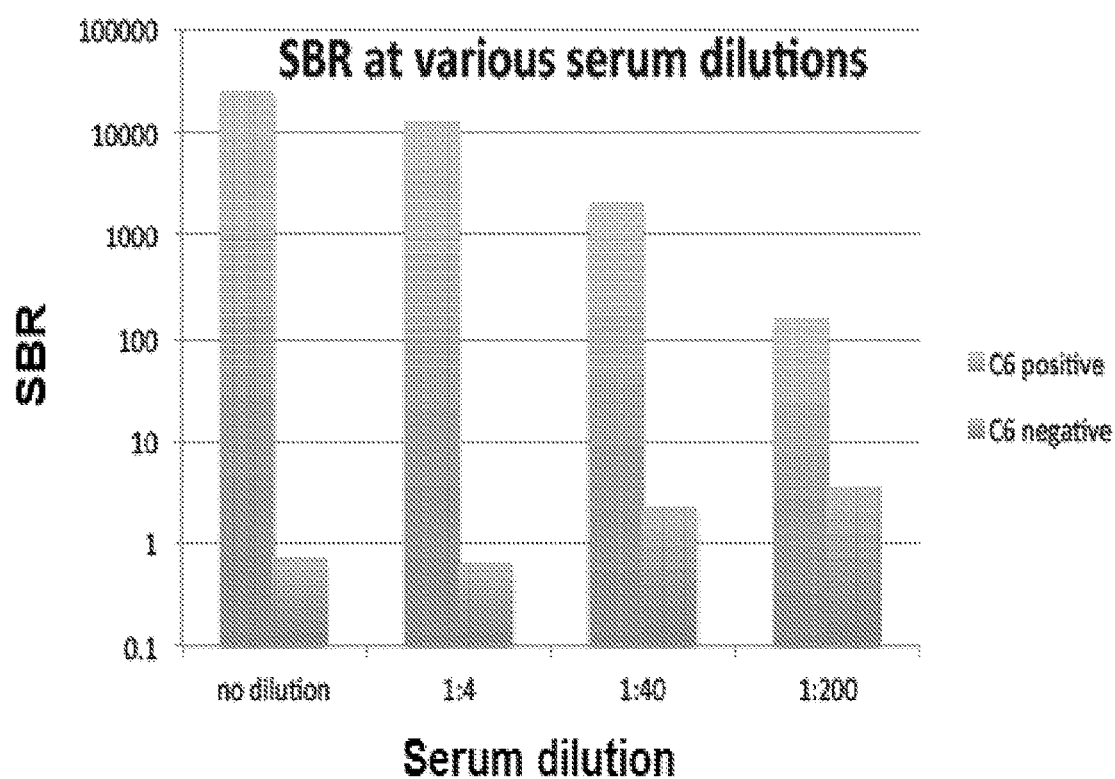
FIG. 12 shows the relationship between the signal-to-background ratios (SBR) and serum sample dilutions of DBA assays according to some embodiments of the present disclosure.

The anti-C6 antibody positive or negative human serum was diluted at a serum:buffer ratio of 1:4, 1:40, or 1:200. A serum sample without dilution was also used. This series of samples were used to determine the dependence of signal and background on the dilution ratio, as compared to no serum conditions. As shown in FIG. 12, the C6 antibody positive serum signal increased with increased proportion of the serum in the assay sample, and the C6 antibody negative serum signal was essentially identical (within measurement error) to a no-serum sample that was used to determine the inherent assay background. Even with the undiluted serum sample, the DBA assay was insensitive to the presence of nonspecific antibodies (antibodies that were not specific for the C6 peptide) in the sample.

This example indicates the DBA assay using a C6 peptide-based polypeptide-polynucleotide pair was specific for anti-C6 antibodies in human serum samples.

EXAMPLE 6

Comparison Between the DBA Assay Format and ELISA Assays

This example compares the DBA assay format and a commercially available ELISA assay for anti-C6 antibodies. The C6 peptide-based capture probe and detection probe pair is described in Example 5.

ELISA and similar immunoassays utilize a secondary antibody as a direct or indirect detector of an analyte. The secondary antibody can exhibit nonspecific binding and therefore lead to high background signal. In particularly, biological samples often contain many other proteins in addition to a target molecule, for example, an antibody to be detected. Human serum, for example, contains a rich variety of antibodies. Thus, the ELISA assay often exhibits dependency on sample dilution due to the nonspecific binding of the secondary antibody to antibodies other than the target antibody in the sample. As a result, dilution of serum samples is often necessary in an ELISA assay to limit the background. While sample dilution can result in improved signal-to-background ratio, it is often accompanied by a reduction in sensitivity due to analyte dilution.

Figure 13:
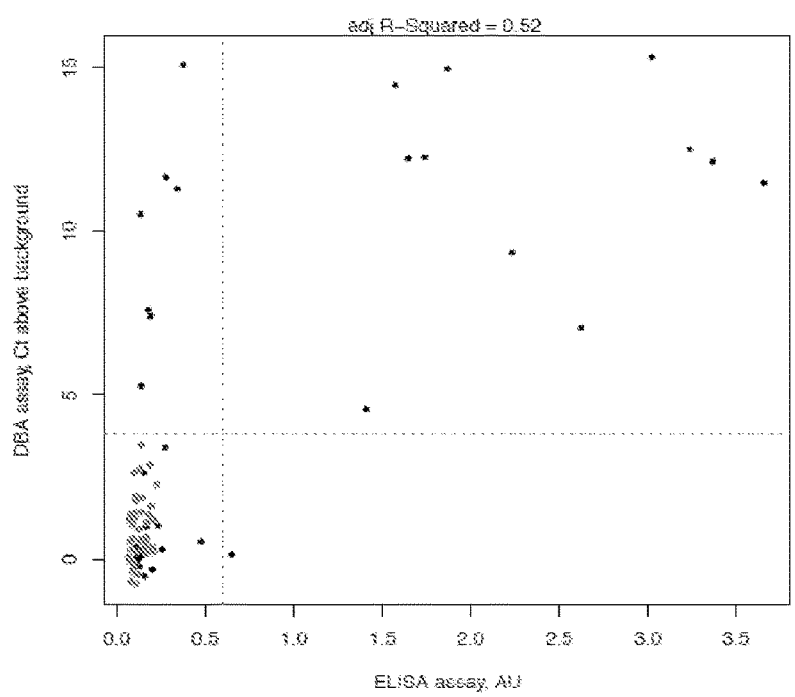
FIG. 13A shows a comparison between a commercially available ELISA assay and the DBA assay according to one embodiment of the present disclosure.
FIG. 13B shows the effects of sample dilution on the sensitivity of the ELISA and DBA assays.
Figure 13:
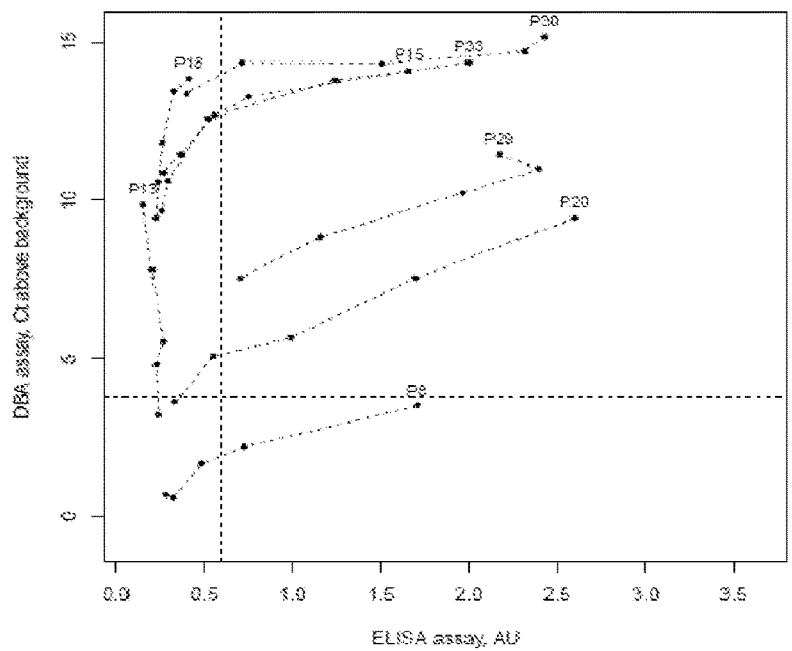

A set of 78 serum samples was tested side by side using the DBA assay format and a commercial C6 peptide ELISA (Immunetics). Of these 78 samples, 35 were classified as suspected Lyme disease positives on the basis of positive results of *Borrelia burgdorferi* whole cell lysate ELISA (performed by the sample provider). 43 samples were classified as controls. These controls were not tested in whole cell lysate ELISA, but given the low Lyme disease prevalence in US (0.007%), these control samples were likely to be Lyme disease negative. The control group was further classified as normal "healthy" controls (29 samples), 10 autoimmune patient serum samples (positive for SSA (5) or Jo-1 (5)) and EBV positive samples (4). The correlation between signals from both assays is shown in FIG. 13A. Dashed lines represent positive thresholds determined as 3 standard deviations above the average signal of the controls in DBA assay and as 10% above cut-off sample signal in the Immunetics ELISA (as recommended by supplier).

All 43 controls (shown as lighter points) clustered in the lower left quadrant, scoring negative in both assays, as expected, without differences in the response from the "healthy" controls and autoimmune or EBV samples. Additionally, 16 of the suspected Lyme positive samples also scored as negative in both assays (shown as darker points in the lower left quadrant). This result is consistent with the notion that not all samples tested in whole lysate ELISA have reactivity towards C6 peptide. Another 11 samples from suspected Lyme positives scored positive in both assays (upper right quadrant).

7 samples were positive in the DBA assay and negative in ELISA. 1 sample was positive in ELISA and negative in DBA. There were no positives detected in the negative control sample group by either assay, therefore the false positive rate was likely below 2.3% (<1 in 43) for both assays. Assuming that the false positive rate is the same in the control sample group and putative Lyme positives, then the 7 samples positive in the DBA assay and negative in ELISA are likely true positives, because 7 of 35 positives in the DBA assay correspond to a rate of ~20%, well above the likely false positive rate.

3-fold serial dilutions (up to 81-fold final dilution) were made of 8 samples (P8, P13, P15, P18, P20, P29, P30, and P33) classified as positives and detected as C6 positive in DBA. These dilutions were then assayed back to back by C6 ELISA (Immunetics) and the DBA assay. Results are shown in FIG. 13B. The dashed lines represent serial dilutions for each of the 8 individual samples, starting from the undiluted sample which has an ID above the corresponding point and extending to more diluted samples (each subsequent point represents a 3-fold serial dilution). Samples that are in the top right quadrant without dilution (e.g., P30, P33, P15) are detected by both methods at higher sample concentrations, and become detectable only by the DBA assay as the concentrations decrease. At further dilutions, even DBA signals start declining In general, ELISA signals decline faster than DBA signals. This example demonstrates that the DBA assay format is more sensitive than the commercial ELISA assay for detecting anti-C6 antibodies.

EXAMPLE 7

Detection of Antibodies using the DBA Assay

In this experiment, the DBA assay format was used to detect antibodies for 8 antigens, including the HA affinity tag used in Examples 1-4. A list of the antigens tested in this experiment is shown in Table 1.

TABLE 1

List of antigens tested in Experiment 7.

| Name | Antigen Sequence | Antibodies |
|---|---|---|
| HA-tag | YPYDVPDYA (SEQ ID NO: 1) | Rabbit polyclonal IgG |
| AU1 | DTYRYI (SEQ ID NO: 3) | Rabbit polyclonal IgG |
| AU5 | TDFYLK (SEQ ID NO: 4) | Rabbit polyclonal IgG |
| cMyc | EKQLISEEDL (SEQ ID NO: 5) | Rabbit polyclonal IgG |
| His8 | HHHHHHHH (SEQ ID NO: 6) | Rabbit polyclonal IgG |
| Glu-Glu | EYMPME (SEQ ID NO: 7) | Rabbit polyclonal IgG |
| Avi-tag | GLNDIFEAQKIEQHE (SEQ ID NO: 8) | Rabbit polyclonal IgG |
| ECS | DDDDK (SEQ ID NO: 9) | Goat polyclonal IgG |

Figure 14:
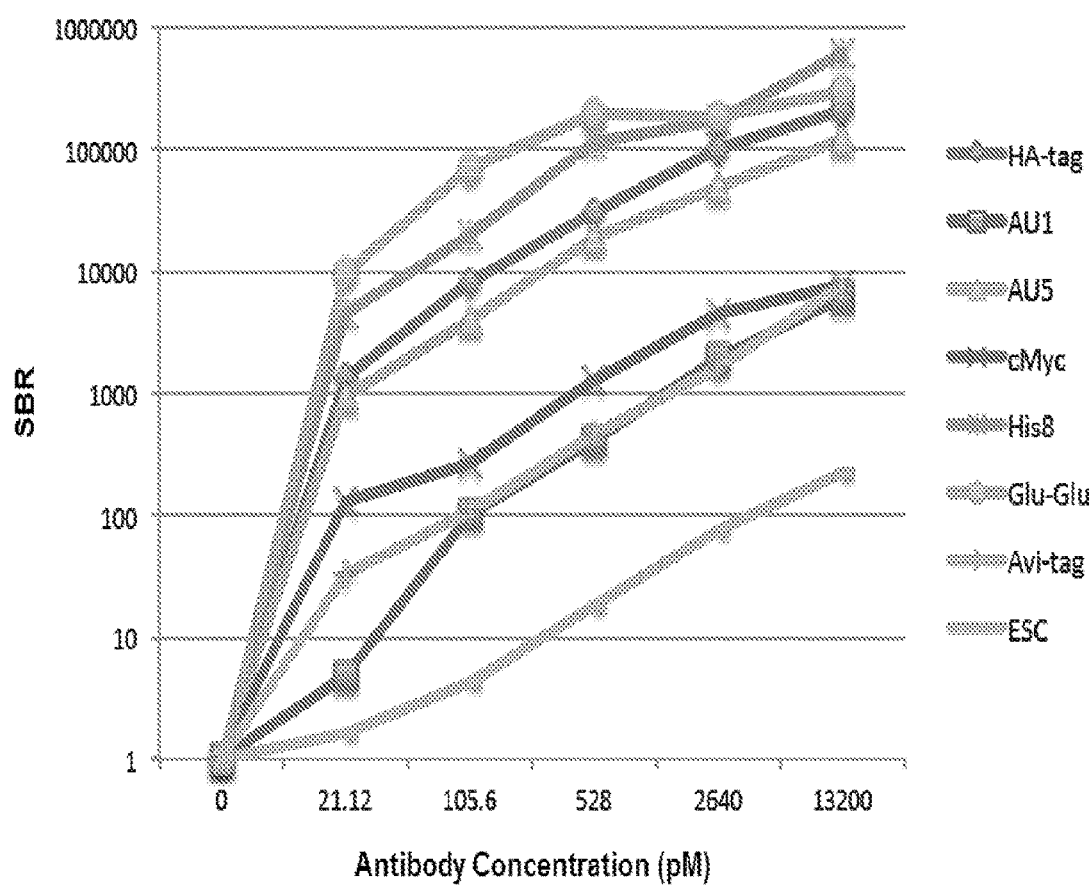
FIG. 14 shows the relationship between the signal-to-background ratios (SBR) and antibody analyte concentrations of DBA assays according to some embodiments of the present disclosure.

1 µl of 1% Streptavidin beads were loaded with of 1 µl of the capture probe (B) (0.8 nM). 10 µl of the detection probe (A) (0.08 nM) was then used upon capture of the antibody analytes. The signal-to-background ratios were plotted against the antibody analyte concentrations, as shown in FIG. 14. This example shows that the DBA assay format can be applied to detect a variety of antibody analytes.

EXAMPLE 8

Identification of Cancer-associated Epitopes

In this example, cancer-specific antibodies were detected by identification of antibody epitopes associated with cancer. Peptide-DNA conjugate libraries, such as a multiplexed DBA panel, were used to screen a panel of cancer and healthy control samples. A number of epitopes that were specific to the cancer samples were identified. FIG. 4 provides a schematic showing the DBA format using co-localized affinity for detection of antibodies.

The experiments identified p53, SOX1 and SOX2, CTAG1A and MUC1 as cancer-associated antibody epitopes, which was consistent with observations in the literature.

Figure 16:
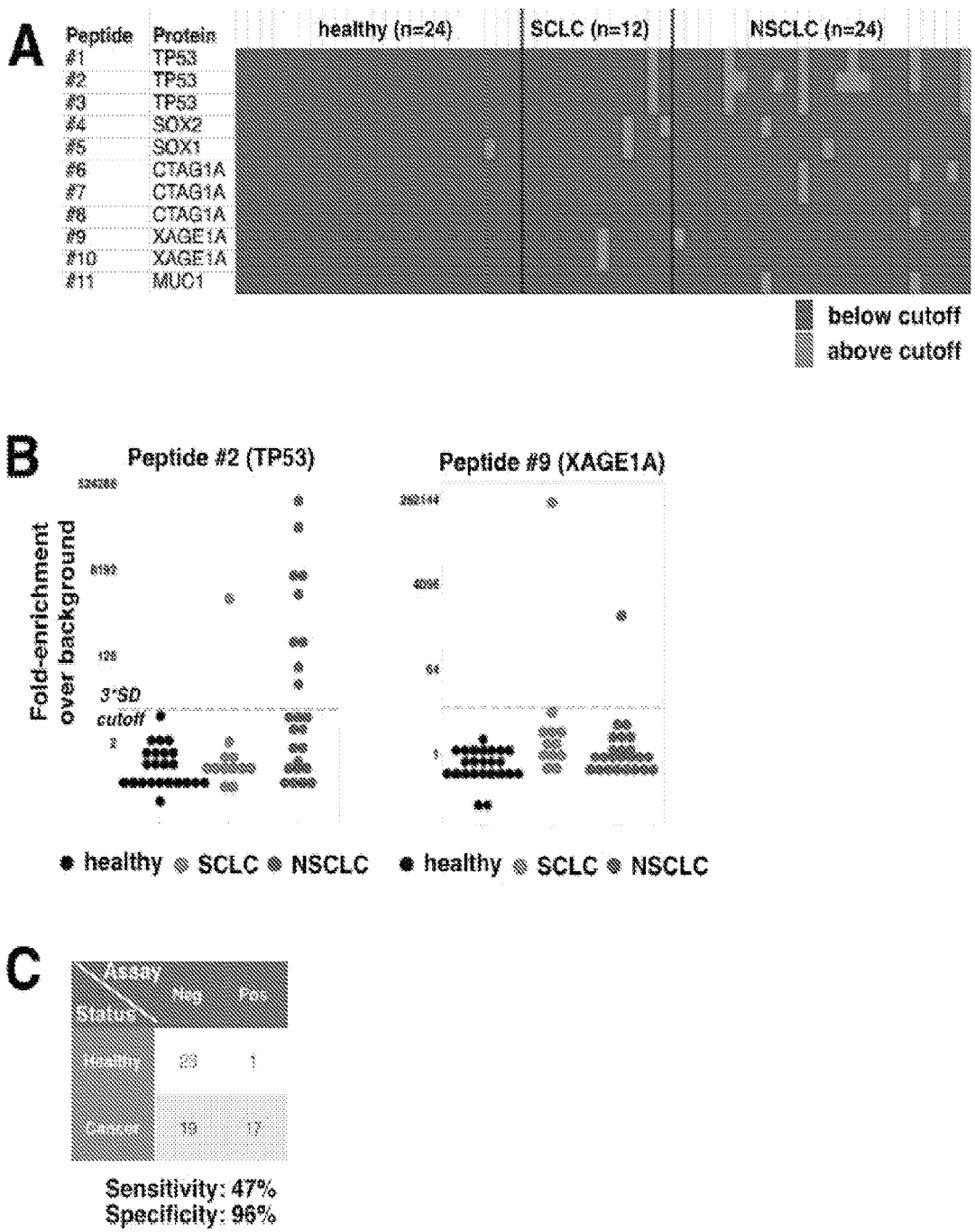
FIGS. 16A-16C show the identification of antibody epitopes associated with cancer, using peptide-DNA conjugate libraries to screen a panel of cancer and healthy control samples, according to some embodiments of the present disclosure.

Based on the high-throughput screen of serum antibody reactivity to peptides from ~100 cancer-related proteins, a set of 11 putatively cancer-specific peptide epitopes was developed. These 11 linear 20-mer peptides were synthesized, conjugated to DNA tags and deployed together in the multiplex DBA format (as part of a larger 25-plex set which included various controls). Sera from 24 healthy individuals and 36 treatment-naive lung cancer patients (26 samples at stages I & II; 10 samples at stages III & IV) were tested. These samples included 36 small cell lung cancer (SCLC) and non-small cell lung cancer (NSCLC) samples and 24 healthy controls. Detection of cancer-specific antibodies using the multiplexed DBA panel is shown in FIG. 16. FIG. 16A is a heat map showing responses to each peptide across all individuals (according to a binary cutoff at 3*SD of background). FIG. 16B shows representative data for two peptides: peptide #2 (immunodominant), and peptide #9 (individual-specific). Peptides #2 and #9 are shown in FIG. 16A. FIG. 16C shows overall classification performance of the 11-peptide panel.

Apart from peptide #5, which showed reactivity in a single healthy patient (among total n=24), all peptides yielded responses only in the cancer cohort (n=36) (96% specificity). As expected from the high-specificity/sensitivity features of the DBA assay format, signals for individual peptides showed large dynamic ranges (up to 105, for example, as shown in FIG. 16B) and positive responses were clearly resolved from negatives. A single peptide from TP53 (peptide #2) was observed to be able to detect responses in 10 of 36 cancer patients, which compares favorably to the rates detected using traditional whole-protein immunoassays for TP53 as in Soussi, "p53 Antibodies in the sera of patients with various types of cancer: a review," Cancer Res., 2000, 60(7):1777-88. The classification accuracy of this panel of 11 peptides (47% sensitivity, 96% specificity) also compares favorably with other tests for the detection of cancer. Boyle et al., "Clinical validation of an autoantibody test for lung cancer," Ann Oncol., 2011, 22(2):383-9; Jia et al., "Development of a multiplex autoantibody test for detection of lung cancer," PLoS One, 2014, 9(4):e95444.

In another aspect, the assay was able to identify tumor-associated antibody epitopes that are specific to individual patients, for examples, peptides specific for one or two patients were identified, and some patients had only one or two peptides reported, as shown in FIG. 16A. Thus, the assay can be used to detect and/or study a heterogeneous anti-cancer response, for example, by using a multiplexed assay format.

The invention claimed is:

1. A method for analyzing an antibody or antigen binding fragment thereof in a sample, comprising:
  (i) immobilizing a first polypeptide-polynucleotide conjugate on a substrate, the first polypeptide-polynucleotide conjugate comprising: (a) a first polypeptide comprising a first epitope for specific binding of an antibody or antigen binding fragment thereof; and (b) a first polynucleotide comprising a first primer sequence, a first identifying sequence that identifies the first polypeptide, and a first engaging sequence;
  (ii) contacting the substrate having the immobilized first polypeptide-polynucleotide conjugate with a sample containing or suspected of containing the antibody or antigen binding fragment thereof, whereby the first epitope specifically binds to the antibody or antigen binding fragment thereof in the sample;
  (iii) contacting the substrate having the immobilized first polypeptide-polynucleotide conjugate with a second polypeptide-polynucleotide conjugate, the second polypeptide-polynucleotide conjugate comprising: (a) a second polypeptide comprising a second epitope for specific binding of the antibody or antigen binding fragment thereof; and (b) a second polynucleotide comprising a second primer sequence, a second identifying sequence that identifies the second polypeptide, and a second engaging sequence, whereby the second epitope specifically binds to the antibody or antigen binding fragment thereof specifically bound to the first epitope, and whereby the first and second polynucleotides are engaged via the first and second engaging sequences; and
  (iv) sequencing all or a portion of the first and second polynucleotides engaged via the first and second engaging sequences,
  wherein the sequencing in step (iv) indicates the presence, absence, and/or amount of the antibody or antigen binding fragment thereof in the sample.

2. A method for analyzing an antibody or antigen binding fragment thereof in a sample, comprising:
  (i) immobilizing a first polypeptide-polynucleotide conjugate on a substrate, the first polypeptide-polynucleotide conjugate comprising: (a) a first polypeptide comprising a first epitope for specific binding of an antibody or antigen binding fragment thereof; and (b) a first polynucleotide comprising a first primer sequence, a first identifying sequence that identifies the first polypeptide, and a first engaging sequence;
  (ii) providing a second polypeptide-polynucleotide conjugate, the second polypeptide-polynucleotide conjugate comprising: (a) a second polypeptide comprising a second epitope for specific binding of the antibody or antigen binding fragment thereof; and (b) a second polynucleotide comprising a second primer sequence, a second identifying sequence that identifies the second polypeptide, and a second engaging sequence, wherein the second polypeptide-polynucleotide conjugate forms a complex with the immobilized first polypeptide-polynucleotide conjugate;
  (iii) contacting the substrate having the complex between the first and second polypeptide-polynucleotide conjugates with a sample containing or suspected of containing the antibody or antigen binding fragment thereof, wherein at least one molecule of the second polypeptide-polynucleotide conjugate specifically binds to the antibody or antigen binding fragment thereof specifically bound to the first polypeptide-polynucleotide conjugate, thereby forming a ternary complex;

(iv) washing the substrate under conditions that release molecules of the second polypeptide-polynucleotide conjugate that are not specifically bound to the antibody or antigen binding fragment thereof, while maintaining the ternary complex formed by specific binding;

(v) providing conditions under which the first and second polynucleotides are engaged via the first and second engaging sequences in the ternary complex formed by specific binding; and (vi) sequencing all or a portion of the first and second polynucleotides engaged via the first and second engaging sequences, wherein the sequencing in step (vi) indicates the presence, absence, and/or amount of the antibody or antigen binding fragment thereof in the sample.

3. The method of claim 1, wherein step (iv) further comprises extending both of the first and second polynucleotides.

4. The method of claim 1, wherein step (iv) further comprises extending only one of the first and second polynucleotides while the other is blocked from being extended by a polymerase.

5. The method of claim 1, wherein the sequencing comprises sequencing a polynucleotide comprising the sequences of the first primer, the first identifying sequence, the first and second engaging sequences, the second identifying sequence, and the second primer.

6. The method of claim 1, wherein the sequencing is performed using the first and/or second primer as the sequencing primer(s).

7. The method of claim 1, wherein the sequencing is performed by digital sequencing, high-throughput sequencing, and/or parallel sequencing.

8. The method of claim 1, wherein step (iv) further comprises amplifying all or a portion of the first and second polynucleotides.

9. The method of claim 8, wherein the amplifying comprises amplifying a polynucleotide comprising the sequences of the first primer, the first identifying sequence, the first and second engaging sequences, the second identifying sequence, and the second primer.

10. The method of claim 1, wherein each of the first and second polypeptides further comprises a tag comprising an affinity tag capable of specific binding by a capture agent.

11. The method of claim 1, wherein each of the first and second polypeptide-polynucleotide conjugates further comprises a purification tag comprising a polynucleotide sequence.

12. The method of claim 1, further comprising a step of fixing the antibody or antigen-binding fragment thereof in physical proximity to the first polypeptide-polynucleotide conjugate, upon specific binding of the antibody or antigen-binding fragment thereof to the first polypeptide-polynucleotide conjugate.

13. The method of claim 1, further comprising providing a third polypeptide-polynucleotide conjugate which comprises: (1) an antibody portion that specifically binds to the Fc portion of the antibody or antigen binding fragment thereof; and (2) a third polynucleotide that comprises a third primer sequence, a third identifying sequence that identifies the antibody portion, and a third engaging sequence, wherein the first or second polynucleotide is extended by a polymerase after the first and second polynucleotides are engaged, wherein the extended first or second polynucleotide is capable of engaging the third polynucleotide, and wherein the extended first or second polynucleotide is further extended by a polymerase using all or a portion of the third polynucleotide as a template.

14. The method of claim 2, wherein the complex between the first and second polypeptide-polynucleotide conjugates in step (ii) is formed by hybridization between the first and second polynucleotides.

15. The method of claim 14, wherein the washing step is performed under conditions that destabilize the hybridization between the first and second polynucleotides, thereby releasing molecules of the second polypeptide-polynucleotide conjugate that are not specifically bound to the antibody or antigen binding fragment thereof.

16. The method of claim 14, wherein the sequences involved in the hybridization between the first and second polynucleotides comprise one or more cleavable sites.

17. The method of claim 16, wherein the sequences involved in the hybridization are cleaved at the one or more cleavable sites before or during the washing step, thereby destabilizing the hybridization between the first and second polynucleotides.

18. The method of claim 14, wherein the second polypeptide-polynucleotide conjugate is kept in physical proximity to the first polypeptide-polynucleotide conjugate by a cleavable linker, before or after the first and second polypeptide-polynucleotide conjugates form the complex in step (ii).

19. The method of claim 18, wherein the cleavable linker is between the first and second polypeptide-polynucleotide conjugates, or between the second polypeptide-polynucleotide conjugate and the substrate.

20. The method of claim 19, wherein the cleavable linker is cleaved before or during the washing step, optionally under conditions that destabilize the hybridization between the first and second polynucleotides.

* * * * *